(12) United States Patent
Zhu et al.

(10) Patent No.: US 8,093,254 B2
(45) Date of Patent: Jan. 10, 2012

(54) ASPARTYL PROTEASE INHIBITORS

(75) Inventors: Zhaoning Zhu, Plainsboro, NJ (US);
Andrew Stamford, Chatham Township, NJ (US); Mihirbaran Mandal, Scotch Plains, NJ (US); Xiaoxiang Liu, River Vale, NJ (US)

(73) Assignee: Schering Corporation, Kenilworth, NJ (US)

( * ) Notice: Subject to any disclaimer, the term of this patent is extended or adjusted under 35 U.S.C. 154(b) by 55 days.

(21) Appl. No.: 12/517,744

(22) PCT Filed: Dec. 10, 2007

(86) PCT No.: PCT/US2007/025220
§ 371 (c)(1),
(2), (4) Date: Aug. 5, 2009

(87) PCT Pub. No.: WO2008/073365
PCT Pub. Date: Jun. 19, 2008

(65) Prior Publication Data
US 2010/0069406 A1    Mar. 18, 2010

Related U.S. Application Data

(60) Provisional application No. 60/874,419, filed on Dec. 12, 2006.

(51) Int. Cl.
*A01N 43/54*     (2006.01)
*A61K 31/505*    (2006.01)
*C07D 239/70*    (2006.01)
*C07D 471/00*    (2006.01)
*C07D 471/22*    (2006.01)
*C07D 487/00*    (2006.01)
*C07D 491/00*    (2006.01)

(52) U.S. Cl. ........ 514/257; 514/267; 544/247; 544/249; 544/251

(58) Field of Classification Search .............. 514/257, 514/267; 544/247, 249, 251
See application file for complete search history.

(56) References Cited

U.S. PATENT DOCUMENTS

| | | | |
|---|---|---|---|
| 5,338,740 A | 8/1994 | Carpino et al. | |
| 5,391,560 A | 2/1995 | Fuchs et al. | |
| 5,534,520 A | 7/1996 | Fisher et al. | |
| 5,731,431 A | 3/1998 | Nakagawa et al. | |
| 5,852,029 A | 12/1998 | Fisher et al. | |
| 5,883,096 A | 3/1999 | Lowe et al. | |
| 5,889,006 A | 3/1999 | Lowe et al. | |
| 5,935,958 A | 8/1999 | Kozlowski et al. | |
| 5,952,349 A | 9/1999 | Asberom et al. | |
| 5,977,138 A | 11/1999 | Wang et al. | |
| 6,037,352 A | 3/2000 | Lowe et al. | |
| 6,043,255 A | 3/2000 | Lowe et al. | |
| 6,066,636 A | 5/2000 | Kozlowski et al. | |
| 6,087,509 A | 7/2000 | Claussner et al. | |
| 6,294,554 B1 | 9/2001 | Clader et al. | |
| 6,344,473 B1 | 2/2002 | Hansen, Jr. et al. | |
| 6,458,812 B1 | 10/2002 | McKittrick et al. | |
| 6,713,726 B2 | 3/2004 | Tanaka et al. | |
| 7,183,070 B2 | 2/2007 | Cordell et al. | |
| 7,354,933 B2 | 4/2008 | Patek et al. | |
| 7,417,047 B2 | 8/2008 | Malamas et al. | |
| 7,423,158 B2 | 9/2008 | Malamas et al. | |
| 2002/0143024 A1 | 10/2002 | Murugesan et al. | |
| 2004/0248884 A1 | 12/2004 | Patek et al. | |
| 2005/0171112 A1 | 8/2005 | Schulz et al. | |
| 2005/0282825 A1 | 12/2005 | Malamas et al. | |
| 2005/0282826 A1 | 12/2005 | Malamas et al. | |
| 2006/0034848 A1 | 2/2006 | Kinoshita et al. | |
| 2006/0111370 A1 | 5/2006 | Zhu et al. | |
| 2007/0060575 A1 | 3/2007 | Zhu et al. | |
| 2007/0072852 A1 | 3/2007 | Zhu et al. | |

(Continued)

FOREIGN PATENT DOCUMENTS

DE    3643890    6/1988

(Continued)

OTHER PUBLICATIONS

Getchell, et al., Neurobiology of Aging, 24, 663-673 (2003).*

(Continued)

*Primary Examiner* — Andrew D Kosar
*Assistant Examiner* — Erich A Leeser
(74) *Attorney, Agent, or Firm* — Keith D. MacMillan; Gerard M. Devlin

(57) ABSTRACT

Disclosed are compounds of formula I (Chemical formula should be inserted here as it appears on abstract in paper form) Formula I or a stereoisomer, tautomer, or pharmaceutically acceptable salt or solvate thereof, wherein $R^1$, $R^2$, $R^3$, $R^4$, $R^{14}$, V, W, X, Y, Z, p, and ring A are as described in the specification. Also disclosed is the method of inhibiting aspartyl protease, and in particular, the methods of treating cardiovascular diseases, cognitive and neurodegenerative diseases. Also disclosed are methods of treating cognitive or neurodegenerative diseases using the compounds of formula I in combination with a cholinesterase inhibitor or a muscarinic $m_1$ agonist or $m_2$ antagonist.

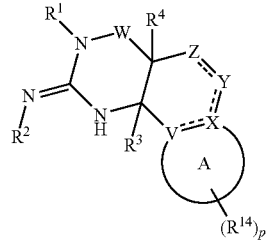

(I)

46 Claims, No Drawings

U.S. PATENT DOCUMENTS

| | | | |
|---|---|---|---|
| 2007/0072925 A1 | 3/2007 | Malamas et al. | |
| 2007/0287692 A1 | 12/2007 | Wu et al. | |
| 2007/0299087 A1 | 12/2007 | Berg et al. | |
| 2008/0108654 A1 | 5/2008 | Patek et al. | |
| 2008/0200445 A1 | 8/2008 | Zhu et al. | |

FOREIGN PATENT DOCUMENTS

| | | |
|---|---|---|
| EP | 0361341 | 4/1990 |
| EP | 0231919 | 1/1993 |
| EP | 0591781 | 4/1994 |
| EP | 0763054 | 3/1997 |
| EP | 0969011 | 1/2000 |
| EP | 1942105 | 7/2008 |
| JP | 11335518 | 12/1999 |
| WO | WO 89/03842 | 5/1989 |
| WO | WO 90/04917 | 5/1990 |
| WO | WO 93/04047 | 3/1993 |
| WO | WO 93/13064 | 7/1993 |
| WO | WO 93/23040 | 11/1993 |
| WO | WO 93/23041 | 11/1993 |
| WO | WO 95/03303 | 2/1995 |
| WO | WO 97/19064 | 5/1997 |
| WO | WO 97/45417 | 12/1997 |
| WO | WO 98/04525 | 2/1998 |
| WO | WO 99/05131 | 2/1999 |
| WO | WO 01/07440 | 2/2001 |
| WO | WO 01/44239 | 6/2001 |
| WO | WO 02/02512 | 1/2002 |
| WO | WO 02/02518 | 1/2002 |
| WO | WO 02/02520 | 1/2002 |
| WO | WO 02/74719 | 1/2002 |
| WO | WO 02/12243 | 2/2002 |
| WO | WO 02/088101 | 11/2002 |
| WO | WO 03/031412 | 4/2003 |
| WO | WO 03/035613 | 5/2003 |
| WO | WO 03/106405 | 12/2003 |
| WO | WO 2004/058727 | 7/2004 |
| WO | WO 2004/070050 | 8/2004 |
| WO | WO 2005/013020 | 2/2005 |
| WO | WO 2005/014540 | 2/2005 |
| WO | WO 2005/016876 | 2/2005 |
| WO | WO 2005/058311 * | 6/2005 |
| WO | WO 2005/097767 | 10/2005 |
| WO | WO 2005/103020 | 11/2005 |
| WO | WO 2005/103043 | 11/2005 |
| WO | WO 2005/108391 | 11/2005 |
| WO | WO 2005/113484 | 12/2005 |
| WO | WO 2006/002004 | 1/2006 |
| WO | WO 2006/009653 | 1/2006 |
| WO | WO 2006/009655 | 1/2006 |
| WO | WO 2006/014762 | 2/2006 |
| WO | WO 2006/014944 | 2/2006 |
| WO | WO 2006/017836 | 2/2006 |
| WO | WO 2006/017844 | 2/2006 |
| WO | WO 2006/024932 | 3/2006 |
| WO | WO 2006/041404 | 4/2006 |
| WO | WO 2006/041405 | 4/2006 |
| WO | WO 2006/044492 | 4/2006 |
| WO | WO 2006/044497 | 4/2006 |
| WO | WO 2006/065277 * | 6/2006 |
| WO | WO 2006/076284 | 7/2006 |
| WO | WO 2006/138192 | 12/2006 |
| WO | WO 2006/138195 | 12/2006 |
| WO | WO 2006/138217 | 12/2006 |
| WO | WO 2006/138230 | 12/2006 |
| WO | WO 2006/138264 | 12/2006 |
| WO | WO 2006/138265 | 12/2006 |
| WO | WO 2006/138266 | 12/2006 |
| WO | WO 2007/005366 | 1/2007 |
| WO | WO 2007/005404 | 1/2007 |
| WO | WO 2007/016012 | 2/2007 |
| WO | WO 2007/038271 | 4/2007 |
| WO | WO 2007/050721 | 5/2007 |
| WO | WO 2007/053506 | 5/2007 |
| WO | WO 2007/058580 | 5/2007 |
| WO | WO 2007/058582 | 5/2007 |
| WO | WO 2007/058583 | 5/2007 |
| WO | WO 2007/058601 | 5/2007 |
| WO | WO 2007/058602 | 5/2007 |
| WO | WO 2007/073284 | 6/2007 |
| WO | WO 2007/078813 | 7/2007 |
| WO | WO 2007/100536 | 9/2007 |
| WO | WO 2007/114771 | 10/2007 |
| WO | WO 2007/145568 | 12/2007 |
| WO | WO 2007/145569 | 12/2007 |
| WO | WO 2007/145570 | 12/2007 |
| WO | WO 2007/145571 | 12/2007 |
| WO | WO 2007/146225 | 12/2007 |
| WO | WO 2007/149033 | 12/2007 |
| WO | WO 2008/022024 | 2/2008 |
| WO | WO 2008/063114 | 5/2008 |
| WO | WO 2008/073365 | 6/2008 |
| WO | WO 2008/073370 | 6/2008 |
| WO | WO 2008/076043 | 6/2008 |
| WO | WO 2008/076044 | 6/2008 |
| WO | WO 2008/076045 | 6/2008 |
| WO | WO 2008/076046 | 6/2008 |
| WO | WO 2008/082785 | 7/2008 |
| WO | WO 2008/115552 | 9/2008 |
| WO | WO 2008/118379 | 10/2008 |

OTHER PUBLICATIONS

Bacon, et al., Ann NY Acad. Sci., 855, 723-31 (2002).*
Crino, et al., Ann Otol. Rhinol. Laryngol. 104, 655-61 (1995).*
Davies, et al., Neurobiol. Aging, 14, 353-7 (1993).*
Devanand, et al., Am. J. of Psychiatr., 157, 1399-405 (2000).*
Doty, et al., Brain Res. Bull., 18, 597-600 (1987).*
Barton, et al, "On the Structure of some Substituted 4,6-Pyrimidinediones", Polish J. Chem., vol. 69, pp. 235-245 (1995).
Berge, et al, "Pharmaceutical Salts", Journal of Pharmaceutical Sciences, vol. 66, No. 1, pp. 1-19 (1977).
Biennow et al, "CSF Markers for Incipient Alzheimer's Disease" Lancet Neurology, vol. 2, No. 10, pp. 605-613 (2003).
Bingham, et al, "Over one hundred solvates of sulfathiazole", Chem. Commun., pp. 603-604 (2001).
Breuer, et al "Reaction of 5,5-diphenylglycocyamidine and its N-alkyl derivatives with NH3 and with amines", Experientia, vol. 16, pp. 107 (1960) (Abstract).
Caira, et al, "Preparation and Crystal Characterization of a Polymorph, a Monohydrate, and an Ethyl Acetate Solvate of the Antifungal Fluconazole", Journal of Pharmaceutical Sciences, vol. 93, No. 3, pp. 601-611 (2004).
Call, "Derivatives of 5,5-diphenylglycocyamidine", Monatsh. Chemical, vol. 101, No. 2, pp. 344-356 (1970) (Abstract).
Coldham, et al, "Synthesis of the ABC Ring System of Manzamine A", J. Org. Chem., vol. 67, No. 17, pp. 6181-6187 (2002).
Doz, Novel Methods of Preparative Organic Chemistry IV, "The a-Addition of Immonium Ions and Anions to Isonitriles Accompanied by Secondary Reactions", Angew. Chem. Internat. Edit., vol. 1, No. 1, pp. 8-21 (1962).
Fernandez, et al, "Syntheses and Spectral Properties of β-Iodoureas and 2-Amino-4,4-diphenyl-2-oxazolines", J. Heterocyclic Chem., vol. 28, pp. 777-780 (1991).
Fernandez, et al, "Syntheses of Beta-iodourea derivatives of carbohydrates and glycosylamino-oxazolines", Carbohydrate Research, vol. 216, pp. 21-32 (1991).
Furukawa, et al, "Reaction of Biguanides and Related Compounds. IX. Condensation of N-Amidino-O-alkylisourea and 1-substituted 3-Amidino-2-thiourea with Benzil", Chemical & Pharmaceutical Bulletin, vol. 22, No. 1, pp. 1-7 (1974) (abstract).
Garratt, et al, "A Novel Synthesis of Dihydropyrimidines", J. Chem. Soc., Chem. Commun., pp. 568-569 (1987).
Gould, "Salt selection for basic drugs", International Journal of Pharmaceutics, vol. 33, pp. 201-217 (1986).
Hasegawa, et al, "The Synthesis of the 1,2,4-Thiadiazine-1,1-dioxides)", Bulletin of The Chemical Society of Japan, vol. 45, No. 6, pp. 1893-1896 (1972).
Hussein, et al, "Synthesen von α-Bromisothiocyanaten" Chem. Ber., vol. 112, pp. 1948-1955 (1979).

Kaleem, et al, "Protein-polymer grafts. II. A. Modification of amino acids. Lai modification of free arginine using 4-hydroxybenzil", Journal of Biological Physics, vol. 15, No. 3, pp. 63-68 (1987) (Abstract).

Kwon, et al, "Facile Synthesis of Substituted 2-Iminohydantoins", Synthetic Communications, vol. 17, No. 14, pp. 1677-1682 (1987).

Lempert, et al, "Hydantoins, thiohydantoins, glycocyamidines. II. Synthesis of some 3 (dialkylaminoalkyl)-5,5-diphenylglycocyamidines", Magyar Kem. Folyoirat, vol. 65, pp. 110-113 (1959) (Abstract).

Lampert, et al, "Hydantoins, thiohydantoins, glycocyamidines. III. The orientation in the monobenzylation of 5,5-diphenylglycocyamidine", Chemical Ber., vol. 92, pp. 235-239 (1959) (Abstract).

Lampert, et al, "Hydantoins, thiohydantoins, and glycocyamidines. IV. The orientation in the monomethylation of 5,5-diphenylglycocyamidine", Chemical Ber., vol. 92, pp. 1710-1711, (1959).

Lampert, et al, "Orientation in the condensation of benzil with monosubstituted guanidines", Experientia, vol. 15, pp. 412-413 (1959) (Abstract).

Lempert, et al, "Hydantoins, thiohydantoins, glycocyamidines. VIII. The condensation of benzil with benzylguanidine", Chemical Ber., vol. 94, pp. 796-807 (1961).

Lempert, et al, "Hydantoins, thiohydantoins, glycocyamidines. XIII. Mechanism of the rearrangement of 3-benzyl- to N2-benzyl-5,5-diphenylglycocyamidine and the debenzylation of the latter", Periodica Polytech, vol. 7, No. 1, pp. 7-19 (1963) (Abstract).

Lempert, et al, "Hydantoins, tkiohydantoins, and glycocyamidines. XX. Synthesis and condensation of 4'-nitro-4-methoxybenil with benzylguanidine", Periodica Polytech, vol. 8, No. 4, pp. 237-244 (1964) (Abstract).

Lempert, et al, "Mechanism of the base-induced rearrangement of 3-benzyl-5,5-diphenylglycocyamidine to N2- benzyl-5,5-diphenylglycocyamidine and the debenzylation of the latter", Abhandlungen der Deutschen Akademie der Wissenschaften zu Berlin, Klasse fuer Chemie, Geologie und Biologie, vol. 7, pp. 639-640 (1965) (Abstract).

Lempert-Streter, et al, "Hydantoins, thiohydantoins, and glycocyamidines. XII. Condensation of benzyl with guanidine and n-butylguanidine", Magy. Kem. Folyoirat, vol. 69, pp. 237-240 (1963) (Abstract).

Lin, et al, "Synthesis of Novel Guanidinoglycoside: 2-Glycosylamino 4,5-dihydro-6-pyrimidinone", J. Org. Chem., vol. 66, No. 24, pp. 8243-8247 (2001).

Melandri, et al, "New synthesis of the glycocyamidine group", Annali di Chimica, vol. 56, No. 10, pp. 1259-1266 (1966) (Abstract).

Merten, et al, "Notiz über eine neue Synthese von Derivaten des 1.4.2-Diazaphospholidins", Chem. Ber. vol. 102, pp. 2143-2145 (1969) (abstract not included).

Moloney, et al, "A Novel Series of 2,5-Substituted Tryptamine Derivatives as Vascular 5HT1B/1D Receptor Antagonists", J. Med. Chem., vol. 40, No. 15, pp. 2347-2362 (1997).

Mota, et al, Synthesis of N-hetarylthiourea Derivatives of Carbohydrates, Journal of Carbohydrate Chemistry, vol. 9, No. 6, pp. 837-851 (1990).

Na, et al, "Aspartic proteases of Plasmodium vivax are highly conserved in wild isolates", The Korean Journal of Parasitology, vol. 42, No. 2, pp. 61-66 (2004).

Oparil, et al, "The Renin-Angiotensin System (Second of Two Parts)", The New England Journal of Medicine, vol. 291, No. 9, pp. 446-457 (1974).

Page, et al, "A Convenient Preparation of Symmetrical and Unsymmetrical 1,2-Diketones: Application to Fluorinated Phenytoin Synthesis", Tetrahedron, vol. 48, No. 35, pp. 7265-7274 (1992).

Paik, et al, "α-Aminosulfonopeptides as Possible Functional Analogs of Penicillin; Evidence for their Extreme Instablility", Tetrahedron, vol. 52, No. 15, pp. 5303-5318 (1996).

Simig, et al, "Hydantoins, Thiohydantoins, Glycocyamidines—36—1,5,5- and 3,5,5-Triphenyl Derivatives", Tetrahedron, vol. 29, pp. 3571-3578 (1973).

Simig, et al, "Hydantoins, thiohydantoins and glycocyamidines, Part 43. The reaction of N-(t-butyl)-α-halo-α, α-diarylacetamides with cyanoamide", Acta Chimica Academiae Scientiarum Hungaricae, vol. 90, No. 1, pp. 93-101 (1976) (Abstract).

Stahl, et al, Handbook of Pharmaceutical Salts: Properties, Selection, and Use, (Eds.), Int'l. Union of Pure and Applied Chemistry, pp. 330 (2002).

Talaty, et al, "Preparation of Substituted Imidazolidinones and Hydantoins by Ring-Expansion of Aziridinones", Synlett, vol. 6, pp. 683-684 (1997).

Tamas, et al, "Hydantoins, thiohydantoins, glycocyamidines. XLII. Mass spectrometric behavior of 5,5-diphenylglycocyamidine and —hydratoin derivatives", Organic Mass Spectrometry, vol. 10, No. 5, pp. 390-395 (1975) (Abstract).

Van Tonder, et al, "Preparation and Physicochemical Characterization of 5 Niclosamide Solvates and 1 Hemisolvate", AAPS PharmSciTech, vol. 5, No. 1, Article 12, pp. 1-10 (2004).

Varga, et al, "Solution-phase parallel synthesis of 4,6-diarylpyrimidine-2-ylamines and 2-amino-5,5-disubstituted-3,5-dihydro-imidazol-4-ones via a rearrangement", Tetrahedron, vol. 59, pp. 655-662 (2003).

Wang, et al, "Use of Polymer-Supported Pd Reagents for Rapid and Efficient Suzuki Reactions Using Microwave Heating", Organic Letters, vol. 6, No. 16, pp. 2793-2796 (2004).

Weber, et al, "First synthesis of the main metabolite of secobarbital", Pharmazie, vol. 53, No. 11, pp. 771-775 (1998).

Winkler, et al, "Stereoselective Synthesis of the Tetracyclic Core of Manzamine via the Vinylogous Amide Photocycloaddition Cascades", Tetrahedron, vol. 54, pp. 7045-7056 (1998).

Yu, "Diverse Pathways for the Palladium(II)-Mediated Oxidation of Olefins by tert-Butylhydroperoxide", Organic Letters, vol. 4, No. 16, pp. 2727-2730 (2004).

Yusoff, et al, "Ring-Expansion of an Aziridinone to a Hexahydrotriazine through the Agency of a Novel Rearrangement", Tetrahedron Letters, vol. 37, No. 48, pp. 8695-8698 (1996).

Search Report for related ROC(Taiwan) Patent Application No. 093138776.

International Search Report for related PCT/US2004/041700, mailed Jun. 1, 2005.

International Search Report for related PCT/US2005/020446, mailed Jul. 26, 2006.

International Search Report for related PCT/US2008/002182, mailed Feb. 3, 2009.

International Search Report for corresponding PCT/US2007/025220, mailed May 21, 2008.

\* cited by examiner

ASPARTYL PROTEASE INHIBITORS

FIELD OF THE INVENTION

This invention relates to aspartyl protease inhibitors, pharmaceutical compositions comprising said compounds, their use in the treatment of cardiovascular diseases, cognitive and neurodegenerative diseases, and their use as inhibitors of the Human Immunodeficiency Virus, plasmepsins, cathepsin D and protozoal enzymes.

BACKGROUND

There are a number of aspartic proteases known to date, including pepsin A and C, renin, BACE, BACE 2, Napsin A, and cathepsin D, which have been implicated in pathological conditions. The role of renin-angiotensin system (RAS) in regulation of blood pressure and fluid electrolyte has been well established (Oparil, S, et al. N Engl J Med 1974; 291:381-401/446-57). The octapeptide Angiotensin-II, a potent vasoconstrictor and stimulator for release of adrenal aldosterone, was processed from the precursor decapeptide Angiotensin-I, which in turn is processed from angiotensinogen by the renin enzyme. Angiotensin-II is also found to play roles in vascular smooth muscle cell growth, inflammation, reactive oxygen species generation and thrombosis and influence atherogenesis and vascular damage. Clinically, the benefit of interruption of the generation of angiotensin-II through antagonism of conversion of angiotensin-I has been well known and there are a number of ACE inhibitor drugs on the market. The blockade of the earlier conversion of angiotensinogen to angiotensin-I, i.e. the inhibition of renin enzyme, is expected to have similar but not identical effects. Since renin is an aspartyl protease whose only natural substrate is angiotensinogen, it is believed that there would be less frequent adverse effect for controlling high blood pressure and related symptoms regulated by angiotensin-II through its inhibition.

Another protease, Cathepsin-D, is involved in lysosomal biogenesis and protein targeting, and may also be involved in antigen processing and presentation of peptide fragments. It has been linked to numerous diseases including, Alzheimer's, Disease, connective tissue disease, muscular dystrophy and breast cancer.

Alzheimer's Disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase activity responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result of β-secretase activity, inhibition of BACE-1 should inhibit formation of Aβ peptides. Thus inhibition of BACE-1 is a therapeutic approach to the treatment of AD and other cognitive and neurodegenerative diseases caused by or associated with Aβ plaque deposition.

Glaucoma, a major cause of blindness worldwide, is an example of another neurodegenerative disease in which Aβ may play a causative role. Glaucoma is commonly linked to elevated intraocular pressure (IOP). It is well known that raised IOP can lead to irreversible destruction of retinal ganglion cells (RGCs). However, the presence of glaucomatous damage in patients with normalized IOP has focused a growing body of work on alternative strategies to those regulating IOP. Recent evidence suggests that targeting Aβ deposition associated with Alzheimers Disease may provide a therapeutic avenue in glaucoma treatment. For example, Guo et al. report evidence from an animal (rat) model of glaucoma supporting the involvement of Aβ in glaucoma-induced apoptosis of RGCs and show that the use of β-secretase inhibitors and other agents targeting multiple phases of the Aβ pathway raise the possibility of a neuroprotectice approach to the treatment of glaucoma. Guo, et al., PNAS, vol. 104, no. 33, pp. 13444-13449, August 2007.

Aβ is also thought to play a causative role in impaired olfactory sensory function in patients with the diagnosis of probable Alzheimer's disease, Parkinson's disease, and Down's syndrome. Getchell, et al., Neurobiology of Aging, 24 (2003) 663-673. Bacon, et al., Ann NY Acad Sci 2002; 855:723-31. Crino, et al., Ann 0 to 1 Rhinol Laryngol 1995; 104:655-61. Davies, et al., Neurobiol Aging 1993; 14:353-7. Devanand, et al., Am J Psychiatr 2000; 157:1399-405. Doty, et al., Brain Res Bull 1987; 18:597-600.

Human immunodeficiency virus (HIV), is the causative agent of acquired immune deficiency syndrome (AIDS). It has been clinically demonstrated that compounds such as indinavir, ritonavir and saquinavir which are inhibitors of the HIV aspartyl protease result in lowering of viral load. As such, the compounds described herein would be expected to be useful for the treatment of AIDS. Traditionally, a major target for researchers has been HIV-1 protease, an aspartyl protease related to renin.

In addition, Human T-cell leukemia virus type I (HTLV-I) is a human retrovirus that has been clinically associated with adult T-cell leukemia and other chronic diseases. Like other retroviruses, HTLV-I requires an aspartyl protease to process viral precursor proteins, which produce mature virions. This makes the protease an attractive target for inhibitor design. (Moore, et al. Purification of HTLV-I Protease and Synthesis of Inhibitors for the treatment of HTLV-I Infection 55$^{th}$ Southeast Regional Meeting of the American Chemical Society, Atlanta, Ga., US Nov. 16-19, 2003 (2003), 1073. CODEN; 69EUCH Conference, AN 2004:137641 CAPLUS).

Plasmepsins are essential aspartyl protease enzymes of the malarial parasite. Compounds for the inhibition of aspartyl proteases plasmepsins, particularly I, II, IV and HAP, are in development for the treatment of malaria. (Freire, et al. WO 2002074719. Na Byoung-Kuk, et al., Aspartic proteases of *Plasmodium vivax* are highly conserved in wild isolates, Korean Journal of Parasitology (2004 June), 42(2) 61-6. Journal code: 9435800) Furthermore, compounds used to target aspartyl proteases plasmepsins (e.g. I, II, IV and HAP), have been used to kill malarial parasites, thus treating patients thus afflicted.

Compounds that act as aspartyl protease inhibitors are described, for example in application U.S. Ser. No. 11/010, 772, filed on Dec. 13, 2004, and U.S. Ser. No. 11/451,541, filed on Jun. 12, 2006, herein incorporated by reference.

WO/9304047, herein incorporated by reference, describes compounds having a quinazolin-2-(thi)one nucleus. The document alleges that the compounds described therein are inhibitors of HIV reverse transcriptase.

US Publication No. US 2005/0282826 A1, herein incorporated by reference, describes diphenylimidazopyrimidine or -imidazole amines, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognative impairment, Down's syndrome, hereditary cerebral hemorrhage with amyloidosis of the Dutch type, cerebral amyloid angiopathy and degenerative dementia.

US Publication No. US 2005/0282825 A1, herein incorporated by reference, describes amino-5,5-diphenylimidazolones, which are said to be useful for the therapeutic treatment, prevention or amelioration of a disease or disorder characterized by elevated β-amyloid deposits or β-amyloid levels in a patient. Disease states mentioned in the publication include Alzheimer's disease, mild cognative impairment, Down's syndrome, hereditary cerebral hemorrhage with amyloidosis of the Dutch type, cerebral amyloid angiopathy and degenerative dementia.

Other publications that disclosed compounds that are useful for treating Alzherimer's disease include WO 2006/044492, which discloses spiropiperidine compounds that are said to be inhibitors of β-secretase, and WO 2006/041404, which discloses substituted amino compounds that are said to be useful for the treatment or prophylaxix of Aβ related pathologies. Both these publications are incorporated by reference.

SUMMARY OF THE INVENTION

The present invention relates to compounds having the following structural formula:

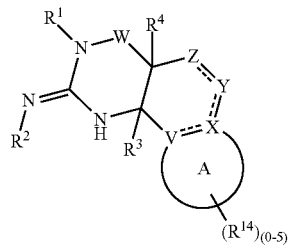

or a stereoisomer, tautomer, or pharmaceutically acceptable salt or solvate thereof, wherein the dashed line (-----) in Formula (I) represent single or double bonds;

ring A together with V and X forms a mono or multicyclic 4 to 12 membered cycloalkylene, cycloalkenylene, heterocycloalkylene or heterocycloalkenylene wherein the heteroatom or heteroatoms of said heterocycloalkylene or heterocycloalkenylene are independently selected from the group consisting of —O—, —S—, —S(O)$_{1-2}$— and —N(R$^5$)—;

or ring A together with V and X forms a mono or multicyclic 4 to 12 membered arylene or heteroarylene;

W is —S(O)—, —S(O)$_2$—, —C(O)— or —O—;

X is —N— or —C(R$^{14}$)—, with the proviso that when X is —N—, Y cannot be —S—;

Y is —N(R$^5$)—, —O—, —S—, —C(R$^6$)(R$^{6a}$)—, —C(O)—, —S(O)— or —S(O)$_2$—;

Z is a bond, —N(R$^5$)—, —O—, —S—, —C(R$^6$)(R$^{6a}$)—, —C(O)—, —S(O)— or —S(O)$_2$— with the proviso that when Z is —O—, —S—, —S(O)— or —S(O)$_2$, Y cannot be —O—, —S—, —S(O)— or —S(O)$_2$—;

or Z and Y taken together is —C=C—, —N=C— or —C=N—;

or X and Y taken together is —C=C—, —N=C— or —C=N—;

V is —C(R$^{14}$)—;

or V and X taken together forms —C=C—;

with the proviso that there are no cumulative double bonds between V, X, Y, Z and the ring atoms of ring A adjacent to V and X;

R$^1$, R$^2$ and R$^5$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —CN, —C(=NR$^{11}$)R$^8$, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^{11}$)(R$^{12}$), provided that R$^1$ and R$^5$ are not both selected from —NO$_2$, —N=C(R$^8$)$_2$ and —N(R$^{11}$)(R$^{12}$);

R$^3$, R$^4$, R$^6$, R$^{6a}$ and R$^7$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$, —N(R$^{11}$)C(O)N(R$^{12}$)(R$^{13}$), —N(R$^{11}$)C(O)OR$^9$ and C(=NOH)R$^8$;

or a R$^6$ and a R$^{6a}$ group together with the carbon to which they are attached form a carbonyl;

$R^8$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

$R^{14}$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —N(R$^{15}$)C(O)N(R$^{16}$)(R$^{17}$), —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) or —N(R$^{15}$)C(O)OR$^{16}$;

or two $R^{14}$ groups together with the carbon to which they are attached form a carbonyl;

$R^9$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, and heterocycloalkenylheteroaryl;

$R^{10}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl and —N(R$^{15}$)(R$^{16}$);

$R^{11}$, $R^{12}$ and $R^{13}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$), —S(O)$_2$N(R$^{15}$)(R$^{16}$) and —CN;

$R^{15}$, $R^{16}$ and $R^{17}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, R$^{18}$-alkyl, R$^{18}$-arylalkyl, R$^{18}$-heteroarylalkyl, R$^{18}$-cycloalkylalkyl, R$^{18}$-heterocycloalkylalkyl, R$^{18}$-arylcycloalkylalkyl, R$^{18}$-heteroarylcycloalkylalkyl, R$^{18}$-arylheterocycloalkylalkyl, R$^{18}$-heteroarylheterocycloalkylalkyl, R$^{18}$-cycloalkyl, R$^{18}$-arylcycloalkyl, R$^{18}$-heteroarylcycloalkyl, R$^{18}$-heterocycloalkyl, R$^{18}$-arylheterocycloalkyl, R$^{18}$-heteroarylheterocycloalkyl, R$^{18}$-alkenyl, R$^{18}$-arylalkenyl, R$^{18}$-cycloalkenyl, R$^{18}$-arylcycloalkenyl, R$^{18}$-heteroarylcycloalkenyl, R$^{18}$-heterocycloalkenyl, R$^8$-arylheterocycloalkenyl, R$^{18}$-heteroarylheterocycloalkenyl, R$^{18}$-alkynyl, R$^{18}$-arylalkynyl, R$^{18}$-aryl, R$^{18}$-cycloalkylaryl, R$^{18}$-heterocycloalkylaryl, R$^{18}$-cycloalkenylaryl, R$^{18}$-heterocycloalkenylaryl, R$^{18}$-heteroaryl, R$^{18}$-cycloalkylheteroaryl, R$^{18}$-heterocycloalkylheteroaryl, R$^{18}$-cycloalkenylheteroaryl, and R$^{18}$-heterocycloalkenylheteroaryl; or $R^{15}$, $R^{16}$ and $R^{17}$ are

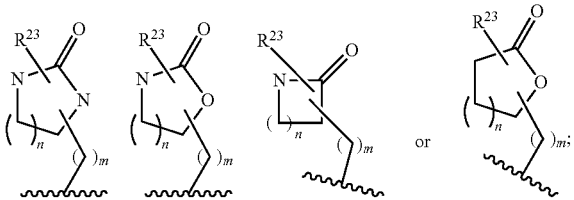

wherein $R^{23}$ numbers 0 to 5 substituents, m is 0 to 6 and n is 0 to 5;

$R^{18}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —$NO_2$, halo, HO-alkoxyalkyl, —$CF_3$, —CN, alkyl-CN, —C(O)$R^{19}$, —C(O)OH, —C(O)O$R^{19}$, —C(O)NH$R^{20}$, —C(O)$NH_2$, —C(O)$NH_2$—C(O)N(alkyl)$_2$, —C(O)N(alkyl)(aryl), —C(O)N(alkyl)(heteroaryl), —S$R^{19}$, —S(O)$_2R^{20}$, —S(O)$NH_2$, —S(O)NH(alkyl), —S(O)N(alkyl)(alkyl), —S(O)NH(aryl), —S(O)$_2NH_2$, —S(O)$_2$NH$R^{19}$, —S(O)$_2$NH(heterocycloalkyl), —S(O)$_2$N(alkyl)$_2$, —S(O)$_2$N(alkyl)(aryl), —O$CF_3$, —OH, —O$R^{20}$, —O-heterocycloalkyl, —O-cycloalkylalkyl, —O-heterocycloalkylalkyl, —$NH_2$, —NH$R^{20}$, —N(alkyl)$_2$, —N(arylalkyl)$_2$, —N(arylalkyl)(heteroarylalkyl), —NHC(O)$R^{20}$, —NHC(O)$NH_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two $R^{18}$ moieties on adjacent carbons can be linked together to form

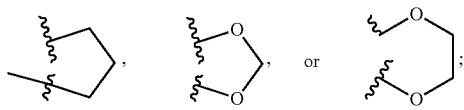

$R^{19}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl;

$R^{20}$ is halo substituted aryl, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl, and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, in $R^1$, $R^2$, $R^3$, $R^4$, $R^5$, $R^6$, $R^{6a}$, $R^7$, $R^8$, $R^9$, $R^{10}$, $R^{11}$, $R^{12}$, $R^{13}$ and $R^{14}$;

are independently unsubstituted or substituted by 1 to 5 $R^{21}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —O$R^{15}$, —C(O)$R^{15}$, —C(O)O$R^{15}$, —C(O)N($R^{15}$)($R^{16}$), —S$R^{15}$, —S(O)N($R^{15}$)($R^{16}$), —CH($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —$CH_2$—N($R^{15}$)C(O)N($R^{16}$)($R^{17}$), —$CH_2$—$R^{15}$; —$CH_2$N($R^{15}$)($R^{16}$), —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —S(O)$R^{15}$, —$N_3$, —$NO_2$ and —S(O)$_2R^{15}$;

and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in $R^{21}$ are independently unsubstituted or substituted by 1 to 5 $R^{22}$ groups independently selected from the group consisting of alkyl, arylalkyl, heteroarylalkyl, cycloalkylalkyl, heteroarylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —$CF_3$, —CN, —O$R^{15}$, —C(O)$R^{15}$, —C(O)O$R^{15}$, -alkyl-C(O)O$R^{15}$, —C(O)N($R^{15}$)($R^{16}$), —S$R^{15}$, —S(O)N($R^{15}$)($R^{16}$), —S(O)$_2$N($R^{15}$)($R^{16}$), —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —$N_3$, —$NO_2$, —S(O)$R^{15}$ and —S(O)$_2R^{15}$;

or two $R^{21}$ or two $R^{22}$ moieties on adjacent carbons can be linked together to form

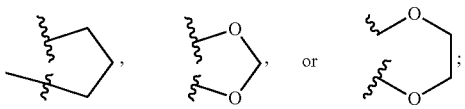

and when $R^{21}$ or $R^{22}$ are selected from the group consisting of —C(=NOR$^{15}$)R$^{16}$, —N(R$^{15}$)C(O)R$^{16}$, —CH$_2$—N(R$^{15}$)C(O)R$^{16}$, —N(R$^{15}$)S(O)R$^{16}$, —N(R$^{15}$)S(O)$_2$R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$ and —CH$_2$—N(R$^{15}$)C(O)OR$^{16}$, R$^{15}$ and R$^{16}$ together can be a C$_2$ to C$_4$ chain wherein, optionally, one, two or three ring carbons can be replaced by —C(O)— or —N(H)— and R$^{15}$ and R$^{16}$, together with the atoms to which they are attached, form a 5 to 7 membered ring, optionally substituted by R$^{23}$;

$R^{23}$ is 1 to 5 groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —OR$^{24}$, —C(O)R$^{24}$, —C(O)OR$^{24}$, —C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$; and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in R$^{23}$ are independently unsubstituted or substituted by 1 to 5 R$^{27}$ groups independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CF$_3$, —CN, —OR$^{24}$, —C(O)R$^{24}$, —C(O)OR$^{24}$, alkyl-C(O)OR$^{24}$, —C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$;

$R^{24}$, $R^{25}$ and $R^{26}$ are independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, R$^{27}$-alkyl, R$^{27}$-arylalkyl, R$^{27}$-heteroarylalkyl, R$^{27}$-cycloalkylalkyl, R$^{27}$-heterocycloalkylalkyl, R$^{27}$-arylcycloalkylalkyl, R$^{27}$-heteroarylcycloalkylalkyl, R$^{27}$-arylheterocycloalkylalkyl, R$^{27}$-heteroarylheterocycloalkylalkyl, R$^{27}$-cycloalkyl, R$^{27}$-arylcycloalkyl, R$^{27}$-heteroarylcycloalkyl, R$^{27}$-heterocycloalkyl, R$^{27}$-arylheterocycloalkyl, R$^{27}$-heteroarylheterocycloalkyl, R$^{27}$-alkenyl, R$^{27}$-arylalkenyl, R$^{27}$-cycloalkenyl, R$^{27}$-arylcycloalkenyl, R$^{27}$-heteroarylcycloalkenyl, R$^{27}$-heterocycloalkenyl, R$^{27}$-arylheterocycloalkenyl, R$^{27}$-heteroarylheterocycloalkenyl, R$^{27}$-alkynyl, R$^{27}$-arylalkynyl, R$^{27}$-aryl, R$^{27}$-cycloalkylaryl, R$^{27}$-heterocycloalkylaryl, R$^{27}$-cycloalkenylaryl, R$^{27}$-heterocycloalkenylaryl, R$^{27}$-heteroaryl, R$^{27}$-cycloalkylheteroaryl, R$^{27}$-heterocycloalkylheteroaryl, R$^{27}$-cycloalkenylheteroaryl and R$^{27}$-heterocycloalkenylheteroaryl;

$R^{27}$ is 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —NO$_2$, halo, —CF$_3$, —CN, alkyl-CN, —C(O)R$^{28}$, —C(O)OH, —C(O)OR$^{28}$, —C(O)NHR$^{29}$, —C(O)N(alkyl)$_2$, —C(O)N(alkyl)(aryl), —C(O)N(alkyl)(heteroaryl), —SR$^{28}$, —S(O)$_2$R$^{29}$, —S(O)NH$_2$, —S(O)NH(alkyl), —S(O)N(alkyl)(alkyl), —S(O)NH(aryl), —S(O)$_2$NH$_2$, —S(O)$_2$NHR$^{28}$, —S(O)$_2$NH(aryl), —S(O)$_2$NH(heterocycloalkyl), —S(O)$_2$N(alkyl)$_2$, —S(O)$_2$N(alkyl)(aryl), —OH, —OR$^{29}$, —O-heterocycloalkyl, —O-cycloalkylalkyl, —O-heterocycloalkylalkyl, —NH$_2$, —NHR$^{29}$, —N(alkyl)$_2$, —N(arylalkyl)$_2$, —N(arylalkyl)(heteroarylalkyl), —NHC(O)R$^{29}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{29}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

$R^{28}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl; and $R^{29}$ is alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl or heterocycloalkenylheteroaryl.

In another embodiment, the present invention provides a pharmaceutical composition comprising at least one compound of formula I and a pharmaceutically acceptable carrier.

In another embodiment, the present invention provides a method of inhibiting aspartyl proteases comprising administering at least one compound of formula I to a patient in need of such treatment.

In another embodiment, the present invention provides a method of inhibiting the deposition and/or accumulation of aspartyl proteases comprising administering at least one compound of formula I to a patient in need of such treatment.

In another embodiment, the present invention provides a method of inhibiting the deposition and/or accumulation of Aβ plaque comprising administering at least one compound of formula I to a patient in need of such treatment.

In other non-limiting embodiments, the invention provides: a method of treating cardiovascular diseases such as hypertension, renal failure, congestive heart failure or another disease modulated by renin inhibition; a method of treating Human Immunodeficiency Virus; a method of treating cognitive or neurodegenerative diseases such as Alzheimer's Disease, glaucoma, and/or impaired olfactory function; a method of inhibiting plasmepsins I and II for treatment of malaria; a method of inhibiting Cathepsin D for the treatment of Alzheimer's Disease, breast cancer, and/or ovarian cancer; and a method of inhibiting protozoal enzymes, for example inhibition of *plasmodium falciparnum*, for the treatment of fungal infections. These methods of treatment independently comprise administering at least one compound of formula I (or a stereoisomer, tautomer, or pharmaceutical salts and/or solvates thereof), to a patient in need of such treatment. In particular, the invention comprises a method of treating Alzheimer's Disease comprising administering at least one compound of formula I to a patient in need of such treatment.

In another embodiment, the present invention provides a method of treating Alzheimer's Disease comprising administering to a patient in need of such treatment a combination of at least one compound of formula I and a cholinesterase inhibitor or a muscarinic $m_1$ agonist or $m_2$ antagonist.

In another embodiment, the present invention provides a method of inhibiting apoptosis of retinal ganglion cells and a method of treating or preventing glaucoma comprising administering to a patient in need of such treatment at least one compound of formula I alone or in combination with one or more additional active agents. Such additional agents include, but are not limited to, a beta-amyloid antibody, Congo Red, and an intraocular pressure reducing agent.

In another embodiment, the present invention provides a method of treating glaucoma comprising administering to a patient in need of such treatment at least one compound of formula I alone or in combination with one or more additional active agents. Such additional agents include, but are not limited to, a beta-amyloid antibody, Congo Red, and an intraocular pressure reducing agents.

In another embodiment, the present invention provides a kit comprising in separate containers in a single package pharmaceutical compositions for use in combination, in which one container comprises a compound of formula I in a pharmaceutically acceptable carrier and a second container comprises a cholinesterase inhibitor or a muscarinic $m_1$ agonist or $m_2$ antagonist in a pharmaceutically acceptable carrier, the combined quantities being an effective amount to treat one or more diseases or conditions described herein, such as a cognitive disease or neurodegenerative disease such as Alzheimer's Disease.

DETAILED DESCRIPTION

Unless otherwise indicated, it is understood that divalent groups are to be read left to right.

The present invention relates to compounds having the structural Formula (I)

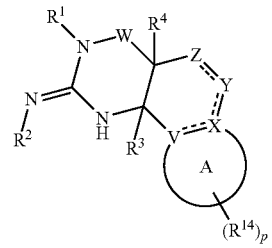

Formula (I)

or a stereoisomer, tautomer, or pharmaceutically acceptable salt or solvate thereof, wherein $R^1$, $R^2$, $R^3$, $R^4$, W, Z, Y, X, V, A, p, and each $R^{14}$ is selected independently of each other and wherein:

p is an integer from 0 to 5;

the dashed line (-----) in Formula (I) represent single or double bonds;

ring A together with V and X forms a mono or multicyclic 4 to 12 membered cycloalkylene, cycloalkenylene, heterocycloalkylene or heterocycloalkenylene wherein the heteroatom or heteroatoms of said heterocycloalkylene or heterocycloalkenylene are independently selected from the group consisting of —O—, —S—, —S(O)—, —S(O)$_2$— and —N($R^5$)—;

or ring A together with V and X forms a mono or multicyclic 4 to 12 membered arylene or heteroarylene;

W is —S(O)—, —S(O)$_2$—, —C(O)— or —O—;

X is —N— or —C($R^{30}$)—, with the proviso that when X is —N—, Y cannot be —S—;

Y is —N($R^5$)—, —O—, —S—, —C($R^6$)($R^{6a}$)—, —C(O)—, —S(O)— or —S(O)$_2$—;

Z is a bond, —N($R^5$)—, —O—, —S—, —C($R^6$)($R^{6a}$)—, —C(O)—, —S(O)— or —S(O)$_2$— with the proviso that when Z is —O—, —S—, —S(O)— or —S(O)$_2$, Y cannot be —O—, —S—, —S(O)— or —S(O)$_2$—;

or Z and Y taken together is —C=C—, —N=C— or —C=N—;

or X and Y taken together is —C=C—, —N=C— or —C=N—;

V is —C(R$^{31}$)—;

or V and X taken together forms —C=C—;

with the proviso that there are no cumulative double bonds between V, X, Y, Z and the ring atoms of ring A adjacent to V and X;

each of R$^1$, R$^2$ and R$^5$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —CN, —C(=NR$^{11}$)R$^8$, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^{11}$)(R$^{12}$), provided that R$^1$ and R$^5$ are not both selected from —NO$_2$, —N=C(R$^8$)$_2$ and —N(R$^{11}$)(R$^{12}$);

each of R$^3$, R$^4$, R$^6$, R$^{6a}$ and R$^7$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$, —N(R$^{11}$)C(O)N(R$^{12}$)(R$^{13}$), —N(R$^{11}$)C(O)OR$^9$ and —C(=NOH)R$^8$;

or a R$^6$ and a R$^{6a}$ group together with the carbon to which they are attached form a carbonyl;

each R$^8$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

each R$^{14}$ is independently selected from the group consisting of a bond, H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —N(R$^{15}$)C(O)N(R$^{16}$)(R$^{17}$), —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), and —N(R$^{15}$)C(O)OR$^{16}$;

or two R$^{14}$ groups together with the carbon to which they are attached form a carbonyl;

each R$^9$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, and heterocycloalkenylheteroaryl;

each R$^{10}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl and —N(R$^{15}$)(R$^{16}$);

each of R$^{11}$, R$^{12}$ and R$^{13}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —C(O)R$^8$, —C(O)OR$^9$, —S(O)R$^{10}$, —S(O)$_2$R$^{10}$, —C(O)N(R$^{15}$)(R$^{16}$), —S(O)N(R$^{15}$)(R$^{16}$), —S(O)$_2$N(R$^{15}$)(R$^{16}$) and —CN;

each of $R^{15}$, $R^{16}$ and $R^{17}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, $R^{18}$-alkyl, $R^{18}$-arylalkyl, $R^{18}$-heteroarylalkyl, $R^{18}$-cycloalkylalkyl, $R^{18}$-heterocycloalkylalkyl, $R^{18}$-arylcycloalkylalkyl, $R^{18}$-heteroarylcycloalkylalkyl, $R^{18}$-arylheterocycloalkylalkyl, $R^{18}$-heteroarylheterocycloalkylalkyl, $R^{18}$-cycloalkyl, $R^{18}$-arylcycloalkyl, $R^{18}$-heteroarylcycloalkyl, $R^{18}$-heterocycloalkyl, $R^{18}$-arylheterocycloalkyl, $R^{18}$-heteroarylheterocycloalkyl, $R^{18}$-alkenyl, $R^{18}$-arylalkenyl, $R^{18}$-cycloalkenyl, $R^{18}$-arylcycloalkenyl, $R^{18}$-heteroarylcycloalkenyl, $R^{18}$-heterocycloalkenyl, $R^{18}$-arylheterocycloalkenyl, $R^{18}$-heteroarylheterocycloalkenyl, $R^{18}$-alkynyl, $R^{18}$-arylalkynyl, $R^{18}$-aryl, $R^{18}$-cycloalkylaryl, $R^{18}$-heterocycloalkylaryl, $R^{18}$-cycloalkenylaryl, $R^{18}$-heterocycloalkenylaryl, $R^{18}$-heteroaryl, $R^{18}$-cycloalkylheteroaryl, $R^{18}$-heterocycloalkylheteroaryl, $R^{18}$-cycloalkenylheteroaryl, and $R^{18}$-heterocycloalkenylheteroaryl;

each $R^{18}$ is independently 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —$NO_2$, halo, HO-alkoxyalkyl, —$CF_3$, —CN, alkyl-CN, —C(O)$R^{19}$, —C(O)OH, —C(O)O$R^{19}$, —C(O)NH$R^{20}$, —C(O)$NH_2$, —C(O)$NH_2$—C(O)N(alkyl)$_2$, —C(O)N(alkyl)(aryl), —C(O)N(alkyl)(heteroaryl), —S$R^{19}$, —S(O)$_2R^{20}$, —S(O)$NH_2$, —S(O)NH(alkyl), —S(O)N(alkyl)(alkyl), —S(O)NH(aryl), —S(O)$_2NH_2$, —S(O)$_2$NH$R^{19}$, —S(O)$_2$NH(heterocycloalkyl), —S(O)$_2$N(alkyl)$_2$, —S(O)$_2$N(alkyl)(aryl), —O$CF_3$, —OH, —O$R^{20}$, —O-heterocycloalkyl, —O-cycloalkylalkyl, —O-heterocycloalkylalkyl, —$NH_2$, —NH$R^{20}$, —N(alkyl)$_2$, —N(arylalkyl)$_2$, —N(arylalkyl)-(heteroarylalkyl), —NHC(O)$R^{20}$, —NHC(O)$NH_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two $R^{18}$ moieties on adjacent carbons can be linked together to form

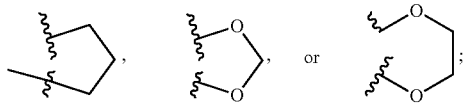

;

each $R^{19}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl;

each $R^{20}$ is independently selected from the group consisting of halo substituted aryl, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl, and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, in $R^1$, $R^2$, $R^3$, $R^4$, $R^5$, $R^6$, $R^{6a}$, $R^7$, $R^8$, $R^9$, $R^{10}$, $R^{11}$, $R^{12}$, $R^{13}$ and $R^{14}$;

is independently unsubstituted or substituted by 1 to 5 $R^{21}$ groups, wherein each $R^{21}$ group is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —O$R^{15}$, —C(O)$R^{15}$, —C(O)O$R^{15}$, —C(O)N($R^{15}$)($R^{16}$), —S$R^{15}$, —S(O)N($R^{15}$)($R^{16}$), —CH($R^{15}$)($R^{16}$), —S(O)$_2$N($R^{15}$)($R^{16}$), —C(=N$R^{15}$)$R^{16}$, —C(=NO$R^{15}$)$R^{16}$, —P(O)(O$R^{15}$)(O$R^{16}$), —N($R^{15}$)($R^{16}$), -alkyl-N($R^{15}$)($R^{16}$), —N($R^{15}$)C(O)$R^{16}$, —$CH_2$—N($R^{15}$)C(O)$R^{16}$, —$CH_2$—N($R^{15}$)C(O)N($R^{16}$)($R^{17}$), —$CH_2$—$R^{15}$; —$CH_2$N($R^{15}$)($R^{16}$), —N($R^{15}$)S(O)$R^{16}$, —N($R^{15}$)S(O)$_2R^{16}$, —$CH_2$—N($R^{15}$)S(O)$_2R^{16}$, —N($R^{15}$)S(O)$_2$N($R^{16}$)($R^{17}$), —N($R^{15}$)S(O)N($R^{16}$)($R^{17}$), —N($R^{15}$)C(O)N($R^{16}$)($R^{17}$), —$CH_2$—N($R^{15}$)C(O)N($R^{16}$)($R^{17}$), —N($R^{15}$)C(O)O$R^{16}$, —$CH_2$—N($R^{15}$)C(O)O$R^{16}$, —S(O)$R^{15}$, —$N_3$, —$NO_2$ and —S(O)$_2R^{15}$;

and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in $R^{21}$ is independently unsubstituted or substituted by 1 to 5 $R^{22}$ groups, wherein each $R^{22}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —$CF_3$, —CN, —$OR^{15}$, —$C(O)R^{15}$, —$C(O)OR^{15}$, -alkyl-C(O)$OR^{15}$, —$C(O)N(R^{15})(R^{16})$, —$SR^{15}$, —$S(O)N(R^{15})(R^{16})$, —$S(O)_2N(R^{15})(R^{16})$, —$C(=NR^{15})R^{16}$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$N_3$, —$NO_2$, —$S(O)R^{15}$ and —$S(O)_2R^{15}$;

or two $R^{21}$ or two $R^{22}$ moieties on adjacent carbons can be linked together to form

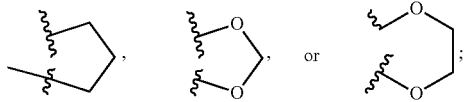

and when $R^{21}$ or $R^{22}$ are each independently selected from the group consisting of —$C(=NOR^{15})R^{16}$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$ and —$CH_2$—$N(R^{15})C(O)OR^{16}$, $R^{15}$ and $R^{16}$ together can be a $C_2$ to $C_4$ chain wherein, optionally, one, two or three ring carbons can be replaced by —C(O)— or —N(H)— and $R^{15}$ and $R^{16}$, together with the atoms to which they are attached, form a 5 to 7 membered ring, optionally substituted by from 1 to 5 groups $R^{23}$;

each $R^{23}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —$OR^{24}$, —$C(O)R^{24}$, —$C(O)OR^{24}$, —$C(O)N(R^{24})(R^{25})$, —$SR^{24}$, —$S(O)N(R^{24})(R^{25})$, —$S(O)_2N(R^{24})(R^{25})$, —$C(=NOR^{24})R^{25}$, —$(O)(OR^{24})(OR^{25})$, —$N(R^{24})(R^{25})$, -alkyl-$N(R^{24})(R^{25})$, —$N(R^{24})C(O)R^{25}$, —$CH_2$—$N(R^{24})C(O)R^{25}$, —$N(R^{24})S(O)R^{25}$, —$N(R^{24})S(O)_2R^{25}$, —$CH_2$—$N(R^{24})S(O)_2R^{25}$, —$N(R^{24})S(O)_2N(R^{25})(R^{26})$, —$N(R^{24})S(O)N(R^{25})(R^{26})$, —$N(R^{24})C(O)N(R^{25})(R^{26})$, —$CH_2$—$N(R^{24})C(O)N(R^{25})(R^{26})$, —$N(R^{24})C(O)OR^{25}$, —$CH_2$—$N(R^{24})C(O)OR^{25}$, —$S(O)R^{24}$ and —$S(O)_2R^{24}$; and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in $R^{23}$ are independently unsubstituted or substituted by 1 to 5 $R^{27}$ groups, wherein each group $R^{27}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —$CF_3$, —CN, —$OR^{24}$, —$C(O)R^{24}$, —$C(O)OR^{24}$, alkyl-C(O)$OR^{24}$, —$C(O)N(R^{24})(R^{25})$, —$SR^{24}$, —$S(O)N(R^{24})(R^{25})$, —$S(O)_2N(R^{24})(R^{25})$, —$C(=NOR^{24})R^{25}$, —$P(O)(OR^{24})(OR^{25})$, —$N(R^{24})(R^{25})$, -alkyl-$N(R^{24})(R^{25})$, —$N(R^{24})C(O)R^{25}$, —$CH_2$—$N(R^{24})C(O)R^{25}$, —$N(R^{24})S(O)R^{25}$, —$N(R^{24})S(O)_2R^{25}$, —$CH_2$—$N(R^{24})S(O)_2R^{25}$, —$N(R^{24})S(O)_2N(R^{25})(R^{26})$, —$N(R^{24})S(O)N(R^{25})(R^{26})$, —$N(R^{24})C(O)N(R^{25})(R^{26})$, —$CH_2$—$N(R^{24})C(O)N(R^{25})(R^{26})$, —$N(R^{24})C(O)OR^{25}$, —$CH_2$—$N(R^{24})C(O)OR^{25}$, —$S(O)R^{24}$ and —$S(O)_2R^{24}$;

each of $R^{24}$, $R^{25}$ and $R^{26}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, $R^{27}$-alkyl, $R^{27}$-arylalkyl, $R^{27}$-heteroarylalkyl, $R^{27}$-cycloalkylalkyl, $R^{27}$-heterocycloalkylalkyl, $R^{27}$-arylcycloalkylalkyl, $R^{27}$-heteroarylcycloalkylalkyl, $R^{27}$-arylheterocycloalkylalkyl, $R^{27}$-heteroarylheterocycloalkylalkyl, $R^{27}$-cycloalkyl, $R^{27}$-arylcycloalkyl, $R^{27}$-heteroarylcycloalkyl, $R^{27}$-heterocycloalkyl, $R^{27}$-arylheterocycloalkyl, $R^{27}$-heteroarylheterocycloalkyl, $R^{27}$-alkenyl, $R^{27}$-arylalkenyl, $R^{27}$-cycloalkenyl, $R^{27}$-arylcycloalkenyl, $R^{27}$-heteroarylcycloalkenyl, $R^{27}$-heterocycloalkenyl, $R^{27}$-arylheterocycloalkenyl, $R^{27}$-heteroarylheterocycloalkenyl, $R^{27}$-alkynyl, $R^{27}$-arylalkynyl, $R^{27}$-aryl, $R^{27}$-cycloalkylaryl, $R^{27}$-heterocycloalkylaryl, $R^{27}$-cycloalkenylaryl, $R^{27}$-heterocycloalkenylaryl, $R^{27}$-heteroaryl, $R^{27}$-cycloalkylheteroaryl, $R^{27}$-heterocycloalkylheteroaryl, $R^{27}$-cycloalkenylheteroaryl and $R^{27}$-heterocycloalkenylheteroaryl;

each $R^{27}$ is 1-5 substituents, each independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —NO$_2$, halo, —CF$_3$, —CN, alkyl-CN, —C(O)R$^{28}$, —C(O)OH, —C(O)OR$^{28}$, —C(O)NHR$^{29}$, —C(O)N(alkyl)$_2$, —C(O)N(alkyl)(aryl), —C(O)N(alkyl)(heteroaryl), —SR$^{28}$, —S(O)$_2$R$^{29}$, —S(O)N, —S(O)NH(alkyl), —S(O)N(alkyl)(alkyl), —S(O)NH(aryl), —S(O)$_2$NH$_2$, —S(O)$_2$NHR$^{28}$, —S(O)$_2$NH(aryl), —S(O)$_2$NH(heterocycloalkyl), —S(O)$_2$N(alkyl)$_2$, —S(O)$_2$N(alkyl)(aryl), —OH, —OR$^{29}$, —O-heterocycloalkyl, —O-cycloalkylalkyl, —O-heterocycloalkylalkyl, —NH$_2$, —NHR$^{29}$, —N(alkyl)$_2$, —N(arylalkyl)$_2$, —N(arylalkyl)(heteroarylalkyl), —NHC(O)R$^{29}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{29}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

each $R^{28}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl;

each $R^{29}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl each $R^{30}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —N(R$^{15}$)C(O)N(R$^{16}$)(R$^{17}$), —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), and —N(R$^{15}$)C(O)OR$^{16}$;

or two $R^{30}$ groups together with the carbon to which they are attached form a carbonyl; and each $R^{31}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —N(R$^{15}$)C(O)N(R$^{16}$)(R$^{17}$), —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), and —N(R$^{15}$)C(O)OR$^{16}$;

or $R^{31}$ forms a double bond with an adjacent ring atom or ring heteroatom of ring A (other than X);

or two $R^{31}$ groups together with the carbon to which they are attached form a carbonyl.

In other non-limiting embodiments, the present invention provides a compound, or a stereoisomer, tautomer, or a pharmaceutically acceptable salt, solvate, or prodrug thereof, according to any one of the following general formulae:

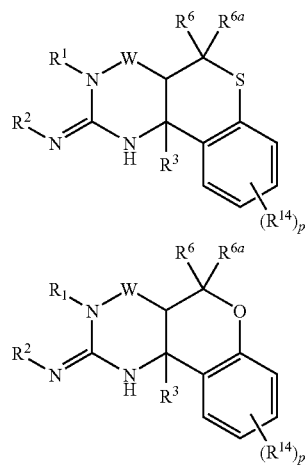

-continued

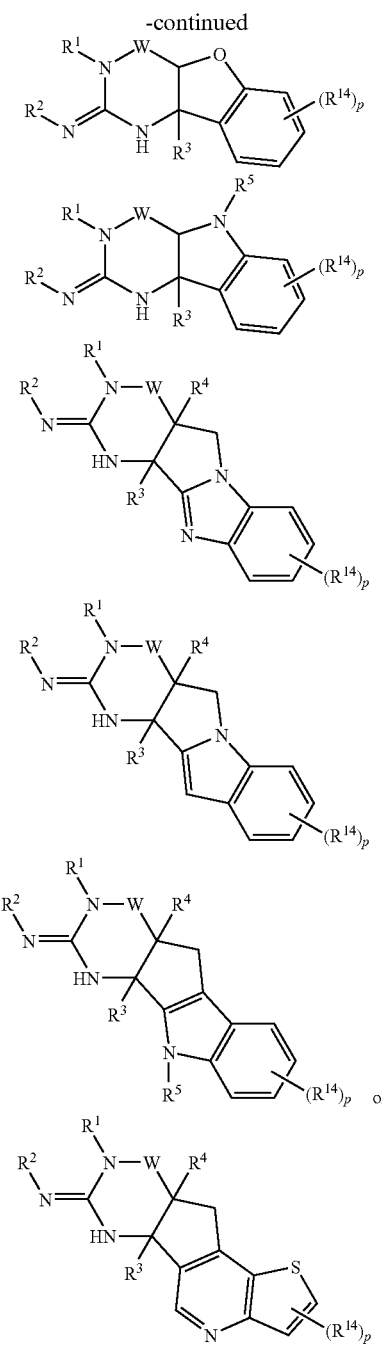

wherein p, q, $R^1$, $R^2$, $R^3$, $R^4$, $R^5$, $R^6$, W and $R^{14}$ are defined in Formula I.

In another embodiment, in Formula I, $R^1$ is alkyl. In another embodiment, $R^1$ is methyl.

In another embodiment, in Formula I, $R^2$ is H.

In another embodiment, in Formula I, $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula I, wherein $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula I, $R^3$ is arylalkyl, heteroarylalkyl, arylcycloalkyl, heteroarylcycloalkyl, arylalkenyl, arylalkynyl, aryl or heteroaryl.

In another embodiment, in Formula I, $R^3$ is heteroaryl or aryl.

In another embodiment, in Formula I, $R^3$ is

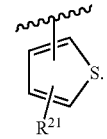

In another embodiment, in Formula I, $R^{21}$ is —CN.

In another embodiment, the invention provides compounds of Formula I wherein $R^3$ is

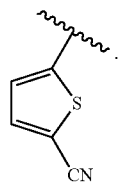

In another embodiment, in Formula I, W is C=O.

In another embodiment, in Formula I, $R^4$ is H, alkyl or halo.

In another embodiment, in Formula I, Z is a bond.

In another embodiment, in Formula I, ring A together with V and X forms a heteroarylene.

In another embodiment, in Formula I, ring A together with V and X forms a moiety selected from the group consisting of:

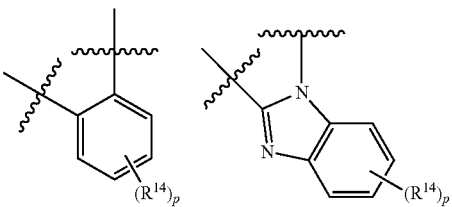

-continued

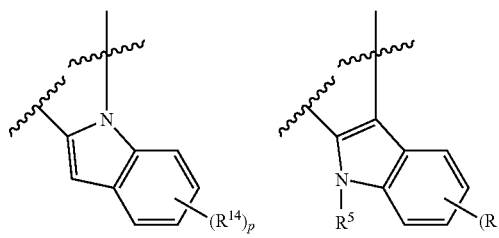

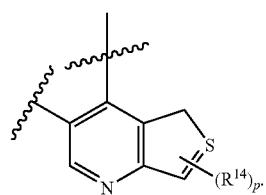

In another embodiment, in Formula I, $R^{14}$ is alkyl or halo.

In another embodiment, in Formula I, wherein $R^{14}$ is methyl.

In another embodiment, in Formula I, $R^{14}$ is F.

In another embodiment, in Formula I, X is a carbon or nitrogen

In another embodiment, in Formula I, Y is $-C(R^6)(R^{6a})-$. In another embodiment, $R^6$ is H and $R^{6a}$ is H.

In another embodiment, in Formula I, Z is a bond and Y is $-C(R^6)(R^{6a})-$.

In another embodiment, in Formula I, Z is a bond; Y is $-C(R^6)(R^{6a})-$; and ring A together with V and X forms a moiety selected from:

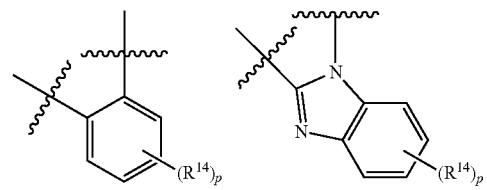

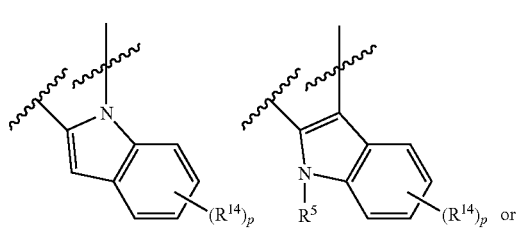

In one such embodiment, Y is $-CH_2-$.

In another embodiment, in Formula I, V—X is

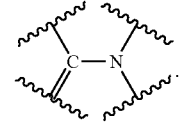

In another embodiment, in Formula I, V=X is

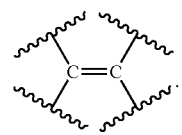

In another embodiment, in Formula I, each of $R^{15}$, $R^{16}$ and $R^{17}$ is independently selected from the group consisting of

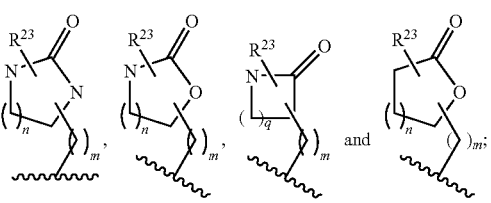

wherein each $R^{23}$ independently numbers 0 to 5 substituents, each $R^{23}$ is independently as defined above, each m is, independently, 0 to 6, each n is, independently, 0 to 5, and each q is independently 1 to 5.

In another embodiment, in Formula I, ring A together with V and X forms a moiety selected from:

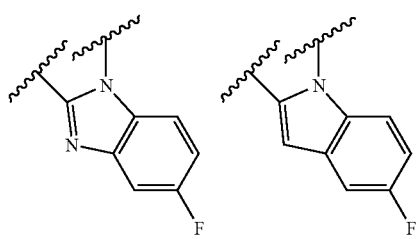

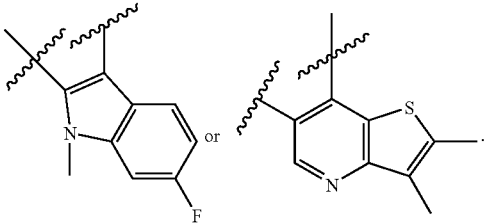

Non-limiting examples of compounds of Formula I include the following:

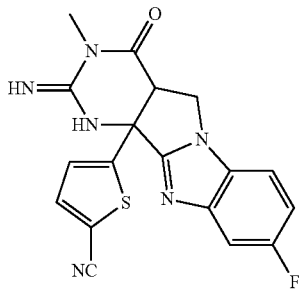

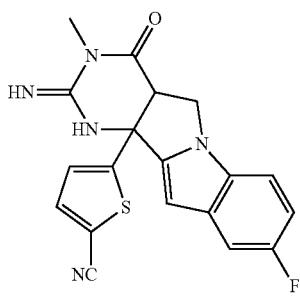

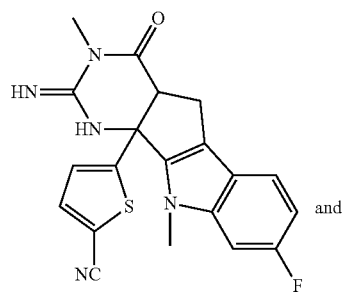

and

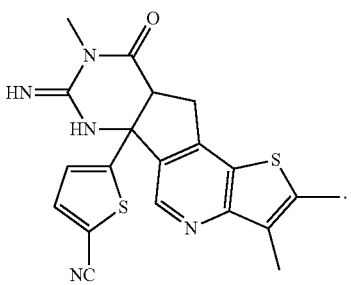

It is noted that the carbons of formula I may be replaced with 1 to 3 silicon atoms so long as all valency requirements are satisfied.

For the various embodiments of the present invention described herein, it shall be understood that any variable of a structural formula not explicitly defined therein is as defined in Formula (I) above.

In another embodiment, the present invention provides a compound, or a stereoisomer, tautomer, or pharmaceutically acceptable salt or solvate thereof, having the general structure shown in Formula (II):

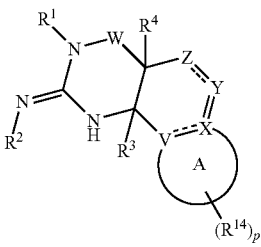

wherein $R^1$, $R^2$, $R^3$, $R^4$, W, Z, Y, X, V, ring A, p, and each $R^{14}$ is selected independently of each other and wherein:

W is —S(O)—, —S(O)$_2$—, or —O—, and $R^1$, $R^2$, $R^3$, $R^4$, Z, X, Y, V, ring A, $R^{14}$, and p are as defined in Formula I.

In another embodiment, in Formula (II), W is —S(O)— or —S(O)$_2$—.

In another embodiment, in Formula (II), W is —O—.

In another embodiment, in Formula (II), V is a carbon atom and V, X, and ring A, and —(R$^{14}$)$_p$ form

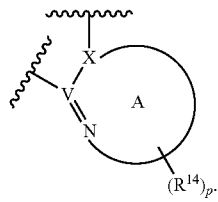

In another embodiment, in Formula (II), V is a carbon atom and V, X, and ring A, and —(R$^{14}$)$_p$ form

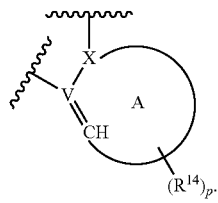

In another embodiment, in Formula (II), V is a carbon atom and V, X, and ring A, and —(R$^{14}$)$_p$ form

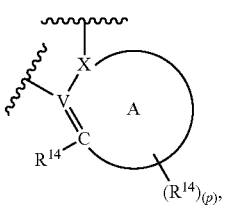

and p=0-4.

In another embodiment, in Formula (II), $R^1$ is alkyl.
In another embodiment, in Formula (II), $R^1$ is methyl.
In another embodiment, in Formula (II), $R^2$ is H.
In another embodiment, in Formula (II), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (II), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (II), $R^3$ is arylalkyl, heteroarylalkyl, arylcycloalkyl, heteroarylcycloalkyl, arylalkenyl, arylalkynyl, aryl or heteroaryl.

In another embodiment, in Formula (II), $R^3$ is heteroaryl or aryl.

In another embodiment, in Formula (II), $R^3$ is

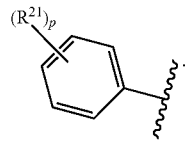

In another embodiment, in Formula (II), $R^3$ is

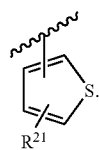

In another embodiment, in Formula (II), $R^3$ is

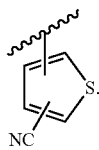

In another embodiment, in Formula (II), $R^3$ is

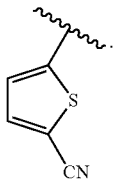

In another embodiment, in Formula (I), $R^4$ is H.
In another embodiment, in Formula (II), $R^4$ is alkyl.
In another embodiment, in Formula (II), $R^4$ is halo.
In another embodiment, in Formula (II), $R^4$ is alkyl.
In another embodiment, in Formula (II), $R^4$ is halo.
In another embodiment, in Formula (II), p is 0 (and $R^{14}$ is not present).
In another embodiment, in Formula (II), p is 1.
In another embodiment, in Formula (II), p is 2.
In another embodiment, in Formula (II), p is 3.
In another embodiment, in Formula (II), p is 4.
In another embodiment, in Formula (II), p is 5.
In another embodiment, in Formula (II), p is 2-5 and at least two groups $R^{14}$ are bound to the same ring atom.
In another embodiment, in Formula (II), at least one group $R^{14}$ is H.
In another embodiment, in Formula (II), at least one group $R^{14}$ is alkyl.
In another embodiment, in Formula (II), at least one group $R^{14}$ is arylalkyl.
In another embodiment, in Formula (II), at least one group $R^{14}$ is heteroarylalkyl.
In another embodiment, in Formula (II), at least one group $R^{14}$ is cycloalkylalkyl.
In another embodiment, in Formula (II), at least one group $R^{14}$ is heterocycloalkylalkyl.
In another embodiment, in Formula (II), at least one group $R^{14}$ is arylcycloalkylalkyl.
In another embodiment, in Formula (II), at least one group $R^{14}$ is heteroarylcycloalkylalkyl.
In another embodiment, in Formula (II), at least one group $R^{14}$ is arylheterocycloalkylalkyl.
In another embodiment, in Formula (II), at least one group $R^{14}$ is heteroarylheterocycloalkylalkyl.
In another embodiment, in Formula (II), at least one group $R^{14}$ is cycloalkyl.
In another embodiment, in Formula (II), at least one group $R^{14}$ is arylcycloalkyl.
In another embodiment, in Formula (II), at least one group $R^{14}$ is heteroarylcycloalkyl.
In another embodiment, in Formula (II), at least one group $R^{14}$ is heterocycloalkyl.
In another embodiment, in Formula (II), at least one group $R^{14}$ is arylheterocycloalkyl.
In another embodiment, in Formula (II), at least one group $R^{14}$ is heteroarylheterocycloalkyl.
In another embodiment, in Formula (II), at least one group $R^{14}$ is alkenyl.
In another embodiment, in Formula (II), at least one group $R^{14}$ is arylalkenyl.
In another embodiment, in Formula (II), at least one group $R^{14}$ is cycloalkenyl.
In another embodiment, in Formula (II), at least one group $R^{14}$ is arylcycloalkenyl.
In another embodiment, in Formula (II), at least one group $R^{14}$ is heteroarylcycloalkenyl.
In another embodiment, in Formula (II), at least one group $R^{14}$ is heterocycloalkenyl.
In another embodiment, in Formula (II), at least one group $R^{14}$ is arylheterocycloalkenyl.
In another embodiment, in Formula (II), at least one group $R^{14}$ is heteroarylheterocycloalkenyl.
In another embodiment, in Formula (II), at least one group $R^{14}$ is alkynyl.
In another embodiment, in Formula (II), at least one group $R^{14}$ is arylalkynyl.
In another embodiment, in Formula (II), at least one group $R^{14}$ is aryl.
In another embodiment, in Formula (II), at least one group $R^{14}$ is cycloalkylaryl.

In another embodiment, in Formula (II), at least one group $R^{14}$ is heterocycloalkylaryl.

In another embodiment, in Formula (II), at least one group $R^{14}$ is cycloalkenylaryl.

In another embodiment, in Formula (II), at least one group $R^{14}$ is heterocycloalkenylaryl.

In another embodiment, in Formula (II), at least one group $R^{14}$ is heteroaryl.

In another embodiment, in Formula (II), at least one group $R^{14}$ is cycloalkylheteroaryl.

In another embodiment, in Formula (II), at least one group $R^{14}$ is heterocycloalkylheteroaryl.

In another embodiment, in Formula (II), at least one group $R^{14}$ is cycloalkenylheteroaryl.

In another embodiment, in Formula (II), at least one group $R^{14}$ is heterocycloalkenylheteroaryl.

In another embodiment, in Formula (II), at least one group $R^{14}$ is halo.

In another embodiment, in Formula (II), at least one group $R^{14}$ is $-CH_2-O-Si(R^9)(R^{10})(R^{19})$.

In another embodiment, in Formula (II), at least one group $R^{14}$ is $-N(R^{15})C(O)N(R^{16})(R^{17})$.

In another embodiment, in Formula (II), at least one group $R^{14}$ is $-CN$.

In another embodiment, in Formula (II), at least one group $R^{14}$ is $-OR^{15}$.

In another embodiment, in Formula (II), at least one group $R^{14}$ is $-C(O)R^{15}$.

In another embodiment, in Formula (II), at least one group $R^{14}$ is $-C(O)OR^{15}$. In another embodiment, in Formula (II), at least one group $R^{14}$ is $-C(O)N(R^{15})(R^{16})$.

In another embodiment, in Formula (II), at least one group $R^{14}$ is $-SR^{15}$ In another embodiment, in Formula (II), at least one group $R^{14}$ is $-S(O)N(R^{15})(R^{16})$.

In another embodiment, in Formula (II), at least one group $R^{14}$ is $-S(O)_2N(R^{15})(R^{16})$.

In another embodiment, in Formula (II), at least one group $R^{14}$ is $-C(=NOR^{15})R^{16}$.

In another embodiment, in Formula (II), at least one group $R^{14}$ is $-P(O)(OR^{15})(OR^{16})$.

In another embodiment, in Formula (II), at least one group $R^{14}$ is $-N(R^{15})(R^{16})$.

In another embodiment, in Formula (II), at least one group $R^{14}$ is $-N(R^{15})C(O)R^{16}$.

In another embodiment, in Formula (II), at least one group $R^{14}$ is $-N(R^{15})S(O)R^{16}$.

In another embodiment, in Formula (II), at least one group $R^{14}$ is $-N(R^{15})S(O)_2R^{16}$.

In another embodiment, in Formula (II), at least one group $R^{14}$ is $-N(R^{15})S(O)_2N(R^{16})(R^{17})$.

In another embodiment, in Formula (II), at least one group $R^{14}$ is $-N(R^{15})S(O)N(R^{16})(R^{17})$.

In another embodiment, in Formula (II), at least one group $R^{14}$ is $-N(R^{15})C(O)N(R^{16})(R^{17})$.

In another embodiment, in Formula (II), at least one group $R^{14}$ is $-N(R^{15})C(O)OR^{16}$.

In another embodiment, the present invention provides a compound, or a stereoisomer, tautomer, or pharmaceutically acceptable salt or solvate thereof, having the general structure shown in Formula (III):

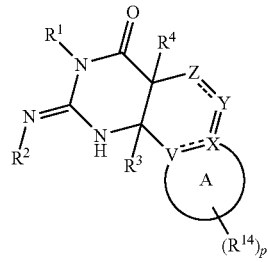

(III)

wherein $R^1$, $R^2$, $R^3$, $R^4$, Z, Y, X, V, Ring A, p, and Each $R^{14}$ is selected independently of each other and wherein:

ring A forms a mono or multicyclic 4 to 12 membered heteroarylene ring, and $R^1$, $R^2$, $R^3$, $R^4$, Z, X, Y, V, $R^{14}$, and p are as defined in Formula I.

In another embodiment, in Formula (III), ring A together with V and X forms a monocyclic 4 to 12 membered heteroarylene.

In another embodiment, in Formula (III), ring A together with V and X forms a monocyclic heteroarylene ring.

In another embodiment, in Formula (III), ring A together with V and X forms a multicyclic heteroarylene ring.

In another embodiment, in Formula (III), ring A together with V and X forms a bicyclic heteroarylene ring.

In another embodiment, in Formula (III), ring A together with V and X forms a 5-6-membered monocyclic heteroarylene ring having from 1 to 4 ring heteroatoms independently selected from the group consisting of N, O, and S.

In another embodiment, in Formula (III), ring A together with V and X forms a 5-6-membered monocyclic heteroarylene ring having from 1 ring heteroatom independently selected from the group consisting of N, O, and S.

In another embodiment, in Formula (III), ring A together with V and X forms a 5-6-membered monocyclic heteroarylene ring having from 2 ring heteroatoms independently selected from the group consisting of N, O, and S.

In another embodiment, in Formula (III), ring A together with V and X forms a 5-6-membered monocyclic heteroarylene ring having from 3 ring heteroatoms independently selected from the group consisting of N, O, and S.

In another embodiment, in Formula (III), V is a carbon atom and V, X, and ring A, and $-(R^{14})_p$ form

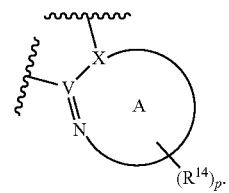

In another embodiment, in Formula (III), V is a carbon atom and V, X, and ring A, and $-(R^{14})_p$ form

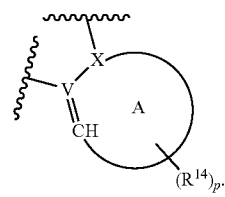

In another embodiment, in Formula (III), V is a carbon atom and V, X, and ring A, and —(R$^{14}$)$_p$ form

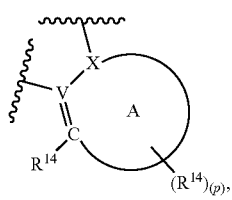

and p=0-4.

In another embodiment, in Formula (III), —V—X— is

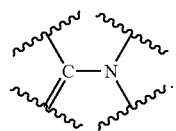

In another embodiment, in Formula (III), —V═X— is

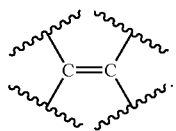

In another embodiment, in Formula (III), ring A together with V and X forms a pyrazolyl, furanyl, theinyl, isoxazolyl, isothiazolyl, oxazolyl, thiazolyl, pyrazolyl, furazanyl, pyrrolyl, pyrazolyl, triazolyl, thiadiazolyl, pyridyl, pyrimidinyl, pyridonyl, imidazolyl, or pyrazinyl ring.

In another embodiment, in Formula (III), ring A together with V and X and —(R$^{14}$)$_p$ forms a group selected from:

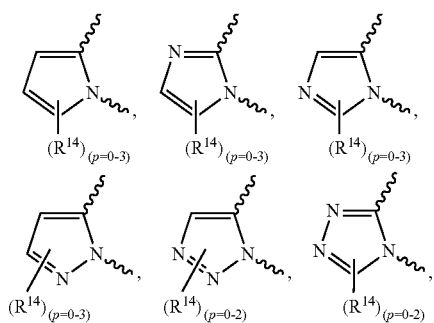

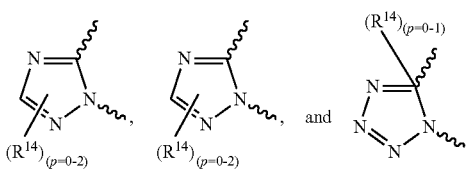

In another embodiment, in Formula (III), ring A together with V and X forms an 8-10-membered bicyclic heteroarylene ring having 1 or more ring heteroatoms independently selected from the group consisting of N, O, and S.

In another embodiment, in Formula (III), ring A together with V and X forms a quinoxalinyl, phthalazinyl, oxindolyl, imidazopyridinyl, imidazothiazolyl, benzofurazanyl, indolyl, azaindolyl, benzimidazolyl, benzothienyl, quinolinyl, quinazolinyl, isoquinolinyl, triazinyl, benzothiazoly, thieonpyridyl, thienopyrimidyl, imidazolpyridyl, or a pyrrolopyridyl ring.

In another embodiment, in Formula (III), R$^1$ is alkyl.

In another embodiment, in Formula (III), R$^1$ is methyl.

In another embodiment, in Formula (III), R$^2$ is H.

In another embodiment, in Formula (III), R$^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III), R$^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III), R$^3$ is arylalkyl, heteroarylalkyl, arylcycloalkyl, heteroarylcycloalkyl, arylalkenyl, arylalkynyl, aryl or heteroaryl.

In another embodiment, in Formula (III), R$^3$ is heteroaryl or aryl.

In another embodiment, in Formula (III), R$^3$ is

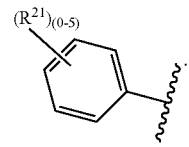

In another embodiment, in Formula (III), R³ is

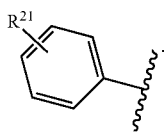

In another embodiment, in Formula (III), R³ is

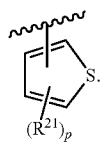

In another embodiment, in Formula (III), R³ is

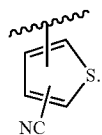

In another embodiment, in Formula (III), R³ is

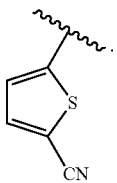

In another embodiment, in Formula (III), R⁴ is H.
In another embodiment, in Formula (III), R⁴ is alkyl.
In another embodiment, in Formula (III), R⁴ is halo.
In another embodiment, in Formula (III), p is 0 (and R¹⁴ is not present).
In another embodiment, in Formula (III), p is 1.
In another embodiment, in Formula (III), p is 2.
In another embodiment, in Formula (III), p is 3.
In another embodiment, in Formula (III), p is 4.
In another embodiment, in Formula (III), p is 5.
In another embodiment, in Formula (III), p is 2-5 and at least two groups R¹⁴ are bound to the same ring atom.
In another embodiment, in Formula (III), at least one group R¹⁴ is H.
In another embodiment, in Formula (III), at least one group R¹⁴ is alkyl.
In another embodiment, in Formula (III), at least one group R¹⁴ is arylalkyl.
In another embodiment, in Formula (III), at least one group R¹⁴ is heteroarylalkyl.
In another embodiment, in Formula (III), at least one group R¹⁴ is cycloalkylalkyl.
In another embodiment, in Formula (III), at least one group R¹⁴ is heterocycloalkylalkyl.
In another embodiment, in Formula (III), at least one group R¹⁴ is arylcycloalkylalkyl.
In another embodiment, in Formula (III), at least one group R¹⁴ is heteroarylcycloalkylalkyl.
In another embodiment, in Formula (III), at least one group R¹⁴ is arylheterocycloalkylalkyl.
In another embodiment, in Formula (III), at least one group R¹⁴ is heteroarylheterocycloalkylalkyl.
In another embodiment, in Formula (III), at least one group R¹⁴ is cycloalkyl.
In another embodiment, in Formula (III), at least one group R¹⁴ is arylcycloalkyl.
In another embodiment, in Formula (III), at least one group R¹⁴ is heteroarylcycloalkyl.
In another embodiment, in Formula (III), at least one group R¹⁴ is heterocycloalkyl.
In another embodiment, in Formula (III), at least one group R¹⁴ is arylheterocycloalkyl.
In another embodiment, in Formula (III), at least one group R¹⁴ is heteroarylheterocycloalkyl.
In another embodiment, in Formula (III), at least one group R¹⁴ is alkenyl.
In another embodiment, in Formula (III), at least one group R¹⁴ is arylalkenyl.
In another embodiment, in Formula (III), at least one group R¹⁴ is cycloalkenyl.
In another embodiment, in Formula (III), at least one group R¹⁴ is arylcycloalkenyl.
In another embodiment, in Formula (III), at least one group R¹⁴ is heteroarylcycloalkenyl.
In another embodiment, in Formula (III), at least one group R¹⁴ is heterocycloalkenyl.
In another embodiment, in Formula (III), at least one group R¹⁴ is arylheterocycloalkenyl.
In another embodiment, in Formula (III), at least one group R¹⁴ is heteroarylheterocycloalkenyl.
In another embodiment, in Formula (III), at least one group R¹⁴ is alkynyl.
In another embodiment, in Formula (III), at least one group R¹⁴ is arylalkynyl.
In another embodiment, in Formula (III), at least one group R¹⁴ is aryl.
In another embodiment, in Formula (III), at least one group R¹⁴ is cycloalkylaryl.
In another embodiment, in Formula (III), at least one group R¹⁴ is heterocycloalkylaryl.
In another embodiment, in Formula (III), at least one group R¹⁴ is cycloalkenylaryl.
In another embodiment, in Formula (III), at least one group R¹⁴ is heterocycloalkenylaryl.
In another embodiment, in Formula (III), at least one group R¹⁴ is heteroaryl.
In another embodiment, in Formula (III), at least one group R¹⁴ is cycloalkylheteroaryl.
In another embodiment, in Formula (III), at least one group R¹⁴ is heterocycloalkylheteroaryl.
In another embodiment, in Formula (III), at least one group R¹⁴ is cycloalkenylheteroaryl.
In another embodiment, in Formula (III), at least one group R¹⁴ is heterocycloalkenylheteroaryl.
In another embodiment, in Formula (III), at least one group R¹⁴ is halo.
In another embodiment, in Formula (III), at least one group R¹⁴ is —CH₂—O—Si(R⁹)(R¹⁰)(R¹⁹).
In another embodiment, in Formula (III), at least one group R¹⁴ is —N(R¹⁵)C(O)N(R¹⁶)(R¹⁷).
In another embodiment, in Formula (III), at least one group R¹⁴ is —CN.
In another embodiment, in Formula (III), at least one group R¹⁴ is —OR¹⁵.

In another embodiment, in Formula (III), at least one group $R^{14}$ is $-C(O)R^{15}$.

In another embodiment, in Formula (III), at least one group $R^{14}$ is $-C(O)OR^{15}$.

In another embodiment, in Formula (III), at least one group $R^{14}$ is $-C(O)N(R^{15})(R^{16})$.

In another embodiment, in Formula (III), at least one group $R^{14}$ is $-SR^{15}$.

In another embodiment, in Formula (II), at least one group $R^{14}$ is $-S(O)N(R^{15})(R^{16})$.

In another embodiment, in Formula (III), at least one group $R^{14}$ is $-S(O)_2N(R^{15})(R^{16})$.

In another embodiment, in Formula (III), at least one group $R^{14}$ is $-C(=_NOR^{15})R^{16}$.

In another embodiment, in Formula (III), at least one group $R^{14}$ is $-P(O)(OR^{15})(OR^{16})$.

In another embodiment, in Formula (III), at least one group $R^{14}$ is $-N(R^{15})(R^{16})$.

In another embodiment, in Formula (III), at least one group $R^{14}$ is $-N(R^{15})C(O)R^{16}$.

In another embodiment, in Formula (III), at least one group $R^{14}$ is $-N(R^{15})S(O)R^{16}$.

In another embodiment, in Formula (III), at least one group $R^{14}$ is $-N(R^{15})S(O)_2R^{16}$.

In another embodiment, in Formula (III), at least one group $R^{14}$ is $-N(R^{15})S(O)_2N(R^{16})(R^{17})$.

In another embodiment, in Formula (III), at least one group $R^{14}$ is $-N(R^{15})S(O)N(R^{16})(R^{17})$.

In another embodiment, in Formula (III), at least one group $R^{14}$ is $-N(R^{15})C(O)N(R^{16})(R^{17})$.

In another embodiment, in Formula (III), at least one group $R^{14}$ is $-N(R^{15})C(O)OR^{16}$.

In another embodiment, the present invention provides a compound, or a stereoisomer, tautomer, or pharmaceutically acceptable salt or solvate thereof, having the general structure shown in Formula (III.a.):

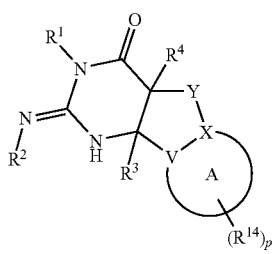

(III.a.)

wherein $R^1$, $R^2$, $R^3$, $R^4$, Y, X, V, ring A, p, and each $R^{14}$ is selected independently of each other and wherein:

ring A forms a mono or multicyclic 4 to 12 membered heteroarylene ring, and $R^1$, $R^2$, $R^3$, $R^4$, X, Y, V, A, $R^{14}$, and p are as defined in Formula I.

In another embodiment, in Formula (III.a.), ring A together with V and X forms a monocyclic 4 to 12 membered heteroarylene.

In another embodiment, in Formula (III.a.), ring A together with V and X forms a monocyclic heteroarylene ring.

In another embodiment, in Formula (III.a.), ring A together with V and X forms a multicyclic heteroarylene ring.

In another embodiment, in Formula (III.a.), ring A together with V and X forms a bicyclic heteroarylene ring.

In another embodiment, in Formula (III.a.), ring A together with V and X forms a 5-6-membered monocyclic heteroarylene ring having from 1 to 4 ring heteroatoms independently selected from the group consisting of N, O, and S.

In another embodiment, in Formula (III.a.), ring A together with V and X forms a 5-6-membered monocyclic heteroarylene ring having from 1 ring heteroatom independently selected from the group consisting of N, O, and S.

In another embodiment, in Formula (III.a.), ring A together with V and X forms a 5-6-membered monocyclic heteroarylene ring having from 2 ring heteroatoms independently selected from the group consisting of N, O, and S.

In another embodiment, in Formula (III.a.), ring A together with V and X forms a 5-6-membered monocyclic heteroarylene ring having from 3 ring heteroatoms independently selected from the group consisting of N, O, and S.

In another embodiment, in Formula (III.a.), V is a carbon atom and V, X, and ring A, and $-(R^{14})_p$ form

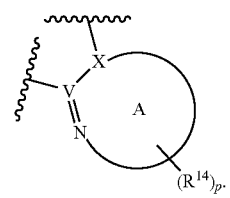

In another embodiment, in Formula (III.a.), V is a carbon atom and V, X, and ring A, and $-(R^{14})_p$ form

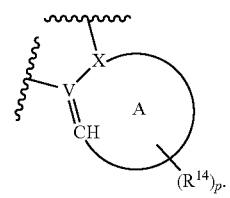

In another embodiment, in Formula (III.a.), V is a carbon atom and V, X, and ring A, and $-(R^{14})_p$ form

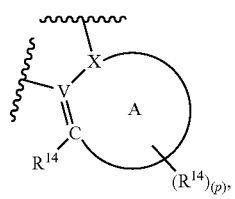

and p=0-4.

In another embodiment, in Formula (III.a), $-V-X-$ is

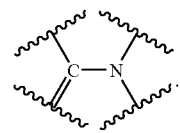

In another embodiment, in Formula (III.a), —V=X— is

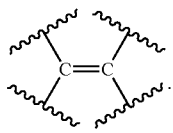

In another embodiment, in Formula (III.a), ring A together with V and X forms a pyrazolyl, furanyl, theinyl, isoxazolyl, isothiazolyl, oxazolyl, thiazolyl, pyrazolyl, furazanyl, pyrrolyl, pyrazolyl, triazolyl, thiadiazolyl, pyridyl, pyrimidinyl, pyridonyl, imidazolyl, or pyrazinyl ring.

In another embodiment, in Formula (III.a), ring A and —$(R^{14})_p$ is selected from the group consisting of:

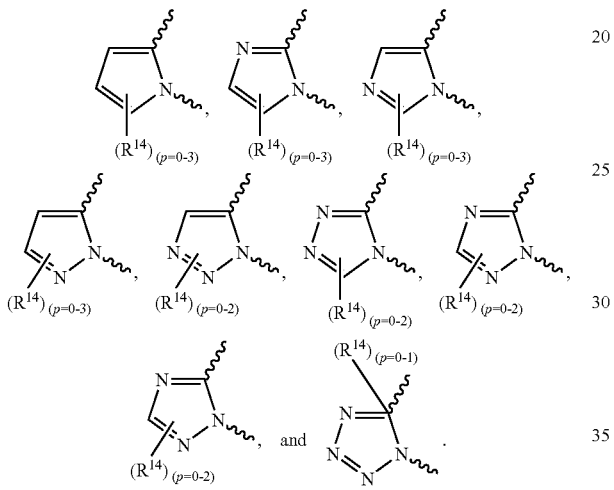

In another embodiment, in Formula (III.a), ring A together with V and X forms an 8-10-membered bicyclic heteroarylene ring having 1 or more ring heteroatoms independently selected from the group consisting of N, O, and S.

In another embodiment, in Formula (III.a), ring A together with V and X forms a quinoxalinyl, phthalazinyl, oxindolyl, imidazopyridinyl, imidazothiazolyl, benzofurazanyl, indolyl, azaindolyl, benzimidazolyl, benzothienyl, quinolinyl, quinazolinyl, isoquinolinyl, triazinyl, benzothiazoly, thieonpyridyl, thienopyrimidyl, imidazolpyridyl, or a pyrrolopyridyl ring.

In another embodiment, in Formula (III.a), $R^1$ is alkyl.
In another embodiment, in Formula (III.a), $R^1$ is methyl.
In another embodiment, in Formula (III.a), $R^2$ is H.
In another embodiment, in Formula (III.a), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.a), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.a), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.a), $R^3$ is heteroaryl or aryl.

In another embodiment, in Formula (III.a), $R^3$ is

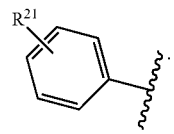

In another embodiment, in Formula (III.a), $R^3$ is

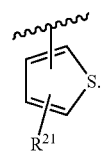

In another embodiment, in Formula (III.a), $R^3$ is

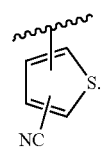

In another embodiment, in Formula (III.a), $R^3$ is

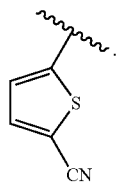

In another embodiment, in Formula (III.a), $R^4$ is H.
In another embodiment, in Formula (III.a), $R^4$ is alkyl.
In another embodiment, in Formula (III.a), $R^4$ is halo.
In another embodiment, in Formula (III.a), p is 0 (and $R^{14}$) is not present.
In another embodiment, in Formula (III.a), p is 1.
In another embodiment, in Formula (III.a), p is 2.
In another embodiment, in Formula (III.a), p is 3.
In another embodiment, in Formula (III.a), p is 4.
In another embodiment, in Formula (III.a), p is 5.
In another embodiment, in Formula (III.a), p is 2-5 and at least two groups $R^{14}$ are bound to the same ring atom.
In another embodiment, in Formula (III.a), at least one group $R^{14}$ is H.

In another embodiment, in Formula (III.a.), at least one group $R^{14}$ is alkyl.

In another embodiment, in Formula (III.a.), at least one group $R^{14}$ is arylalkyl.

In another embodiment, in Formula (III.a.), at least one group $R^{14}$ is heteroarylalkyl.

In another embodiment, in Formula (III.a.), at least one group $R^{14}$ is cycloalkylalkyl.

In another embodiment, in Formula (III.a.), at least one group $R^{14}$ is heterocycloalkylalkyl.

In another embodiment, in Formula (III.a.), at least one group $R^{14}$ is arylcycloalkylalkyl.

In another embodiment, in Formula (III.a.), at least one group $R^{14}$ is heteroarylcycloalkylalkyl.

In another embodiment, in Formula (III.a.), at least one group $R^{14}$ is arylheterocycloalkylalkyl.

In another embodiment, in Formula (III.a.), at least one group $R^{14}$ is heteroarylheterocycloalkylalkyl.

In another embodiment, in Formula (III.a.), at least one group $R^{14}$ is cycloalkyl.

In another embodiment, in Formula (III.a.), at least one group $R^{14}$ is arylcycloalkyl.

In another embodiment, in Formula (III.a.), at least one group $R^{14}$ is heteroarylcycloalkyl.

In another embodiment, in Formula (III.a.), at least one group $R^{14}$ is heterocycloalkyl.

In another embodiment, in Formula (III.a.), at least one group $R^{14}$ is arylheterocycloalkyl.

In another embodiment, in Formula (III.a.), at least one group $R^{14}$ is heteroarylheterocycloalkyl.

In another embodiment, in Formula (III.a.), at least one group $R^{14}$ is alkenyl.

In another embodiment, in Formula (III.a.), at least one group $R^{14}$ is arylalkenyl.

In another embodiment, in Formula (III.a.), at least one group $R^{14}$ is cycloalkenyl.

In another embodiment, in Formula (III.a.), at least one group $R^{14}$ is arylcycloalkenyl.

In another embodiment, in Formula (III.a.), at least one group $R^{14}$ is heteroarylcycloalkenyl.

In another embodiment, in Formula (III.a.), at least one group $R^{14}$ is heterocycloalkenyl.

In another embodiment, in Formula (III.a.), at least one group $R^{14}$ is arylheterocycloalkenyl.

In another embodiment, in Formula (III.a.), at least one group $R^{14}$ is heteroarylheterocycloalkenyl.

In another embodiment, in Formula (III.a.), at least one group $R^{14}$ is alkynyl.

In another embodiment, in Formula (III.a.), at least one group $R^{14}$ is arylalkynyl.

In another embodiment, in Formula (III.a.), at least one group $R^{14}$ is aryl.

In another embodiment, in Formula (III.a.), at least one group $R^{14}$ is cycloalkylaryl.

In another embodiment, in Formula (III.a.), at least one group $R^{14}$ is heterocycloalkylaryl.

In another embodiment, in Formula (III.a.), at least one group $R^{14}$ is cycloalkenylaryl.

In another embodiment, in Formula (III.a.), at least one group $R^{14}$ is heterocycloalkenylaryl.

In another embodiment, in Formula (III.a.), at least one group $R^{14}$ is heteroaryl.

In another embodiment, in Formula (III.a.), at least one group $R^{14}$ is cycloalkylheteroaryl.

In another embodiment, in Formula (III.a.), at least one group $R^{14}$ is heterocycloalkylheteroaryl.

In another embodiment, in Formula (III.a.), at least one group $R^{14}$ is cycloalkenylheteroaryl.

In another embodiment, in Formula (III.a.), at least one group $R^{14}$ is heterocycloalkenylheteroaryl.

In another embodiment, in Formula (III.a.), at least one group $R^{14}$ is halo.

In another embodiment, in Formula (III.a.), at least one group $R^{14}$ is —$CH_2$—O—Si($R^9$)($R^{10}$)($R^{19}$).

In another embodiment, in Formula (III.a.), at least one group $R^{14}$ is —N($R^{15}$)C(O)N($R^{16}$)($R^{17}$).

In another embodiment, in Formula (III.a.), at least one group $R^{14}$ is —CN.

In another embodiment, in Formula (III.a.), at least one group $R^{14}$ is —$OR^{15}$.

In another embodiment, in Formula (III.a.), at least one group $R^{14}$ is —C(O)$R^{15}$.

In another embodiment, in Formula (III.a.), at least one group $R^{14}$ is —C(O)O$R^{15}$.

In another embodiment, in Formula (III.a.), at least one group $R^{14}$ is —C(O)N($R^{15}$)($R^{16}$).

In another embodiment, in Formula (III.a.), at least one group $R^{14}$ is —$SR^{15}$.

In another embodiment, in Formula (III.a.), at least one group $R^{14}$ is —S(O)N($R^{15}$)($R^{16}$).

In another embodiment, in Formula (III.a.), at least one group $R^{14}$ is —S(O)$_2$N($R^{15}$)($R^{16}$).

In another embodiment, in Formula (III.a.), at least one group $R^{14}$ is —C(=NO$R^{15}$)$R^{16}$.

In another embodiment, in Formula (III.a.), at least one group $R^{14}$ is —P(O)(O$R^{15}$)(O$R^{16}$).

In another embodiment, in Formula (III.a.), at least one group $R^{14}$ is —N($R^{15}$)($R^{16}$).

In another embodiment, in Formula (III.a.), at least one group $R^{14}$ is —N($R^{15}$)C(O)$R^{16}$.

In another embodiment, in Formula (III.a.), at least one group $R^{14}$ is —N($R^{15}$)S(O)$R^{16}$.

In another embodiment, in Formula (III.a.), at least one group $R^{14}$ is —N($R^{15}$)S(O)$_2R^{16}$.

In another embodiment, in Formula (III.a.), at least one group $R^{14}$ is —N($R^{15}$)S(O)$_2$N($R^{16}$)($R^{17}$).

In another embodiment, in Formula (III.a.), at least one group $R^{14}$ is —N($R^{15}$)S(O)N($R^{16}$)($R^{17}$).

In another embodiment, in Formula (III.a.), at least one group $R^{14}$ is —N($R^{15}$)C(O)N($R^{16}$)($R^{17}$).

In another embodiment, in Formula (III.a.), at least one group $R^{14}$ is —N($R^{15}$)C(O)O$R^{16}$.

In another embodiment, the present invention provides a compound, or a stereoisomer, tautomer, or pharmaceutically acceptable salt or solvate thereof, having the general structure shown in Formula (III.c.):

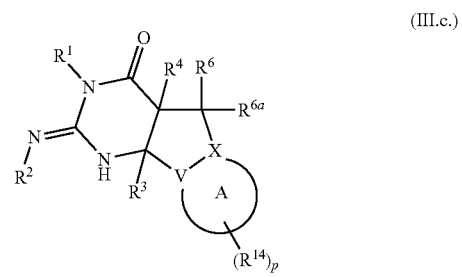

(III.c.)

wherein $R^1$, $R^2$, $R^3$, $R^4$, $R^6$, $R^{6a}$, X, V, Ring A, p, and each $R^{14}$ is selected independently of each other and wherein:

ring A forms a mono or multicyclic 4 to 12 membered heteroarylene ring, and $R^1$, $R^2$, $R^3$, $R^4$, $R^6$, $R^{6a}$, X, V, A, $R^{14}$, and p are as defined in Formula I.

In another embodiment, in Formula (III.c.), ring A together with V and X forms a monocyclic 4 to 12 membered heteroarylene.

In another embodiment, in Formula (III.c.), ring A together with V and X forms a monocyclic heteroarylene ring.

In another embodiment, in Formula (III.c.), ring A together with V and X forms a multicyclic heteroarylene ring.

In another embodiment, in Formula (III.c.), ring A together with V and X forms a bicyclic heteroarylene ring.

In another embodiment, in Formula (III.c.), ring A together with V and X forms a 5-6-membered monocyclic heteroarylene ring having from 1 to 4 ring heteroatoms independently selected from the group consisting of N, O, and S.

In another embodiment, in Formula (III.c.), ring A together with V and X forms a 5-6-membered monocyclic heteroarylene ring having from 1 ring heteroatom independently selected from the group consisting of N, O, and S.

In another embodiment, in Formula (III.c.), ring A together with V and X forms a 5-6-membered monocyclic heteroarylene ring having from 2 ring heteroatoms independently selected from the group consisting of N, O, and S.

In another embodiment, in Formula (III.c.), ring A together with V and X forms a 5-6-membered monocyclic heteroarylene ring having from 3 ring heteroatoms independently selected from the group consisting of N, O, and S.

In another embodiment, in Formula (III.c.), V is a carbon atom and V, X, and ring A, and —$(R^{14})_p$ form

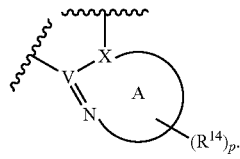

In another embodiment, in Formula (III.c.), V is a carbon atom and V, X, and ring A, and —$(R^{14})_p$ form

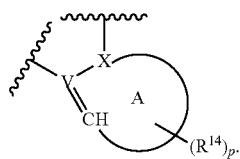

In another embodiment, in Formula (III.c.), V is a carbon atom and V, X, and ring A, and —$(R^{14})_p$ form

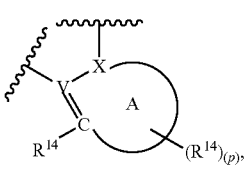

and p=0-4.

In another embodiment, in Formula (III.c), —V—X— is

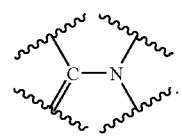

In another embodiment, in Formula (III.c), —V═X— is

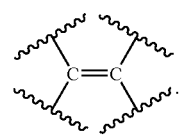

In another embodiment, in Formula (III.c.), ring A together with V and X forms a pyrazolyl, furanyl, theinyl, isoxazolyl, isothiazolyl, oxazolyl, thiazolyl, pyrazolyl, furazanyl, pyrrolyl, pyrazolyl, triazolyl, thiadiazolyl, pyridyl, pyrimidinyl, pyridonyl, imidazolyl, or pyrazinyl ring.

In another embodiment, in Formula (III.c.), ring A and —$(R^{14})_p$ is selected from the group consisting of:

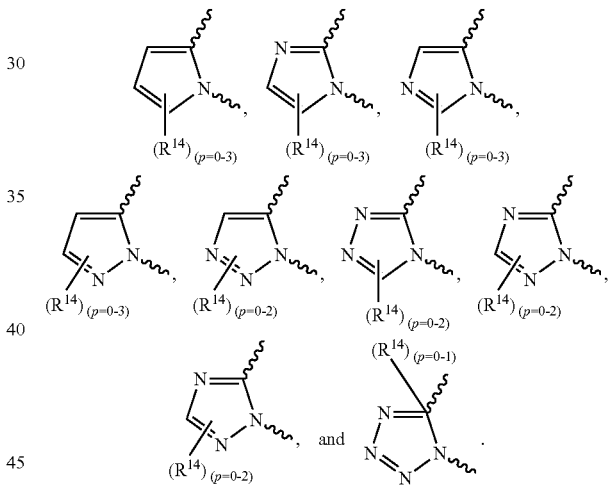

In another embodiment, in Formula (III.c.), ring A together with V and X forms an 8-10-membered bicyclic heteroarylene ring having 1 or more ring heteroatoms independently selected from the group consisting of N, O, and S.

In another embodiment, in Formula (III.c.), ring A together with V and X forms a quinoxalinyl, phthalazinyl, oxindolyl, imidazopyridinyl, imidazothiazolyl, benzofurazanyl, indolyl, azaindolyl, benzimidazolyl, benzothienyl, quinolinyl, quinazolinyl, isoquinolinyl, triazinyl, benzothiazoly, thieonpyridyl, thienopyrimidyl, imidazolpyridyl, or a pyrrolopyridyl ring.

In another embodiment, in Formula (III.c.), $R^1$ is alkyl.

In another embodiment, in Formula (III.c.), $R^1$ is methyl.

In another embodiment, in Formula (III.c.), $R^2$ is H.

In another embodiment, in Formula (III.c.), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.), $R^3$ is heteroaryl or aryl.

In another embodiment, in Formula (III.c.), $R^3$ is

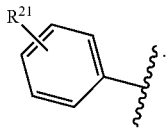

In another embodiment, in Formula (III.c.), $R^3$ is

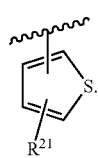

In another embodiment, in Formula (III.c.), $R^3$ is

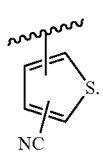

In another embodiment, in Formula (III.c.), $R^3$ is

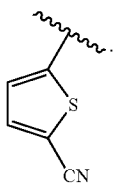

In another embodiment, in Formula (III.c.), $R^4$ is H.
In another embodiment, in Formula (III.c.), $R^4$ is alkyl.
In another embodiment, in Formula (III.c.), $R^4$ is halo.
In another embodiment, in Formula (III.c.), $R^6$ is H.
In another embodiment, in Formula (III.c.), $R^6$ is alkyl.
In another embodiment, in Formula (III.c.), $R^6$ is methyl.
In another embodiment, in Formula (III.c.), $R^6$ is ethyl.
In another embodiment, in Formula (III.c.), $R^{6a}$ is H.
In another embodiment, in Formula (III.c.), $R^{6a}$ is alkyl.
In another embodiment, in Formula (III.c.), $R^{6a}$ is methyl.
In another embodiment, in Formula (III.c.), $R^{6a}$ is ethyl.
In another embodiment, in Formula (III.c.), p is 0 (and $R^{14}$ is not present).
In another embodiment, in Formula (III.c.), p is 1.
In another embodiment, in Formula (III.c.), p is 2.
In another embodiment, in Formula (III.c.), p is 3.
In another embodiment, in Formula (III.c.), p is 4.
In another embodiment, in Formula (III.c.), p is 5.
In another embodiment, in Formula (III.c.), p is 2-5 and at least two groups $R^{14}$ are bound to the same ring atom.
In another embodiment, in Formula (III.c.), at least one group $R^{14}$ is H.
In another embodiment, in Formula (III.c.), at least one group $R^{14}$ is alkyl.
In another embodiment, in Formula (III.c.), at least one group $R^{14}$ is arylalkyl.
In another embodiment, in Formula (III.c.), at least one group $R^{14}$ is heteroarylalkyl.
In another embodiment, in Formula (III.c.), at least one group $R^{14}$ is cycloalkylalkyl.
In another embodiment, in Formula (III.c.), at least one group $R^{14}$ is heterocycloalkylalkyl.
In another embodiment, in Formula (III.c.), at least one group $R^{14}$ is arylcycloalkylalkyl.
In another embodiment, in Formula (III.c.), at least one group $R^{14}$ is heteroarylcycloalkylalkyl.
In another embodiment, in Formula (III.c.), at least one group $R^{14}$ is arylheterocycloalkylalkyl.
In another embodiment, in Formula (III.c.), at least one group $R^{14}$ is heteroarylheterocycloalkylalkyl.
In another embodiment, in Formula (III.c.), at least one group $R^{14}$ is cycloalkyl.
In another embodiment, in Formula (III.c.), at least one group $R^{14}$ is arylcycloalkyl.
In another embodiment, in Formula (III.c.), at least one group $R^{14}$ is heteroarylcycloalkyl.
In another embodiment, in Formula (III.c.), at least one group $R^{14}$ is heterocycloalkyl.
In another embodiment, in Formula (III.c.), at least one group $R^{14}$ is arylheterocycloalkyl.
In another embodiment, in Formula (III.c.), at least one group $R^{14}$ is heteroarylheterocycloalkyl.
In another embodiment, in Formula (III.c.), at least one group $R^{14}$ is alkenyl.
In another embodiment, in Formula (III.c.), at least one group $R^{14}$ is arylalkenyl.
In another embodiment, in Formula (III.c.), at least one group $R^{14}$ is cycloalkenyl.
In another embodiment, in Formula (III.c.), at least one group $R^{14}$ is arylcycloalkenyl.
In another embodiment, in Formula (III.c.), at least one group $R^{14}$ is heteroarylcycloalkenyl.
In another embodiment, in Formula (III.c.), at least one group $R^{14}$ is heterocycloalkenyl.
In another embodiment, in Formula (III.c.), at least one group $R^{14}$ is arylheterocycloalkenyl.
In another embodiment, in Formula (III.c.), at least one group $R^{14}$ is heteroarylheterocycloalkenyl.
In another embodiment, in Formula (III.c.), at least one group $R^{14}$ is alkynyl.
In another embodiment, in Formula (III.c.), at least one group $R^{14}$ is arylalkynyl.

In another embodiment, in Formula (III.c.), at least one group $R^{14}$ is aryl.

In another embodiment, in Formula (III.c.), at least one group $R^{14}$ is cycloalkylaryl.

In another embodiment, in Formula (III.c.), at least one group $R^{14}$ is heterocycloalkylaryl.

In another embodiment, in Formula (III.c.), at least one group $R^{14}$ is cycloalkenylaryl.

In another embodiment, in Formula (III.c.), at least one group $R^{14}$ is heterocycloalkenylaryl.

In another embodiment, in Formula (III.c.), at least one group $R^{14}$ is heteroaryl.

In another embodiment, in Formula (III.c.), at least one group $R^{14}$ is cycloalkylheteroaryl.

In another embodiment, in Formula (III.c.), at least one group $R^{14}$ is heterocycloalkylheteroaryl.

In another embodiment, in Formula (III.c.), at least one group $R^{14}$ is cycloalkenylheteroaryl.

In another embodiment, in Formula (III.c.), at least one group $R^{14}$ is heterocycloalkenylheteroaryl.

In another embodiment, in Formula (III.c.), at least one group $R^{14}$ is halo.

In another embodiment, in Formula (III.c.), at least one group $R^{14}$ is —$CH_2$—O—$Si(R^9)(R^{10})(R^{19})$.

In another embodiment, in Formula (III.c.), at least one group $R^{14}$ is —$N(R^{15})C(O)N(R^{16})(R^{17})$.

In another embodiment, in Formula (III.c.), at least one group $R^{14}$ is —CN.

In another embodiment, in Formula (III.c.), at least one group $R^{14}$ is —$OR^{15}$.

In another embodiment, in Formula (III.c.), at least one group $R^{14}$ is —$C(O)R^{15}$.

In another embodiment, in Formula (III.c.), at least one group $R^{14}$ is —$C(O)OR^{15}$.

In another embodiment, in Formula (III.c.), at least one group $R^{14}$ is —$C(O)N(R^{15})(R^{16})$.

In another embodiment, in Formula (III.c.), at least one group $R^{14}$ is —$SR^{15}$.

In another embodiment, in Formula (III.c.), at least one group $R^{14}$ is —$S(O)N(R^{15})(R^{16})$.

In another embodiment, in Formula (III.c.), at least one group $R^{14}$ is —$S(O)_2N(R^{15})(R^{16})$.

In another embodiment, in Formula (III.c.), at least one group $R^{14}$ is —$C(=NOR^{15})R^{16}$.

In another embodiment, in Formula (III.c.), at least one group $R^{14}$ is —$P(O)(OR^{15})(OR^{16})$.

In another embodiment, in Formula (III.c.), at least one group $R^{14}$ is —$N(R^{15})(R^{16})$.

In another embodiment, in Formula (III.c.), at least one group $R^{14}$ is —$N(R^{15})C(O)R^{16}$.

In another embodiment, in Formula (III.c.), at least one group $R^{14}$ is —$N(R^{15})S(O)R^{16}$.

In another embodiment, in Formula (III.c.), at least one group $R^{14}$ is —$N(R^{15})S(O)_2R^{16}$.

In another embodiment, in Formula (III.c.), at least one group $R^{14}$ is —$N(R^{15})S(O)_2N(R^{16})(R^{17})$.

In another embodiment, in Formula (III.c.), at least one group $R^{14}$ is —$N(R^{15})S(O)N(R^{16})(R^{17})$.

In another embodiment, in Formula (III.c.), at least one group $R^{14}$ is —$N(R^{15})C(O)N(R^{16})(R^{17})$.

In another embodiment, in Formula (III.c.), at least one group $R^{14}$ is —$N(R^{15})C(O)OR^{16}$.

In another embodiment, the present invention provides a compound, or a stereoisomer, tautomer, or pharmaceutically acceptable salt or solvate thereof, having the general structure shown in Formula (III.c.1):

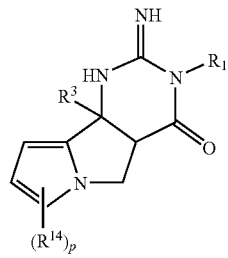

(III.c.1)

wherein $R^1$, $R^3$, $R^{14}$, and p are selected independently, and wherein p is 0-3 and $R^1$, $R^3$, $R^{14}$ are as defined in Formula (I).

In another embodiment, in Formula (III.c.1), $R^1$ is alkyl.

In another embodiment, in Formula (III.c.1), $R^1$ is methyl.

In another embodiment, in Formula (III.c.1), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.1), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.1), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.1), $R^3$ is heteroaryl or aryl.

In another embodiment, in Formula (III.c.1), $R^3$ is

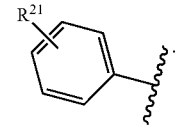

In another embodiment, in Formula (III.c.1), $R^3$ is

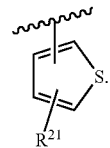

In another embodiment, in Formula (III.c.1), $R^3$ is

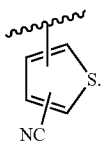

In another embodiment, in Formula (III.c.1), $R^3$ is

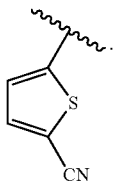

In another embodiment, in Formula (III.c.1), p is 0 (and $R^{14}$ is not present).

In another embodiment, in Formula (III.c.1), p is 1.
In another embodiment, in Formula (III.c.1), p is 2.
In another embodiment, in Formula (III.c.1), p is 3.
In another embodiment, in Formula (III.c.1), p is 4.
In another embodiment, in Formula (III.c.1), p is 5.
In another embodiment, in Formula (III.c.1), p is 2-5 and at least two groups $R^{14}$ are bound to the same ring atom.

In another embodiment, in Formula (III.c.1), at least one group $R^{14}$ is H.
In another embodiment, in Formula (III.c.1), at least one group $R^{14}$ is alkyl.
In another embodiment, in Formula (III.c.1), at least one group $R^{14}$ is arylalkyl.
In another embodiment, in Formula (III.c.1), at least one group $R^{14}$ is heteroarylalkyl.
In another embodiment, in Formula (III.c.1), at least one group $R^{14}$ is cycloalkylalkyl.
In another embodiment, in Formula (III.c.1), at least one group $R^{14}$ is heterocycloalkylalkyl.
In another embodiment, in Formula (III.c.1), at least one group $R^{14}$ is arylcycloalkylalkyl.
In another embodiment, in Formula (III.c.1), at least one group $R^{14}$ is heteroarylcycloalkylalkyl.
In another embodiment, in Formula (III.c.1), at least one group $R^{14}$ is arylheterocycloalkylalkyl.
In another embodiment, in Formula (III.c.1), at least one group $R^{14}$ is heteroarylheterocycloalkylalkyl.
In another embodiment, in Formula (III.c.1), at least one group $R^{14}$ is cycloalkyl.
In another embodiment, in Formula (III.c.1), at least one group $R^{14}$ is arylcycloalkyl.
In another embodiment, in Formula (III.c.1), at least one group $R^{14}$ is heteroarylcycloalkyl.
In another embodiment, in Formula (III.c.1), at least one group $R^{14}$ is heterocycloalkyl.
In another embodiment, in Formula (III.c.1), at least one group $R^{14}$ is arylheterocycloalkyl.
In another embodiment, in Formula (III.c.1), at least one group $R^{14}$ is heteroarylheterocycloalkyl.
In another embodiment, in Formula (III.c.1), at least one group $R^{14}$ is alkenyl.
In another embodiment, in Formula (III.c.1), at least one group $R^{14}$ is arylalkenyl.
In another embodiment, in Formula (III.c.1), at least one group $R^{14}$ is cycloalkenyl.
In another embodiment, in Formula (III.c.1), at least one group $R^{14}$ is arylcycloalkenyl.
In another embodiment, in Formula (III.c.1), at least one group $R^{14}$ is heteroarylcycloalkenyl.
In another embodiment, in Formula (III.c.1), at least one group $R^{14}$ is heterocycloalkenyl.
In another embodiment, in Formula (III.c.1), at least one group $R^{14}$ is arylheterocycloalkenyl.
In another embodiment, in Formula (III.c.1), at least one group $R^{14}$ is heteroarylheterocycloalkenyl.
In another embodiment, in Formula (III.c.1), at least one group $R^{14}$ is alkynyl.
In another embodiment, in Formula (III.c.1), at least one group $R^{14}$ is arylalkynyl.
In another embodiment, in Formula (III.c.1), at least one group $R^{14}$ is aryl.
In another embodiment, in Formula (III.c.1), at least one group $R^{14}$ is cycloalkylaryl.
In another embodiment, in Formula (III.c.1), at least one group $R^{14}$ is heterocycloalkylaryl.
In another embodiment, in Formula (III.c.1), at least one group $R^{14}$ is cycloalkenylaryl.
In another embodiment, in Formula (III.c.1), at least one group $R^{14}$ is heterocycloalkenylaryl.
In another embodiment, in Formula (III.c.1), at least one group $R^{14}$ is heteroaryl.
In another embodiment, in Formula (III.c.1), at least one group $R^{14}$ is cycloalkylheteroaryl.
In another embodiment, in Formula (III.c.1), at least one group $R^{14}$ is heterocycloalkylheteroaryl.
In another embodiment, in Formula (III.c.1), at least one group $R^{14}$ is cycloalkenylheteroaryl.
In another embodiment, in Formula (III.c.1), at least one group $R^{14}$ is heterocycloalkenylheteroaryl.
In another embodiment, in Formula (III.c.1), at least one group $R^{14}$ is halo.
In another embodiment, in Formula (III.c.1), at least one group $R^{14}$ is —$CH_2$—O—Si($R^9$)($R^{10}$)($R^{19}$).
In another embodiment, in Formula (III.c.1), at least one group $R^{14}$ is —N($R^{15}$)C(O)N($R^{16}$)($R^{17}$).
In another embodiment, in Formula (III.c.1), at least one group $R^{14}$ is —CN.
In another embodiment, in Formula (III.c.1), at least one group $R^4$ is —$OR^{15}$.
In another embodiment, in Formula (III.c.1), at least one group $R^{14}$ is —C(O)$R^{15}$.
In another embodiment, in Formula (III.c.1), at least one group $R^{14}$ is —C(O)$OR^{15}$.
In another embodiment, in Formula (III.c.1), at least one group $R^{14}$ is —C(O)N($R^{15}$)($R^{16}$).
In another embodiment, in Formula (III.c.1), at least one group $R^{14}$ is —$SR^{15}$.
In another embodiment, in Formula (III.c.1), at least one group $R^{14}$ is —S(O)N($R^{15}$)($R^{16}$).
In another embodiment, in Formula (III.c.1), at least one group $R^{14}$ is —$S(O)_2$N($R^{15}$)($R^{16}$).
In another embodiment, in Formula (III.c.1), at least one group $R^{14}$ is —C(=$NOR^{15}$)$R^{16}$.
In another embodiment, in Formula (III.c.1), at least one group $R^{14}$ is —P(O)($OR^{15}$)($OR^{16}$).
In another embodiment, in Formula (III.c.1), at least one group $R^{14}$ is —N($R^{15}$)($R^{16}$).
In another embodiment, in Formula (III.c.1), at least one group $R^{14}$ is —N($R^{15}$)C(O)$R^{16}$.

In another embodiment, in Formula (III.c.1), at least one group $R^{14}$ is —N($R^{15}$)S(O)$R^{16}$.

In another embodiment, in Formula (III.c.1), at least one group $R^{14}$ is —N($R^{15}$)S(O)$_2R^{16}$.

In another embodiment, in Formula (III.c.1), at least one group $R^{14}$ is —N($R^{15}$)S(O)$_2$N($R^{16}$)($R^{17}$).

In another embodiment, in Formula (III.c.1), at least one group $R^{14}$ is —N($R^{15}$)S(O)N($R^{16}$)($R^{17}$).

In another embodiment, in Formula (III.c.1), at least one group $R^{14}$ is —N($R^{15}$)C(O)N($R^{16}$)($R^{17}$).

In another embodiment, in Formula (III.c.1), at least one group $R^{14}$ is —N($R^{15}$)C(O)O$R^{16}$.

In another embodiment, the present invention provides a compound, or a stereoisomer, tautomer, or pharmaceutically acceptable salt or solvate thereof, having the general structure shown in Formula (III.c.1A):

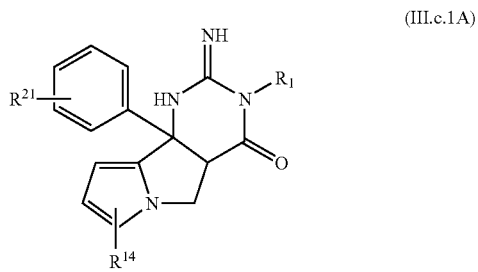

(III.c.1A)

wherein $R^1$, $R^{14}$, and $R^{21}$ are selected independently and $R^1$ and $R^{14}$ are as defined in Formula (III.c.1) and $R^{21}$ is as defined in Formula (I).

In another embodiment, the present invention provides a compound, or a stereoisomer, tautomer, or pharmaceutically acceptable salt or solvate thereof, having the general structure shown in Formula (III.c.2):

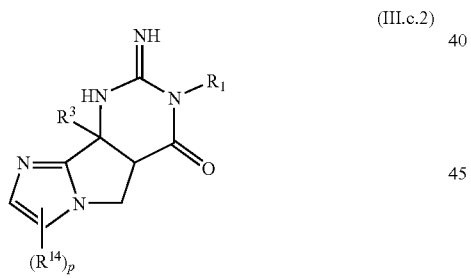

(III.c.2)

wherein $R^1$, $R^3$, $R^{14}$, and p are selected independently, and wherein p is 0-3 and $R^1$, $R^3$, $R^{14}$ are as defined in Formula (I).

In another embodiment, in Formula (III.c.2), $R^1$ is alkyl.
In another embodiment, in Formula (III.c.2), $R^1$ is methyl.
In another embodiment, in Formula (III.c.2), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.2), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.2), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.2), $R^3$ is heteroaryl or aryl.

In another embodiment, in Formula (III.c.2), $R^3$ is

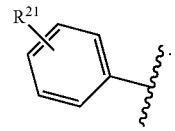

In another embodiment, in Formula (III.c.2), $R^3$ is

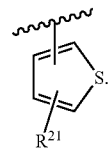

In another embodiment, in Formula (III.c.2), $R^3$ is

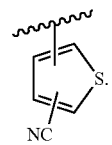

In another embodiment, in Formula (III.c.2), $R^3$ is

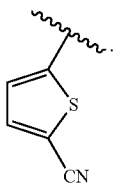

In another embodiment, in Formula (III.c.2), p is 0 (and $R^{14}$ is not present).

In another embodiment, in Formula (III.c.2), p is 1.
In another embodiment, in Formula (III.c.2), p is 2.
In another embodiment, in Formula (III.c.2), p is 3.
In another embodiment, in Formula (III.c.2), p is 4.
In another embodiment, in Formula (III.c.2), p is 5.
In another embodiment, in Formula (III.c.2), p is 2-5 and at least two groups $R^{14}$ are bound to the same ring atom.

In another embodiment, in Formula (III.c.2), at least one group $R^{14}$ is H.

In another embodiment, in Formula (III.c.2), at least one group $R^{14}$ is alkyl.

In another embodiment, in Formula (III.c.2), at least one group $R^{14}$ is arylalkyl.

In another embodiment, in Formula (III.c.2), at least one group $R^{14}$ is heteroarylalkyl.

In another embodiment, in Formula (III.c.2), at least one group $R^{14}$ is cycloalkylalkyl.

In another embodiment, in Formula (III.c.2), at least one group $R^{14}$ is heterocycloalkylalkyl.

In another embodiment, in Formula (III.c.2), at least one group $R^{14}$ is arylcycloalkylalkyl.

In another embodiment, in Formula (III.c.2), at least one group $R^{14}$ is heteroarylcycloalkylalkyl.

In another embodiment, in Formula (III.c.2), at least one group $R^{14}$ is arylheterocycloalkylalkyl.

In another embodiment, in Formula (III.c.2), at least one group $R^{14}$ is heteroarylheterocycloalkylalkyl.

In another embodiment, in Formula (III.c.2), at least one group $R^{14}$ is cycloalkyl.

In another embodiment, in Formula (III.c.2), at least one group $R^{14}$ is arylcycloalkyl.

In another embodiment, in Formula (III.c.2), at least one group $R^{14}$ is heteroarylcycloalkyl.

In another embodiment, in Formula (III.c.2), at least one group $R^{14}$ is heterocycloalkyl.

In another embodiment, in Formula (III.c.2), at least one group $R^{14}$ is arylheterocycloalkyl.

In another embodiment, in Formula (III.c.2), at least one group $R^{14}$ is heteroarylheterocycloalkyl.

In another embodiment, in Formula (III.c.2), at least one group $R^{14}$ is alkenyl.

In another embodiment, in Formula (III.c.2), at least one group $R^{14}$ is arylalkenyl.

In another embodiment, in Formula (III.c.2), at least one group $R^{14}$ is cycloalkenyl.

In another embodiment, in Formula (III.c.2), at least one group $R^{14}$ is arylcycloalkenyl.

In another embodiment, in Formula (III.c.2), at least one group $R^{14}$ is heteroarylcycloalkenyl.

In another embodiment, in Formula (III.c.2), at least one group $R^{14}$ is heterocycloalkenyl.

In another embodiment, in Formula (III.c.2), at least one group $R^{14}$ is arylheterocycloalkenyl.

In another embodiment, in Formula (III.c.2), at least one group $R^{14}$ is heteroarylheterocycloalkenyl.

In another embodiment, in Formula (III.c.2), at least one group $R^{14}$ is alkynyl.

In another embodiment, in Formula (III.c.2), at least one group $R^{14}$ is arylalkynyl.

In another embodiment, in Formula (III.c.2), at least one group $R^{14}$ is aryl.

In another embodiment, in Formula (III.c.2), at least one group $R^{14}$ is cycloalkylaryl.

In another embodiment, in Formula (III.c.2), at least one group $R^{14}$ is heterocycloalkylaryl.

In another embodiment, in Formula (III.c.2), at least one group $R^{14}$ is cycloalkenylaryl.

In another embodiment, in Formula (III.c.2), at least one group $R^{14}$ is heterocycloalkenylaryl.

In another embodiment, in Formula (III.c.2), at least one group $R^{14}$ is heteroaryl.

In another embodiment, in Formula (III.c.2), at least one group $R^{14}$ is cycloalkylheteroaryl.

In another embodiment, in Formula (III.c.2), at least one group $R^{14}$ is heterocycloalkylheteroaryl.

In another embodiment, in Formula (III.c.2), at least one group $R^{14}$ is cycloalkenylheteroaryl.

In another embodiment, in Formula (III.c.2), at least one group $R^{14}$ is heterocycloalkenylheteroaryl.

In another embodiment, in Formula (III.c.2), at least one group $R^{14}$ is halo.

In another embodiment, in Formula (III.c.2), at least one group $R^{14}$ is —$CH_2$—O—$Si(R^9)(R^{10})(R^{19})$.

In another embodiment, in Formula (III.c.2), at least one group $R^{14}$ is —$N(R^{15})C(O)N(R^{16})(R^{17})$.

In another embodiment, in Formula (III.c.2), at least one group $R^{14}$ is —CN.

In another embodiment, in Formula (III.c.2), at least one group $R^{14}$ is —$OR^{15}$.

In another embodiment, in Formula (III.c.2), at least one group $R^{14}$ is —$C(O)R^{15}$.

In another embodiment, in Formula (III.c.2), at least one group $R^{14}$ is —$C(O)OR^{15}$.

In another embodiment, in Formula (III.c.2), at least one group $R^{14}$ is —$C(O)N(R^{15})(R^{16})$.

In another embodiment, in Formula (III.c.2), at least one group $R^{14}$ is —$SR^{15}$.

In another embodiment, in Formula (III.c.2), at least one group $R^{14}$ is —$S(O)N(R^{15})(R^{16})$.

In another embodiment, in Formula (III.c.2), at least one group $R^{14}$ is —$S(O)_2N(R^{15})(R^{16})$.

In another embodiment, in Formula (III.c.2), at least one group $R^{14}$ is —$C(=NOR^{15})R^{16}$.

In another embodiment, in Formula (III.c.2), at least one group $R^{14}$ is —$P(O)(OR^{15})(OR^{16})$.

In another embodiment, in Formula (III.c.2), at least one group $R^{14}$ is —$N(R^{15})(R^{16})$.

In another embodiment, in Formula (III.c.2), at least one group $R^{14}$ is —$N(R^{15})C(O)R^{16}$.

In another embodiment, in Formula (III.c.2), at least one group $R^{14}$ is —$N(R^{15})S(O)R^{16}$.

In another embodiment, in Formula (III.c.2), at least one group $R^{14}$ is —$N(R^{15})S(O)_2R^{16}$.

In another embodiment, in Formula (III.c.2), at least one group $R^{14}$ is —$N(R^{15})S(O)_2N(R^{16})(R^{17})$.

In another embodiment, in Formula (III.c.2), at least one group $R^{14}$ is —$N(R^{15})S(O)N(R^{16})(R^{17})$.

In another embodiment, in Formula (III.c.2), at least one group $R^{14}$ is —$N(R^{15})C(O)N(R^{16})(R^{17})$.

In another embodiment, in Formula (III.c.2), at least one group $R^{14}$ is —$N(R^{15})C(O)OR^{16}$.

In another embodiment, the present invention provides a compound, or a stereoisomer, tautomer, or pharmaceutically acceptable salt or solvate thereof, having the general structure shown in Formula (III.c.2A):

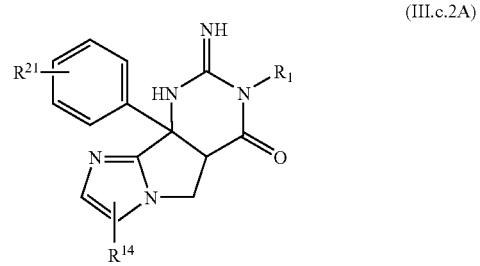

(III.c.2A)

wherein $R^1$, $R^{14}$, and $R^{21}$ are selected independently and $R^1$ and $R^{14}$ are as defined in Formula (III.c.2) and $R^{21}$ is as defined in Formula (I).

In another embodiment, the present invention provides a compound, or a stereoisomer, tautomer, or pharmaceutically acceptable salt or solvate thereof, having the general structure shown in Formula (III.c.2B):

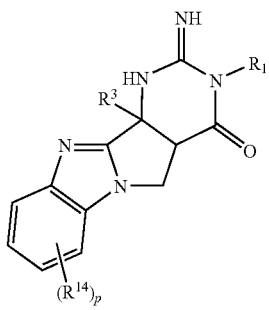

(III.c.2B)

wherein $R^1$, $R^3$, $R^{14}$, and p are selected independently, and wherein p is 0-3 and $R^1$, $R^3$, $R^{14}$ are as defined in Formula (I).

In one embodiment, in Formula (III.c.2B), p is 0-3 and $R^1$, $R^3$, $R^{14}$ are as defined in Formula (III.c.2).

In another embodiment, the present invention provides a compound, or a stereoisomer, tautomer, or pharmaceutically acceptable salt or solvate thereof, having the general structure shown in Formula (III.c.2B1):

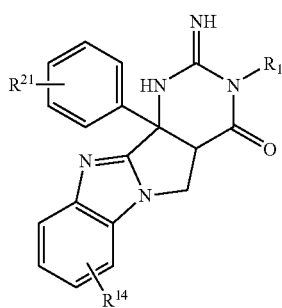

(III.c.2B1)

wherein $R^1$, $R^{14}$, and $R^{21}$ are selected independently, and as defined in Formula (III.c.2).

In another embodiment, the present invention provides a compound, or a stereoisomer, tautomer, or pharmaceutically acceptable salt or solvate thereof, having the general structure shown in Formula (III.c.3):

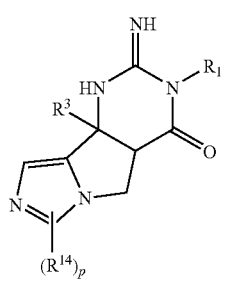

(III.c.3)

wherein $R^1$, $R^3$, $R^{14}$, and p are selected independently, and wherein p is 0-3 and $R^1$, $R^3$, $R^{14}$ are as defined in Formula (I).

In another embodiment, in Formula (III.c.3), $R^1$ is alkyl.

In another embodiment, in Formula (III.c.3), $R^1$ is methyl.

In another embodiment, in Formula (III.c.3), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.3), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.3), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.3), $R^3$ is heteroaryl or aryl.

In another embodiment, in Formula (III.c.3), $R^3$ is

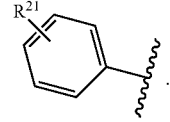

In another embodiment, in Formula (III.c.3), $R^3$ is

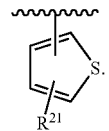

In another embodiment, in Formula (III.c.3), $R^3$ is

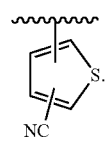

In another embodiment, in Formula (III.c.3), $R^3$ is

[structure: thiophene with CN substituent]

In another embodiment, in Formula (III.c.3), p is 0 (and $R^{14}$ is not present).
In another embodiment, in Formula (III.c.3), p is 1.
In another embodiment, in Formula (III.c.3), p is 2.
In another embodiment, in Formula (III.c.3), p is 3.
In another embodiment, in Formula (III.c.3), p is 4.
In another embodiment, in Formula (III.c.3), p is 5.
In another embodiment, in Formula (III.c.3), p is 2-5 and at least two groups $R^{14}$ are bound to the same ring atom.
In another embodiment, in Formula (III.c.3), at least one group $R^{14}$ is H.
In another embodiment, in Formula (III.c.3), at least one group $R^{14}$ is alkyl.
In another embodiment, in Formula (III.c.3), at least one group $R^{14}$ is arylalkyl.
In another embodiment, in Formula (III.c.3), at least one group $R^{14}$ is heteroarylalkyl.
In another embodiment, in Formula (III.c.3), at least one group $R^{14}$ is cycloalkylalkyl.
In another embodiment, in Formula (III.c.3), at least one group $R^{14}$ is heterocycloalkylalkyl.
In another embodiment, in Formula (III.c.3), at least one group $R^{14}$ is arylcycloalkylalkyl.
In another embodiment, in Formula (III.c.3), at least one group $R^{14}$ is heteroarylcycloalkylalkyl.
In another embodiment, in Formula (III.c.3), at least one group $R^{14}$ is arylheterocycloalkylalkyl.
In another embodiment, in Formula (III.c.3), at least one group $R^{14}$ is heteroarylheterocycloalkylalkyl.
In another embodiment, in Formula (III.c.3), at least one group $R^{14}$ is cycloalkyl.
In another embodiment, in Formula (III.c.3), at least one group $R^{14}$ is arylcycloalkyl.
In another embodiment, in Formula (III.c.3), at least one group $R^{14}$ is heteroarylcycloalkyl.
In another embodiment, in Formula (III.c.3), at least one group $R^{14}$ is heterocycloalkyl.
In another embodiment, in Formula (III.c.3), at least one group $R^{14}$ is arylheterocycloalkyl.
In another embodiment, in Formula (III.c.3), at least one group $R^{14}$ is heteroarylheterocycloalkyl.
In another embodiment, in Formula (III.c.3), at least one group $R^{14}$ is alkenyl.
In another embodiment, in Formula (III.c.3), at least one group $R^{14}$ is arylalkenyl.
In another embodiment, in Formula (III.c.3), at least one group $R^{14}$ is cycloalkenyl.
In another embodiment, in Formula (III.c.3), at least one group $R^{14}$ is arylcycloalkenyl.
In another embodiment, in Formula (III.c.3), at least one group $R^{14}$ is heteroarylcycloalkenyl.
In another embodiment, in Formula (III.c.3), at least one group $R^{14}$ is heterocycloalkenyl.
In another embodiment, in Formula (III.c.3), at least one group $R^{14}$ is arylheterocycloalkenyl.
In another embodiment, in Formula (III.c.3), at least one group $R^{14}$ is heteroarylheterocycloalkenyl.
In another embodiment, in Formula (III.c.3), at least one group $R^{14}$ is alkynyl.
In another embodiment, in Formula (III.c.3), at least one group $R^{14}$ is arylalkynyl.
In another embodiment, in Formula (III.c.3), at least one group $R^{14}$ is aryl.
In another embodiment, in Formula (III.c.3), at least one group $R^{14}$ is cycloalkylaryl.
In another embodiment, in Formula (III.c.3), at least one group $R^{14}$ is heterocycloalkylaryl.
In another embodiment, in Formula (III.c.3), at least one group $R^{14}$ is cycloalkenylaryl.
In another embodiment, in Formula (III.c.3), at least one group $R^{14}$ is heterocycloalkenylaryl.
In another embodiment, in Formula (III.c.3), at least one group $R^{14}$ is heteroaryl.
In another embodiment, in Formula (III.c.3), at least one group $R^{14}$ is cycloalkylheteroaryl.
In another embodiment, in Formula (III.c.3), at least one group $R^{14}$ is heterocycloalkylheteroaryl.
In another embodiment, in Formula (III.c.3), at least one group $R^{14}$ is cycloalkenylheteroaryl.
In another embodiment, in Formula (III.c.3), at least one group $R^{14}$ is heterocycloalkenylheteroaryl.
In another embodiment, in Formula (III.c.3), at least one group $R^{14}$ is halo.
In another embodiment, in Formula (III.c.3), at least one group $R^{14}$ is —$CH_2$—O—Si(R)($R^{10}$)($R^{19}$).
In another embodiment, in Formula (III.c.3), at least one group $R^{14}$ is —N($R^{15}$)C(O)N($R^{16}$)($R^{17}$).
In another embodiment, in Formula (III.c.3), at least one group $R^{14}$ is —CN.
In another embodiment, in Formula (III.c.3), at least one group $R^{14}$ is —$OR^{15}$.
In another embodiment, in Formula (III.c.3), at least one group $R^{14}$ is —C(O)$R^{15}$.
In another embodiment, in Formula (III.c.3), at least one group $R^{14}$ is —C(O)$OR^{15}$.
In another embodiment, in Formula (III.c.3), at least one group $R^{14}$ is —C(O)N($R^{15}$)($R^{16}$).
In another embodiment, in Formula (III.c.3), at least one group $R^{14}$ is —$SR^{15}$.
In another embodiment, in Formula (III.c.3), at least one group $R^{14}$ is —S(O)N($R^{15}$)($R^{16}$).
In another embodiment, in Formula (III.c.3), at least one group $R^{14}$ is —S(O)$_2$N($R^{15}$)($R^{16}$).
In another embodiment, in Formula (III.c.3), at least one group $R^{14}$ is —C(=NOR$^{15}$)$R^{16}$.
In another embodiment, in Formula (III.c.3), at least one group $R^{14}$ is —P(O)(O$R^{15}$)(O$R^{16}$).
In another embodiment, in Formula (III.c.3), at least one group $R^{14}$ is —N($R^{15}$)($R^{16}$).
In another embodiment, in Formula (III.c.3), at least one group $R^{14}$ is —N($R^{15}$)C(O)$R^{16}$.
In another embodiment, in Formula (III.c.3), at least one group $R^{14}$ is —N($R^{15}$)S(O)$R^{16}$.
In another embodiment, in Formula (III.c.3), at least one group $R^{14}$ is —N($R^{15}$)S(O)$_2R^{16}$.
In another embodiment, in Formula (III.c.3), at least one group $R^{14}$ is —N($R^{15}$)S(O)$_2$N($R^{16}$)($R^{17}$).
In another embodiment, in Formula (III.c.3), at least one group $R^{14}$ is —N($R^{15}$)S(O)N($R^{16}$)($R^{17}$).
In another embodiment, in Formula (III.c.3), at least one group $R^{14}$ is —N($R^{15}$)C(O)N($R^{16}$)($R^{17}$).

In another embodiment, in Formula (III.c.3), at least one group $R^{14}$ is —N($R^{15}$)C(O)O$R^{16}$.

In another embodiment, the present invention provides a compound, or a stereoisomer, tautomer, or pharmaceutically acceptable salt or solvate thereof, having the general structure shown in Formula (III.c.3A):

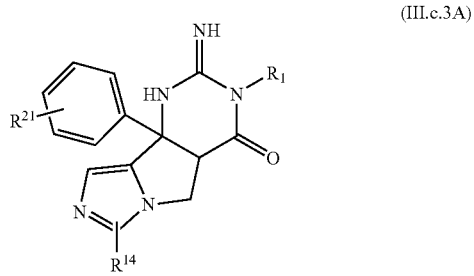
(III.c.3A)

wherein $R^1$, $R^{14}$, and $R^{21}$ are selected independently and $R^1$ and $R^{14}$ are as defined in Formula (III.c.3) and $R^{21}$ is as defined in Formula (I).

In another embodiment, the present invention provides a compound, or a stereoisomer, tautomer, or pharmaceutically acceptable salt or solvate thereof, having the general structure shown in Formula (III.c.4):

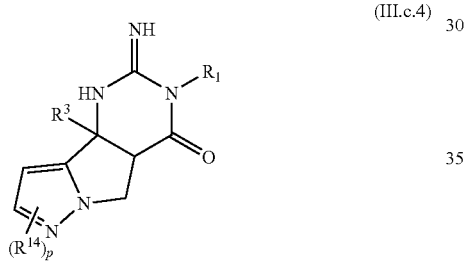
(III.c.4)

wherein $R^1$, $R^3$, $R^{14}$, and p are selected independently, and wherein p is 0-3 and $R^1$, $R^3$, $R^{14}$ are as defined in Formula (I).

In another embodiment, in Formula (III.c.4), $R^1$ is alkyl.
In another embodiment, in Formula (III.c.4), $R^1$ is methyl.
In another embodiment, in Formula (III.c.4), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.4), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.4), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.4), $R^3$ is heteroaryl or aryl.

In another embodiment, in Formula (III.c.4), $R^3$ is

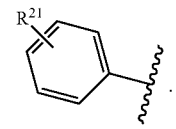

In another embodiment, in Formula (III.c.4), $R^3$ is

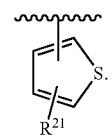

In another embodiment, in Formula (III.c.4), $R^3$ is

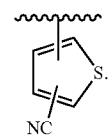

In another embodiment, in Formula (III.c.4), $R^3$ is

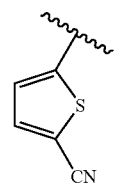

In another embodiment, in Formula (III.c.4), p is 0 (and $R^{14}$ is not present).
In another embodiment, in Formula (III.c.4), p is 1.
In another embodiment, in Formula (III.c.4), p is 2.
In another embodiment, in Formula (III.c.4), p is 3.
In another embodiment, in Formula (III.c.4), p is 4.
In another embodiment, in Formula (III.c.4), p is 5.
In another embodiment, in Formula (III.c.4), p is 2-5 and at least two groups $R^{14}$ are bound to the same ring atom.
In another embodiment, in Formula (III.c.4), at least one group $R^{14}$ is H.
In another embodiment, in Formula (III.c.4), at least one group $R^{14}$ is alkyl.
In another embodiment, in Formula (III.c.4), at least one group $R^{14}$ is arylalkyl.
In another embodiment, in Formula (III.c.4), at least one group $R^{14}$ is heteroarylalkyl.
In another embodiment, in Formula (III.c.4), at least one group $R^{14}$ is cycloalkylalkyl.
In another embodiment, in Formula (III.c.4), at least one group $R^{14}$ is heterocycloalkylalkyl.
In another embodiment, in Formula (III.c.4), at least one group $R^{14}$ is arylcycloalkylalkyl.

In another embodiment, in Formula (III.c.4), at least one group $R^{14}$ is heteroarylcycloalkylalkyl.

In another embodiment, in Formula (III.c.4), at least one group $R^{14}$ is arylheterocycloalkylalkyl.

In another embodiment, in Formula (III.c.4), at least one group $R^{14}$ is heteroarylheterocycloalkylalkyl.

In another embodiment, in Formula (III.c.4), at least one group $R^{14}$ is cycloalkyl.

In another embodiment, in Formula (III.c.4), at least one group $R^{14}$ is arylcycloalkyl.

In another embodiment, in Formula (III.c.4), at least one group $R^{14}$ is heteroarylcycloalkyl.

In another embodiment, in Formula (III.c.4), at least one group $R^{14}$ is heterocycloalkyl.

In another embodiment, in Formula (III.c.4), at least one group $R^{14}$ is arylheterocycloalkyl.

In another embodiment, in Formula (III.c.4), at least one group $R^{14}$ is heteroarylheterocycloalkyl.

In another embodiment, in Formula (III.c.4), at least one group $R^{14}$ is alkenyl.

In another embodiment, in Formula (III.c.4), at least one group $R^{14}$ is arylalkenyl.

In another embodiment, in Formula (III.c.4), at least one group $R^{14}$ is cycloalkenyl.

In another embodiment, in Formula (III.c.4), at least one group $R^{14}$ is arylcycloalkenyl.

In another embodiment, in Formula (III.c.4), at least one group $R^{14}$ is heteroarylcycloalkenyl.

In another embodiment, in Formula (III.c.4), at least one group $R^{14}$ is heterocycloalkenyl.

In another embodiment, in Formula (III.c.4), at least one group $R^{14}$ is arylheterocycloalkenyl.

In another embodiment, in Formula (III.c.4), at least one group $R^{14}$ is heteroarylheterocycloalkenyl.

In another embodiment, in Formula (III.c.4), at least one group $R^{14}$ is alkynyl.

In another embodiment, in Formula (III.c.4), at least one group $R^{14}$ is arylalkynyl.

In another embodiment, in Formula (III.c.4), at least one group $R^{14}$ is aryl.

In another embodiment, in Formula (III.c.4), at least one group $R^{14}$ is cycloalkylaryl.

In another embodiment, in Formula (III.c.4), at least one group $R^{14}$ is heterocycloalkylaryl.

In another embodiment, in Formula (III.c.4), at least one group $R^{14}$ is cycloalkenylaryl.

In another embodiment, in Formula (III.c.4), at least one group $R^{14}$ is heterocycloalkenylaryl.

In another embodiment, in Formula (III.c.4), at least one group $R^{14}$ is heteroaryl.

In another embodiment, in Formula (III.c.4), at least one group $R^{14}$ is cycloalkylheteroaryl.

In another embodiment, in Formula (III.c.4), at least one group $R^{14}$ is heterocycloalkylheteroaryl.

In another embodiment, in Formula (III.c.4), at least one group $R^{14}$ is cycloalkenylheteroaryl.

In another embodiment, in Formula (III.c.4), at least one group $R^{14}$ is heterocycloalkenylheteroaryl.

In another embodiment, in Formula (III.c.4), at least one group $R^{14}$ is halo.

In another embodiment, in Formula (III.c.4), at least one group $R^{14}$ is $-CH_2-O-Si(R^9)(R^{10})(R^{19})$.

In another embodiment, in Formula (III.c.4), at least one group $R^{14}$ is $-N(R^{15})C(O)N(R^{16})(R^{17})$.

In another embodiment, in Formula (III.c.4), at least one group $R^{14}$ is $-CN$.

In another embodiment, in Formula (III.c.4), at least one group $R^{14}$ is $-OR^{15}$.

In another embodiment, in Formula (III.c.4), at least one group $R^{14}$ is $-C(O)R^{15}$.

In another embodiment, in Formula (III.c.4), at least one group $R^{14}$ is $-C(O)OR^{15}$.

In another embodiment, in Formula (III.c.4), at least one group $R^{14}$ is $-C(O)N(R^{15})(R^{16})$.

In another embodiment, in Formula (III.c.4), at least one group $R^{14}$ is $-SR^{15}$.

In another embodiment, in Formula (III.c.4), at least one group $R^{14}$ is $-S(O)N(R^{15})(R^{16})$.

In another embodiment, in Formula (III.c.4), at least one group $R^{14}$ is $-S(O)_2N(R^{15})(R^{16})$.

In another embodiment, in Formula (III.c.4), at least one group $R^{14}$ is $-C(=NOR^{15})R^{16}$.

In another embodiment, in Formula (III.c.4), at least one group $R^{14}$ is $-P(O)(OR^{15})R(OR^{16})$.

In another embodiment, in Formula (III.c.4), at least one group $R^{14}$ is $-N(R^{15})(R^{16})$.

In another embodiment, in Formula (III.c.4), at least one group $R^{14}$ is $-N(R^{15})C(O)R^{16}$.

In another embodiment, in Formula (III.c.4), at least one group $R^{14}$ is $-N(R^{15})S(O)R^{16}$.

In another embodiment, in Formula (III.c.4), at least one group $R^{14}$ is $-N(R^{15})S(O)_2R^{16}$.

In another embodiment, in Formula (III.c.4), at least one group $R^{14}$ is $-N(R^{15})S(O)_2N(R^{16})(R^{17})$.

In another embodiment, in Formula (III.c.4), at least one group $R^{14}$ is $-N(R^{15})S(O)N(R^{16})(R^{17})$.

In another embodiment, in Formula (III.c.4), at least one group $R^{14}$ is $-N(R^{15})C(O)N(R^{16})(R^{17})$.

In another embodiment, in Formula (III.c.4), at least one group $R^{14}$ is $-N(R^{15})C(O)OR^{16}$.

In another embodiment, the present invention provides a compound, or a stereoisomer, tautomer, or pharmaceutically acceptable salt or solvate thereof, having the general structure shown in Formula (III.c.4A):

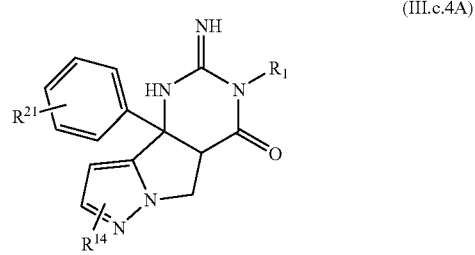

(III.c.4A)

wherein $R^1$, $R^{14}$, and $R^{21}$ are selected independently and $R^1$ and $R^{14}$ are as defined in Formula (III.c.4) and $R^{21}$ is as defined in Formula (I).

In another embodiment, the present invention provides a compound, or a stereoisomer, tautomer, or pharmaceutically acceptable salt or solvate thereof, having the general structure shown in Formula (III.c.5):

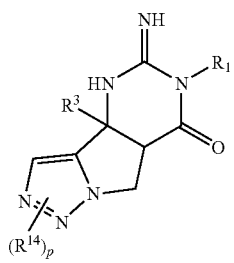

(III.c.5)

wherein $R^1$, $R^3$, $R^{14}$, and p are selected independently, and wherein p is 0-2 and $R^1$, $R^3$, $R^{14}$ are as defined in Formula (I).

In another embodiment, in Formula (III.c.5), $R^1$ is alkyl.

In another embodiment, in Formula (III.c.5), $R^1$ is methyl.

In another embodiment, in Formula (III.c.5), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.5), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.5), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.5), $R^3$ is heteroaryl or aryl.

In another embodiment, in Formula (III.c.5), $R^3$ is

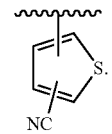

In another embodiment, in Formula (III.c.5), $R^3$ is

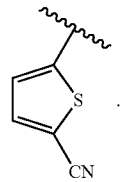

In another embodiment, in Formula (III.c.5), $R^3$ is

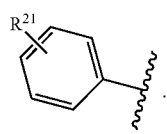

In another embodiment, in Formula (III.c.5), $R^3$ is

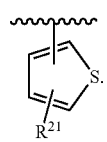

In another embodiment, in Formula (III.c.5), p is 0 (and $R^{14}$ is not present).

In another embodiment, in Formula (III.c.5), p is 1.
In another embodiment, in Formula (III.c.5), p is 2.
In another embodiment, in Formula (III.c.5), p is 3.
In another embodiment, in Formula (III.c.5), p is 4.
In another embodiment, in Formula (III.c.5), p is 5.
In another embodiment, in Formula (III.c.5), p is 2-5 and at least two groups $R^{14}$ are bound to the same ring atom.

In another embodiment, in Formula (III.c.5), at least one group $R^{14}$ is H.

In another embodiment, in Formula (III.c.5), at least one group $R^{14}$ is alkyl.

In another embodiment, in Formula (III.c.5), at least one group $R^{14}$ is arylalkyl.

In another embodiment, in Formula (III.c.5), at least one group $R^{14}$ is heteroarylalkyl.

In another embodiment, in Formula (III.c.5), at least one group $R^{14}$ is cycloalkylalkyl.

In another embodiment, in Formula (III.c.5), at least one group $R^{14}$ is heterocycloalkylalkyl.

In another embodiment, in Formula (III.c.5), at least one group $R^{14}$ is arylcycloalkylalkyl.

In another embodiment, in Formula (III.c.5), at least one group $R^{14}$ is heteroarylcycloalkylalkyl.

In another embodiment, in Formula (III.c.5), at least one group $R^{14}$ is arylheterocycloalkylalkyl.

In another embodiment, in Formula (III.c.5), at least one group $R^{14}$ is heteroarylheterocycloalkylalkyl.

In another embodiment, in Formula (III.c.5), at least one group $R^{14}$ is cycloalkyl.

In another embodiment, in Formula (III.c.5), at least one group $R^{14}$ is arylcycloalkyl.

In another embodiment, in Formula (III.c.5), at least one group $R^{14}$ is heteroarylcycloalkyl.

In another embodiment, in Formula (III.c.5), at least one group $R^{14}$ is heterocycloalkyl.

In another embodiment, in Formula (III.c.5), at least one group $R^{14}$ is arylheterocycloalkyl.

In another embodiment, in Formula (III.c.5), at least one group $R^{14}$ is heteroarylheterocycloalkyl.

In another embodiment, in Formula (III.c.5), at least one group $R^{14}$ is alkenyl.

In another embodiment, in Formula (III.c.5), at least one group $R^{14}$ is arylalkenyl.

In another embodiment, in Formula (III.c.5), at least one group $R^{14}$ is cycloalkenyl.

In another embodiment, in Formula (III.c.5), at least one group $R^{14}$ is arylcycloalkenyl.

In another embodiment, in Formula (III.c.5), at least one group $R^{14}$ is heteroarylcycloalkenyl.

In another embodiment, in Formula (III.c.5), at least one group $R^{14}$ is heterocycloalkenyl.

In another embodiment, in Formula (III.c.5), at least one group $R^{14}$ is arylheterocycloalkenyl.

In another embodiment, in Formula (III.c.5), at least one group $R^{14}$ is heteroarylheterocycloalkenyl.

In another embodiment, in Formula (III.c.5), at least one group $R^{14}$ is alkynyl.

In another embodiment, in Formula (III.c.5), at least one group $R^{14}$ is arylalkynyl.

In another embodiment, in Formula (III.c.5), at least one group $R^{14}$ is aryl.

In another embodiment, in Formula (III.c.5), at least one group $R^{14}$ is cycloalkylaryl.

In another embodiment, in Formula (III.c.5), at least one group $R^{14}$ is heterocycloalkylaryl.

In another embodiment, in Formula (III.c.5), at least one group $R^{14}$ is cycloalkenylaryl.

In another embodiment, in Formula (III.c.5), at least one group $R^{14}$ is heterocycloalkenylaryl.

In another embodiment, in Formula (III.c.5), at least one group $R^{14}$ is heteroaryl.

In another embodiment, in Formula (III.c.5), at least one group $R^{14}$ is cycloalkylheteroaryl.

In another embodiment, in Formula (III.c.5), at least one group $R^{14}$ is heterocycloalkylheteroaryl.

In another embodiment, in Formula (III.c.5), at least one group $R^{14}$ is cycloalkenylheteroaryl.

In another embodiment, in Formula (III.c.5), at least one group $R^{14}$ is heterocycloalkenylheteroaryl.

In another embodiment, in Formula (III.c.5), at least one group $R^{14}$ is halo.

In another embodiment, in Formula (III.c.5), at least one group $R^{14}$ is —$CH_2$—O—Si$(R^9)(R^{10})(R^{19})$.

In another embodiment, in Formula (III.c.5), at least one group $R^{14}$ is —N$(R^{15})$C(O)N$(R^{16})(R^{17})$.

In another embodiment, in Formula (III.c.5), at least one group $R^{14}$ is —CN.

In another embodiment, in Formula (III.c.5), at least one group $R^{14}$ is —OR$^{15}$.

In another embodiment, in Formula (III.c.5), at least one group $R^{14}$ is —C(O)R$^{15}$.

In another embodiment, in Formula (III.c.5), at least one group $R^{14}$ is —C(O)OR$^{15}$.

In another embodiment, in Formula (III.c.5), at least one group $R^{14}$ is —C(O)N$(R^{15})(R^{16})$.

In another embodiment, in Formula (III.c.5), at least one group $R^{14}$ is —SR$^{15}$.

In another embodiment, in Formula (III.c.5), at least one group $R^{14}$ is —S(O)N$(R^{15})(R^{16})$.

In another embodiment, in Formula (III.c.5), at least one group $R^{14}$ is —S(O)$_2$N$(R^{15})(R^{16})$.

In another embodiment, in Formula (III.c.5), at least one group $R^{14}$ is —C(=NOR$^{15}$)R$^{16}$.

In another embodiment, in Formula (III.c.5), at least one group $R^{14}$ is —P(O)(OR$^{15}$)(OR$^{16}$).

In another embodiment, in Formula (III.c.5), at least one group $R^{14}$ is —N$(R^{15})(R^{16})$.

In another embodiment, in Formula (III.c.5), at least one group $R^{14}$ is —N$(R^{15})$C(O)R$^{16}$.

In another embodiment, in Formula (III.c.5), at least one group $R^{14}$ is —N$(R^{15})$S(O)R$^{16}$.

In another embodiment, in Formula (III.c.5), at least one group $R^{14}$ is —N$(R^{15})$S(O)$_2$R$^{16}$.

In another embodiment, in Formula (III.c.5), at least one group $R^{14}$ is —N$(R^{15})$S(O)$_2$N$(R^{16})(R^{17})$.

In another embodiment, in Formula (III.c.5), at least one group $R^{14}$ is —N$(R^{15})$S(O)N$(R^{16})(R^{17})$.

In another embodiment, in Formula (III.c.5), at least one group $R^{14}$ is —N$(R^{15})$C(O)N$(R^{16})(R^{17})$.

In another embodiment, in Formula (III.c.5), at least one group $R^{14}$ is —N$(R^{15})$C(O)OR$^{16}$.

In another embodiment, the present invention provides a compound, or a stereoisomer, tautomer, or pharmaceutically acceptable salt or solvate thereof, having the general structure shown in Formula (III.c.5A):

(III.c.5A)

wherein $R^1$, $R^{14}$, and $R^{21}$ are selected independently and $R^1$ and $R^{14}$ are as defined in Formula (III.c.5) and $R^{21}$ is as defined in Formula (I).

In another embodiment, the present invention provides a compound, or a stereoisomer, tautomer, or pharmaceutically acceptable salt or solvate thereof, having the general structure shown in Formula (III.c.6):

(III.c.6)

wherein $R^1$, $R^3$, $R^{14}$, and p are selected independently, and wherein p is 0-2 and $R^1$, $R^3$, $R^{14}$ are as defined in Formula (I).

In another embodiment, in Formula (III.c.6), $R^1$ is alkyl.

In another embodiment, in Formula (III.c.6), $R^1$ is methyl.

In another embodiment, in Formula (III.c.6), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkylaryl, heteroaryl, cycloalkylheteroaryl, heterocycloalkylheteroaryl, cycloalkenylaryl or heterocycloalkenylaryl.

In another embodiment, in Formula (III.c.6), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.6), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.6), $R^3$ is heteroaryl or aryl.

In another embodiment, in Formula (III.c.6), $R^3$ is

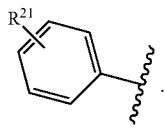

In another embodiment, in Formula (III.c.6), $R^3$ is

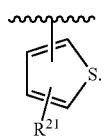

In another embodiment, in Formula (III.c.6), $R^3$ is

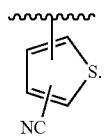

In another embodiment, in Formula (III.c.6), $R^3$ is

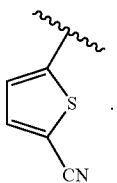

In another embodiment, in Formula (III.c.6), p is 0 (and $R^{14}$ is not present).
In another embodiment, in Formula (III.c.6), p is 1.
In another embodiment, in Formula (III.c.6), p is 2.
In another embodiment, in Formula (III.c.6), p is 3.
In another embodiment, in Formula (III.c.6), p is 4.
In another embodiment, in Formula (III.c.6), p is 5.
In another embodiment, in Formula (III.c.6), p is 2-5 and at least two groups $R^{14}$ are bound to the same ring atom.
In another embodiment, in Formula (III.c.6), at least one group $R^{14}$ is H.
In another embodiment, in Formula (III.c.6), at least one group $R^{14}$ is alkyl.
In another embodiment, in Formula (III.c.6), at least one group $R^{14}$ is arylalkyl.
In another embodiment, in Formula (III.c.6), at least one group $R^{14}$ is heteroarylalkyl.
In another embodiment, in Formula (III.c.6), at least one group $R^{14}$ is cycloalkylalkyl.
In another embodiment, in Formula (III.c.6), at least one group $R^{14}$ is heterocycloalkylalkyl.
In another embodiment, in Formula (III.c.6), at least one group $R^{14}$ is arylcycloalkylalkyl.
In another embodiment, in Formula (III.c.6), at least one group $R^{14}$ is heteroarylcycloalkylalkyl.
In another embodiment, in Formula (III.c.6), at least one group $R^{14}$ is arylheterocycloalkylalkyl.
In another embodiment, in Formula (III.c.6), at least one group $R^{14}$ is heteroarylheterocycloalkylalkyl.
In another embodiment, in Formula (III.c.6), at least one group $R^{14}$ is cycloalkyl.
In another embodiment, in Formula (III.c.6), at least one group $R^{14}$ is arylcycloalkyl.
In another embodiment, in Formula (III.c.6), at least one group $R^{14}$ is heteroarylcycloalkyl.
In another embodiment, in Formula (III.c.6), at least one group $R^{14}$ is heterocycloalkyl.
In another embodiment, in Formula (III.c.6), at least one group $R^{14}$ is arylheterocycloalkyl.
In another embodiment, in Formula (III.c.6), at least one group $R^{14}$ is heteroarylheterocycloalkyl.
In another embodiment, in Formula (III.c.6), at least one group $R^{14}$ is alkenyl.
In another embodiment, in Formula (III.c.6), at least one group $R^{14}$ is arylalkenyl.
In another embodiment, in Formula (III.c.6), at least one group $R^{14}$ is cycloalkenyl.
In another embodiment, in Formula (III.c.6), at least one group $R^{14}$ is arylcycloalkenyl.
In another embodiment, in Formula (III.c.6), at least one group $R^{14}$ is heteroarylcycloalkenyl.
In another embodiment, in Formula (III.c.6), at least one group $R^{14}$ is heterocycloalkenyl.
In another embodiment, in Formula (III.c.6), at least one group $R^{14}$ is arylheterocycloalkenyl.
In another embodiment, in Formula (III.c.6), at least one group $R^{14}$ is heteroarylheterocycloalkenyl.
In another embodiment, in Formula (III.c.6), at least one group $R^{14}$ is alkynyl.
In another embodiment, in Formula (III.c.6), at least one group $R^{14}$ is arylalkynyl.
In another embodiment, in Formula (III.c.6), at least one group $R^{14}$ is aryl.
In another embodiment, in Formula (III.c.6), at least one group $R^{14}$ is cycloalkylaryl.
In another embodiment, in Formula (III.c.6), at least one group $R^{14}$ is heterocycloalkylaryl.
In another embodiment, in Formula (III.c.6), at least one group $R^{14}$ is cycloalkenylaryl.
In another embodiment, in Formula (III.c.6), at least one group $R^{14}$ is heterocycloalkenylaryl.
In another embodiment, in Formula (III.c.6), at least one group $R^{14}$ is heteroaryl.
In another embodiment, in Formula (III.c.6), at least one group $R^{14}$ is cycloalkylheteroaryl.
In another embodiment, in Formula (III.c.6), at least one group $R^{14}$ is heterocycloalkylheteroaryl.
In another embodiment, in Formula (III.c.6), at least one group $R^{14}$ is cycloalkenylheteroaryl.

In another embodiment, in Formula (III.c.6), at least one group $R^{14}$ is heterocycloalkenylheteroaryl.

In another embodiment, in Formula (III.c.6), at least one group $R^{14}$ is halo.

In another embodiment, in Formula (III.c.6), at least one group $R^{14}$ is —$CH_2$—O—$Si(R^9)(R^{10})(R^{19})$.

In another embodiment, in Formula (III.c.6), at least one group $R^{14}$ is —$N(R^{15})C(O)N(R^{16})(R^{17})$.

In another embodiment, in Formula (III.c.6), at least one group $R^{14}$ is —CN.

In another embodiment, in Formula (III.c.6), at least one group $R^{14}$ is —$OR^{15}$.

In another embodiment, in Formula (III.c.6), at least one group $R^{14}$ is —$C(O)R^{15}$.

In another embodiment, in Formula (III.c.6), at least one group $R^{14}$ is —$C(O)OR^{15}$.

In another embodiment, in Formula (III.c.6), at least one group $R^{14}$ is —$C(O)N(R^{15})(R^{16})$.

In another embodiment, in Formula (III.c.6), at least one group $R^{14}$ is —$SR^{15}$.

In another embodiment, in Formula (III.c.6), at least one group $R^{14}$ is —$S(O)N(R^{15})(R^{16})$.

In another embodiment, in Formula (III.c.6), at least one group $R^{14}$ is —$S(O)_2N(R^{15})(R^{16})$.

In another embodiment, in Formula (III.c.6), at least one group $R^{14}$ is —$C(=NOR^{15})R^{16}$.

In another embodiment, in Formula (III.c.6), at least one group $R^{14}$ is —$P(O)(OR^{15})(OR^{16})$.

In another embodiment, in Formula (III.c.6), at least one group $R^{14}$ is —$N(R^{15})(R^{16})$.

In another embodiment, in Formula (III.c.6), at least one group $R^{14}$ is —$N(R^{15})C(O)R^{16}$.

In another embodiment, in Formula (III.c.6), at least one group $R^{14}$ is —$N(R^{15})S(O)R^{16}$.

In another embodiment, in Formula (III.c.6), at least one group $R^{14}$ is —$N(R^{15})S(O)_2R^{16}$.

In another embodiment, in Formula (III.c.6), at least one group $R^{14}$ is —$N(R^{15})S(O)_2N(R^{16})(R^{17})$.

In another embodiment, in Formula (III.c.6), at least one group $R^{14}$ is —$N(R^{15})S(O)N(R^{16})(R^{17})$.

In another embodiment, in Formula (III.c.6), at least one group $R^{14}$ is —$N(R^{15})C(O)N(R^{16})(R^{17})$.

In another embodiment, in Formula (III.c.6), at least one group $R^{14}$ is —$N(R^{15})C(O)OR^{16}$.

In another embodiment, the present invention provides a compound, or a stereoisomer, tautomer, or pharmaceutically acceptable salt or solvate thereof, having the general structure shown in Formula (III.c.6A):

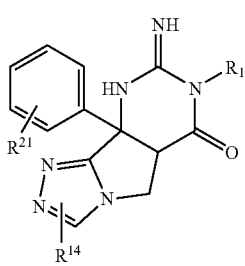

(III.c.6A)

wherein $R^1$, $R^{14}$, and $R^{21}$ are selected independently and $R^1$ and $R^{14}$ are as defined in Formula (III.c.6) and $R^{21}$ is as defined in Formula (I).

In another embodiment, the present invention provides a compound, or a stereoisomer, tautomer, or pharmaceutically acceptable salt or solvate thereof, having the general structure shown in Formula (III.c.7):

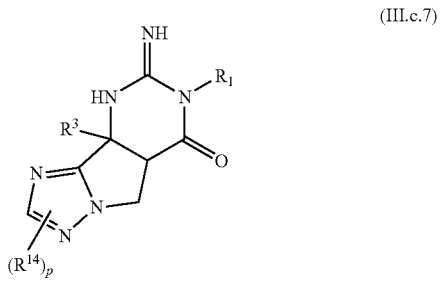

(III.c.7)

wherein $R^1$, $R^3$, $R^{14}$, and p are selected independently, and wherein p is 0-2 and $R^1$, $R^3$, $R^{14}$ are as defined in Formula (I).

In another embodiment, in Formula (III.c.7), $R^1$ is alkyl.

In another embodiment, in Formula (III.c.7), $R^1$ is methyl.

In another embodiment, in Formula (III.c.7), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.7), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.7), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.7), $R^3$ is heteroaryl or aryl.

In another embodiment, in Formula (III.c.7), $R^3$ is

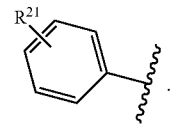

In another embodiment, in Formula (III.c.7), $R^3$ is

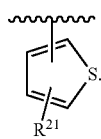

In another embodiment, in Formula (III.c.7), $R^3$ is

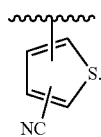

In another embodiment, in Formula (III.c.7), $R^3$ is

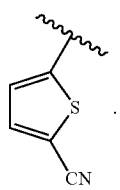

In another embodiment, in Formula (III.c.7), p is 0 (and $R^{14}$ is not present).

In another embodiment, in Formula (III.c.7), p is 1.
In another embodiment, in Formula (III.c.7), p is 2.
In another embodiment, in Formula (III.c.7), p is 3.
In another embodiment, in Formula (III.c.7), p is 4.
In another embodiment, in Formula (III.c.7), p is 5.
In another embodiment, in Formula (III.c.7), p is 2-5 and at least two groups $R^{14}$ are bound to the same ring atom.
In another embodiment, in Formula (III.c.7), at least one group $R^{14}$ is H.
In another embodiment, in Formula (III.c.7), at least one group $R^{14}$ is alkyl.
In another embodiment, in Formula (III.c.7), at least one group $R^{14}$ is arylalkyl.
In another embodiment, in Formula (III.c.7), at least one group $R^{14}$ is heteroarylalkyl.
In another embodiment, in Formula (III.c.7), at least one group $R^{14}$ is cycloalkylalkyl.
In another embodiment, in Formula (III.c.7), at least one group $R^{14}$ is heterocycloalkylalkyl.
In another embodiment, in Formula (III.c.7), at least one group $R^{14}$ is arylcycloalkylalkyl.
In another embodiment, in Formula (III.c.7), at least one group $R^{14}$ is heteroarylcycloalkylalkyl.
In another embodiment, in Formula (III.c.7), at least one group $R^{14}$ is arylheterocycloalkylalkyl.
In another embodiment, in Formula (III.c.7), at least one group $R^{14}$ is heteroarylheterocycloalkylalkyl.
In another embodiment, in Formula (III.c.7), at least one group $R^{14}$ is cycloalkyl.
In another embodiment, in Formula (III.c.7), at least one group $R^{14}$ is arylcycloalkyl.
In another embodiment, in Formula (III.c.7), at least one group $R^{14}$ is heteroarylcycloalkyl.
In another embodiment, in Formula (III.c.7), at least one group $R^{14}$ is heterocycloalkyl.
In another embodiment, in Formula (III.c.7), at least one group $R^{14}$ is arylheterocycloalkyl.
In another embodiment, in Formula (III.c.7), at least one group $R^{14}$ is heteroarylheterocycloalkyl.
In another embodiment, in Formula (III.c.7), at least one group $R^{14}$ is alkenyl.
In another embodiment, in Formula (III.c.7), at least one group $R^{14}$ is arylalkenyl.
In another embodiment, in Formula (III.c.7), at least one group $R^{14}$ is cycloalkenyl.
In another embodiment, in Formula (III.c.7), at least one group $R^{14}$ is arylcycloalkenyl.
In another embodiment, in Formula (III.c.7), at least one group $R^{14}$ is heteroarylcycloalkenyl.
In another embodiment, in Formula (III.c.7), at least one group $R^{14}$ is heterocycloalkenyl.
In another embodiment, in Formula (III.c.7), at least one group $R^{14}$ is arylheterocycloalkenyl.
In another embodiment, in Formula (III.c.7), at least one group $R^{14}$ is heteroarylheterocycloalkenyl.
In another embodiment, in Formula (III.c.7), at least one group $R^{14}$ is alkynyl.
In another embodiment, in Formula (III.c.7), at least one group $R^{14}$ is arylalkynyl.
In another embodiment, in Formula (III.c.7), at least one group $R^{14}$ is aryl.
In another embodiment, in Formula (III.c.7), at least one group $R^{14}$ is cycloalkylaryl.
In another embodiment, in Formula (III.c.7), at least one group $R^{14}$ is heterocycloalkylaryl.
In another embodiment, in Formula (III.c.7), at least one group $R^{14}$ is cycloalkenylaryl.
In another embodiment, in Formula (III.c.7), at least one group $R^{14}$ is heterocycloalkenylaryl.
In another embodiment, in Formula (III.c.7), at least one group $R^{14}$ is heteroaryl.
In another embodiment, in Formula (III.c.7), at least one group $R^{14}$ is cycloalkylheteroaryl.
In another embodiment, in Formula (III.c.7), at least one group $R^{14}$ is heterocycloalkylheteroaryl.
In another embodiment, in Formula (III.c.7), at least one group $R^{14}$ is cycloalkenylheteroaryl.
In another embodiment, in Formula (III.c.7), at least one group $R^{14}$ is heterocycloalkenylheteroaryl.
In another embodiment, in Formula (III.c.7), at least one group $R^{14}$ is halo.
In another embodiment, in Formula (III.c.7), at least one group $R^{14}$ is —$CH_2$—O—Si($R^9$)($R^{10}$)($R^{19}$).
In another embodiment, in Formula (III.c.7), at least one group $R^{14}$ is —N($R^{15}$)C(O)N($R^{16}$)($R^{17}$).
In another embodiment, in Formula (III.c.7), at least one group $R^{14}$ is —CN.
In another embodiment, in Formula (III.c.7), at least one group $R^{14}$ is —$OR^{15}$.
In another embodiment, in Formula (III.c.7), at least one group $R^{14}$ is —C(O)$R^{15}$.
In another embodiment, in Formula (III.c.7), at least one group $R^{14}$ is —C(O)O$R^{15}$.
In another embodiment, in Formula (III.c.7), at least one group $R^{14}$ is —C(O)N($R^{15}$)($R^{16}$).
In another embodiment, in Formula (III.c.7), at least one group $R^{14}$ is —$SR^{15}$.
In another embodiment, in Formula (III.c.7), at least one group $R^{14}$ is —S(O)N($R^{15}$)($R^{16}$).
In another embodiment, in Formula (III.c.7), at least one group $R^{14}$ is —S(O)$_2$N($R^{15}$)($R^{16}$).

In another embodiment, in Formula (III.c.7), at least one group $R^{14}$ is —C(=NOR$^{15}$)R$^{16}$.

In another embodiment, in Formula (III.c.7), at least one group $R^{14}$ is —P(O)(OR$^{15}$)(OR$^{16}$).

In another embodiment, in Formula (III.c.7), at least one group $R^{14}$ is —N(R$^{15}$)(R$^{16}$).

In another embodiment, in Formula (III.c.7), at least one group $R^{14}$ is —N(R$^{15}$)C(O)R$^{16}$.

In another embodiment, in Formula (III.c.7), at least one group $R^{14}$ is —N(R$^{15}$)S(O)R$^{16}$.

In another embodiment, in Formula (III.c.7), at least one group $R^{14}$ is —N(R$^{15}$)S(O)$_2$R$^{16}$.

In another embodiment, in Formula (III.c.7), at least one group $R^{14}$ is —N(R$^{15}$)S(O)$_2$N(R$^{16}$)(R$^{17}$).

In another embodiment, in Formula (III.c.7), at least one group $R^{14}$ is —N(R$^{15}$)S(O)N(R$^{16}$)(R$^{17}$).

In another embodiment, in Formula (III.c.7), at least one group $R^{14}$ is —N(R$^{15}$)C(O)N(R$^{16}$)(R$^{17}$).

In another embodiment, in Formula (III.c.7), at least one group $R^{14}$ is —N(R$^{15}$)C(O)OR$^{16}$.

In another embodiment, the present invention provides a compound, or a stereoisomer, tautomer, or pharmaceutically acceptable salt or solvate thereof, having the general structure shown in Formula (III.c.7A):

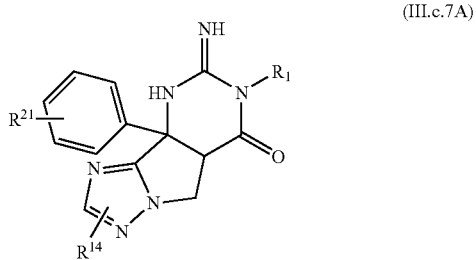

(III.c.7A)

wherein $R^1$, $R^{14}$, and $R^{21}$ are selected independently and $R^1$ and $R^{14}$ are as defined in Formula (III.c.7) and $R^{21}$ is as defined in Formula (I).

In another embodiment, the present invention provides a compound, or a stereoisomer, tautomer, or pharmaceutically acceptable salt or solvate thereof, having the general structure shown in Formula (III.c.8):

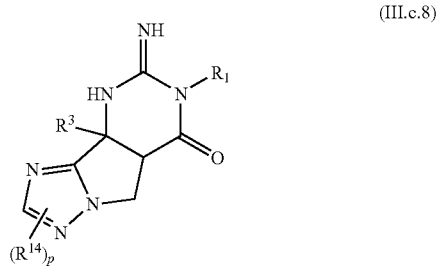

(III.c.8)

wherein $R^1$, $R^3$, $R^{14}$, and p are selected independently, and wherein p is 0-2 and $R^1$, $R^3$, $R^{14}$ are as defined in Formula (I).

In another embodiment, in Formula (III.c.8), $R^1$ is alkyl.

In another embodiment, in Formula (III.c.8), $R^1$ is methyl.

In another embodiment, in Formula (III.c.8), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.8), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.8), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.8), $R^3$ is heteroaryl or aryl.

In another embodiment, in Formula (III.c.8), $R^3$ is

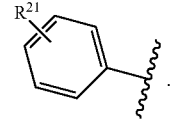

In another embodiment, in Formula (III.c.8), $R^3$ is

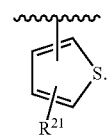

In another embodiment, in Formula (III.c.8), $R^3$ is

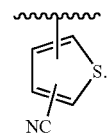

In another embodiment, in Formula (III.c.8), $R^3$ is

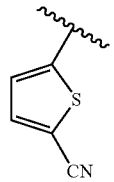

In another embodiment, in Formula (III.c.8), p is 0 (and $R^{14}$ is not present).

In another embodiment, in Formula (III.c.8), p is 1.

In another embodiment, in Formula (III.c.8), p is 2.

In another embodiment, in Formula (III.c.8), p is 3.

In another embodiment, in Formula (III.c.8), p is 4.

In another embodiment, in Formula (III.c.8), p is 5.

In another embodiment, in Formula (III.c.8), p is 2-5 and at least two groups $R^{14}$ are bound to the same ring atom.

In another embodiment, in Formula (III.c.8), at least one group $R^{14}$ is H.

In another embodiment, in Formula (III.c.8), at least one group $R^{14}$ is alkyl.

In another embodiment, in Formula (III.c.8), at least one group $R^{14}$ is arylalkyl.

In another embodiment, in Formula (III.c.8), at least one group $R^{14}$ is heteroarylalkyl.

In another embodiment, in Formula (III.c.8), at least one group $R^{14}$ is cycloalkylalkyl.

In another embodiment, in Formula (III.c.8), at least one group $R^{14}$ is heterocycloalkylalkyl.

In another embodiment, in Formula (III.c.8), at least one group $R^{14}$ is arylcycloalkylalkyl.

In another embodiment, in Formula (III.c.8), at least one group $R^{14}$ is heteroarylcycloalkylalkyl.

In another embodiment, in Formula (III.c.8), at least one group $R^{14}$ is arylheterocycloalkylalkyl.

In another embodiment, in Formula (III.c.8), at least one group $R^{14}$ is heteroarylheterocycloalkylalkyl.

In another embodiment, in Formula (III.c.8), at least one group $R^{14}$ is cycloalkyl.

In another embodiment, in Formula (III.c.8), at least one group $R^{14}$ is arylcycloalkyl.

In another embodiment, in Formula (III.c.8), at least one group $R^{14}$ is heteroarylcycloalkyl.

In another embodiment, in Formula (III.c.8), at least one group $R^{14}$ is heterocycloalkyl.

In another embodiment, in Formula (III.c.8), at least one group $R^{14}$ is arylheterocycloalkyl.

In another embodiment, in Formula (III.c.8), at least one group $R^{14}$ is heteroarylheterocycloalkyl.

In another embodiment, in Formula (III.c.8), at least one group $R^{14}$ is alkenyl.

In another embodiment, in Formula (III.c.8), at least one group $R^{14}$ is arylalkenyl.

In another embodiment, in Formula (III.c.8), at least one group $R^{14}$ is cycloalkenyl.

In another embodiment, in Formula (III.c.8), at least one group $R^{14}$ is arylcycloalkenyl.

In another embodiment, in Formula (III.c.8), at least one group $R^{14}$ is heteroarylcycloalkenyl.

In another embodiment, in Formula (III.c.8), at least one group $R^{14}$ is heterocycloalkenyl.

In another embodiment, in Formula (III.c.8), at least one group $R^{14}$ is arylheterocycloalkenyl.

In another embodiment, in Formula (III.c.8), at least one group $R^{14}$ is heteroarylheterocycloalkenyl.

In another embodiment, in Formula (III.c.8), at least one group $R^{14}$ is alkynyl.

In another embodiment, in Formula (III.c.8), at least one group $R^{14}$ is arylalkynyl.

In another embodiment, in Formula (III.c.8), at least one group $R^{14}$ is aryl.

In another embodiment, in Formula (III.c.8), at least one group $R^{14}$ is cycloalkylaryl.

In another embodiment, in Formula (III.c.8), at least one group $R^{14}$ is heterocycloalkylaryl.

In another embodiment, in Formula (III.c.8), at least one group $R^{14}$ is cycloalkenylaryl.

In another embodiment, in Formula (III.c.8), at least one group $R^{14}$ is heterocycloalkenylaryl.

In another embodiment, in Formula (III.c.8), at least one group $R^{14}$ is heteroaryl.

In another embodiment, in Formula (III.c.8), at least one group $R^{14}$ is cycloalkylheteroaryl.

In another embodiment, in Formula (III.c.8), at least one group $R^{14}$ is heterocycloalkylheteroaryl.

In another embodiment, in Formula (III.c.8), at least one group $R^{14}$ is cycloalkenylheteroaryl.

In another embodiment, in Formula (III.c.8), at least one group $R^{14}$ is heterocycloalkenylheteroaryl.

In another embodiment, in Formula (III.c.8), at least one group $R^{14}$ is halo.

In another embodiment, in Formula (III.c.8), at least one group $R^{14}$ is —$CH_2$—O—$Si(R^9)(R^{10})(R^{19})$.

In another embodiment, in Formula (III.c.8), at least one group $R^{14}$ is —$N(R^{15})C(O)N(R^{16})(R^{17})$.

In another embodiment, in Formula (III.c.8), at least one group $R^{14}$ is —CN.

In another embodiment, in Formula (III.c.8), at least one group $R^{14}$ is —$OR^{15}$.

In another embodiment, in Formula (III.c.8), at least one group $R^{14}$ is —$C(O)R^{15}$.

In another embodiment, in Formula (III.c.8), at least one group $R^{14}$ is —$C(O)OR^{15}$.

In another embodiment, in Formula (III.c.8), at least one group $R^{14}$ is —$C(O)N(R^{15})(R^{16})$.

In another embodiment, in Formula (III.c.8), at least one group $R^{14}$ is —$SR^{15}$.

In another embodiment, in Formula (III.c.8), at least one group $R^{14}$ is —$S(O)N(R^{15})(R^{16})$.

In another embodiment, in Formula (III.c.8), at least one group $R^{14}$ is —$S(O)_2N(R^{15})(R^{16})$.

In another embodiment, in Formula (III.c.8), at least one group $R^{14}$ is —$C(=NOR^{15})R^{16}$.

In another embodiment, in Formula (III.c.8), at least one group $R^{14}$ is —$P(O)(OR^{15})(OR^{16})$.

In another embodiment, in Formula (III.c.8), at least one group $R^{14}$ is —$N(R^{15})(R^{16})$.

In another embodiment, in Formula (III.c.8), at least one group $R^{14}$ is —$N(R^{15})C(O)R^{16}$.

In another embodiment, in Formula (III.c.8), at least one group $R^{14}$ is —$N(R^{15})S(O)R^{16}$.

In another embodiment, in Formula (III.c.8), at least one group $R^{14}$ is —$N(R^{15})S(O)_2R^{16}$.

In another embodiment, in Formula (III.c.8), at least one group $R^{14}$ is —$N(R^{15})S(O)_2N(R^{16})(R^{17})$.

In another embodiment, in Formula (III.c.8), at least one group $R^{14}$ is —$N(R^{15})S(O)N(R^{16})(R^{17})$.

In another embodiment, in Formula (III.c.8), at least one group $R^{14}$ is —$N(R^{15})C(O)N(R^{16})(R^{17})$.

In another embodiment, in Formula (III.c.8), at least one group $R^{14}$ is —$N(R^{15})C(O)OR^{16}$.

In another embodiment, the present invention provides a compound, or a stereoisomer, tautomer, or pharmaceutically acceptable salt or solvate thereof, having the general structure shown in Formula (III.c.8A):

(III.c.8A)

wherein $R^1$, $R^{14}$, and $R^{21}$ are selected independently and $R^1$ and $R^{14}$ are as defined in Formula (III.c.8) and $R^{21}$ is as defined in Formula (I).

In another embodiment, the present invention provides a compound, or a stereoisomer, tautomer, or pharmaceutically acceptable salt or solvate thereof, having the general structure shown in Formula (III.c.9):

(III.c.9)

wherein $R^1$, $R^3$, $R^{14}$, and p are selected independently, and wherein p is 0-2 and $R^1$, $R^3$, $R^{14}$ are as defined in Formula (I).

In another embodiment, in Formula (III.c.9), $R^1$ is alkyl.

In another embodiment, in Formula (III.c.9), $R^1$ is methyl.

In another embodiment, in Formula (III.c.9), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.9), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (III.c.9), $R^3$ is arylalkyl, heteroarylalkyl, arylcycloalkyl, heteroarylcycloalkyl, arylalkenyl, arylalkynyl, aryl or heteroaryl.

In another embodiment, in Formula (III.c.9), $R^3$ is heteroaryl or aryl.

In another embodiment, in Formula (III.c.9), $R^3$ is

In another embodiment, in Formula (III.c.9), $R^3$ is

In another embodiment, in Formula (III.c.9), $R^3$ is

In another embodiment, in Formula (III.c.9), $R^3$ is

In another embodiment, in Formula (III.c.9), p is 0 (and $R^{14}$ is not present).

In another embodiment, in Formula (III.c.9), p is 1.
In another embodiment, in Formula (III.c.9), p is 2.
In another embodiment, in Formula (III.c.9), p is 3.
In another embodiment, in Formula (III.c.9), p is 4.
In another embodiment, in Formula (III.c.9), p is 5.
In another embodiment, in Formula (III.c.9), p is 2-5 and at least two groups $R^{14}$ are bound to the same ring atom.

In another embodiment, in Formula (III.c.9), at least one group $R^{14}$ is H.
In another embodiment, in Formula (III.c.9), at least one group $R^{14}$ is alkyl.
In another embodiment, in Formula (III.c.9), at least one group $R^{14}$ is arylalkyl.
In another embodiment, in Formula (III.c.9), at least one group $R^{14}$ is heteroarylalkyl.
In another embodiment, in Formula (III.c.9), at least one group $R^{14}$ is cycloalkylalkyl.
In another embodiment, in Formula (III.c.9), at least one group $R^{14}$ is heterocycloalkylalkyl.
In another embodiment, in Formula (III.c.9), at least one group $R^{14}$ is arylcycloalkylalkyl.
In another embodiment, in Formula (III.c.9), at least one group $R^{14}$ is heteroarylcycloalkylalkyl.
In another embodiment, in Formula (III.c.9), at least one group $R^{14}$ is arylheterocycloalkylalkyl.

In another embodiment, in Formula (III.c.9), at least one group $R^{14}$ is heteroarylheterocycloalkylalkyl.

In another embodiment, in Formula (III.c.9), at least one group $R^{14}$ is cycloalkyl.

In another embodiment, in Formula (III.c.9), at least one group $R^{14}$ is arylcycloalkyl.

In another embodiment, in Formula (III.c.9), at least one group $R^{14}$ is heteroarylcycloalkyl.

In another embodiment, in Formula (III.c.9), at least one group $R^{14}$ is heterocycloalkyl.

In another embodiment, in Formula (III.c.9), at least one group $R^{14}$ is arylheterocycloalkyl.

In another embodiment, in Formula (III.c.9), at least one group $R^{14}$ is heteroarylheterocycloalkyl.

In another embodiment, in Formula (III.c.9), at least one group $R^{14}$ is alkenyl.

In another embodiment, in Formula (III.c.9), at least one group $R^{14}$ is arylalkenyl.

In another embodiment, in Formula (III.c.9), at least one group $R^{14}$ is cycloalkenyl.

In another embodiment, in Formula (III.c.9), at least one group $R^{14}$ is arylcycloalkenyl.

In another embodiment, in Formula (III.c.9), at least one group $R^{14}$ is heteroarylcycloalkenyl.

In another embodiment, in Formula (III.c.9), at least one group $R^{14}$ is heterocycloalkenyl.

In another embodiment, in Formula (III.c.9), at least one group $R^{14}$ is arylheterocycloalkenyl.

In another embodiment, in Formula (III.c.9), at least one group $R^{14}$ is heteroarylheterocycloalkenyl.

In another embodiment, in Formula (III.c.9), at least one group $R^{14}$ is alkynyl.

In another embodiment, in Formula (III.c.9), at least one group $R^{14}$ is arylalkynyl.

In another embodiment, in Formula (III.c.9), at least one group $R^{14}$ is aryl.

In another embodiment, in Formula (III.c.9), at least one group $R^{14}$ is cycloalkylaryl.

In another embodiment, in Formula (III.c.9), at least one group $R^{14}$ is heterocycloalkylaryl.

In another embodiment, in Formula (III.c.9), at least one group $R^{14}$ is cycloalkenylaryl.

In another embodiment, in Formula (III.c.9), at least one group $R^{14}$ is heterocycloalkenylaryl.

In another embodiment, in Formula (III.c.9), at least one group $R^{14}$ is heteroaryl.

In another embodiment, in Formula (III.c.9), at least one group $R^{14}$ is cycloalkylheteroaryl.

In another embodiment, in Formula (III.c.9), at least one group $R^{14}$ is heterocycloalkylheteroaryl.

In another embodiment, in Formula (III.c.9), at least one group $R^{14}$ is cycloalkenylheteroaryl.

In another embodiment, in Formula (III.c.9), at least one group $R^{14}$ is heterocycloalkenylheteroaryl.

In another embodiment, in Formula (III.c.9), at least one group $R^{14}$ is halo.

In another embodiment, in Formula (III.c.9), at least one group $R^{14}$ is —$CH_2$—O—Si($R^9$)($R^{10}$)($R^{19}$).

In another embodiment, in Formula (III.c.9), at least one group $R^{14}$ is —N($R^{15}$)C(O)N($R^{16}$)($R^{17}$).

In another embodiment, in Formula (III.c.9), at least one group $R^{14}$ is —CN.

In another embodiment, in Formula (III.c.9), at least one group $R^{14}$ is —$OR^{15}$.

In another embodiment, in Formula (III.c.9), at least one group $R^{14}$ is —C(O)$R^{15}$.

In another embodiment, in Formula (III.c.9), at least one group $R^{14}$ is —C(O)O$R^{15}$.

In another embodiment, in Formula (III.c.9), at least one group $R^{14}$ is —C(O)N($R^{15}$)($R^{16}$).

In another embodiment, in Formula (III.c.9), at least one group $R^{14}$ is —$SR^{15}$.

In another embodiment, in Formula (III.c.9), at least one group $R^{14}$ is —S(O)N($R^{15}$)($R^{16}$).

In another embodiment, in Formula (III.c.9), at least one group $R^{14}$ is —S(O)$_2$N($R^{15}$)($R^{16}$).

In another embodiment, in Formula (III.c.9), at least one group $R^{14}$ is —C(=NO$R^{15}$)$R^{16}$.

In another embodiment, in Formula (III.c.9), at least one group $R^{14}$ is —P(O)(O$R^{15}$)(O$R^{16}$).

In another embodiment, in Formula (III.c.9), at least one group $R^{14}$ is —N($R^{15}$)($R^{16}$).

In another embodiment, in Formula (III.c.9), at least one group $R^{14}$ is —N($R^{15}$)C(O)$R^{16}$.

In another embodiment, in Formula (III.c.9), at least one group $R^{14}$ is —N($R^{15}$)S(O)$R^{16}$.

In another embodiment, in Formula (III.c.9), at least one group $R^{14}$ is —N($R^{15}$)S(O)$_2$$R^{16}$.

In another embodiment, in Formula (III.c.9), at least one group $R^{14}$ is —N($R^{15}$)S(O)$_2$N($R^{16}$)($R^{17}$).

In another embodiment, in Formula (III.c.9), at least one group $R^{14}$ is —N($R^{15}$)S(O)N($R^{16}$)($R^{17}$).

In another embodiment, in Formula (III.c.9), at least one group $R^{14}$ is —N($R^{15}$)C(O)N($R^{16}$)($R^{17}$).

In another embodiment, in Formula (III.c.9), at least one group $R^{14}$ is —N($R^{15}$)C(O)O$R^{16}$.

In another embodiment, the present invention provides a compound, or a stereoisomer, tautomer, or pharmaceutically acceptable salt or solvate thereof, having the general structure shown in Formula (III.c.9A):

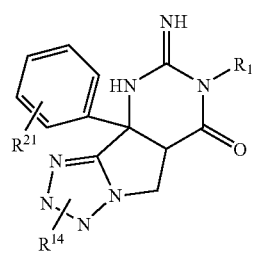

(III.c.9A)

wherein $R^1$, $R^{14}$, and $R^{21}$ are selected independently and $R^1$ and $R^{14}$ are as defined in Formula (III.c.9) and $R^{21}$ is as defined in Formula (I).

In another embodiment, the present invention provides a compound, or a stereoisomer, tautomer, or pharmaceutically acceptable salt or solvate thereof, having the general structure shown in Formula (IV):

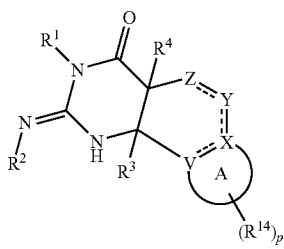
(IV)

wherein $R^1$, $R^2$, $R^3$, $R^4$, Z, Y, X, V, Ring A, p, and each $R^{14}$ is selected independently of each other and wherein:
ring A forms a mono or multicyclic 4 to 12 membered arylene ring, and $R^1$, $R^2$, $R^3$, $R^4$, Z, X, Y, V, $R^{14}$, and p are as defined in Formula I.

In another embodiment, in Formula (IV), V is a carbon atom and V, X, and ring A, and —$(R^{14})_p$ form

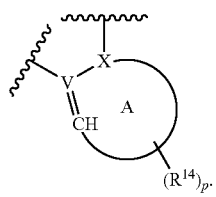

In another embodiment, in Formula (IV), V is a carbon atom and V, X, and ring A, and —$(R^{14})_p$ form

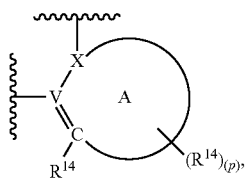

and p=0-4.

In another embodiment, in Formula (IV), —V=X— is

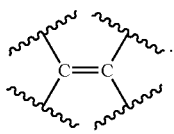

In another embodiment, in Formula (IV), $R^1$ is alkyl.
In another embodiment, in Formula (IV), $R^1$ is methyl.
In another embodiment, in Formula (IV), $R^2$ is H.
In another embodiment, in Formula (IV), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (IV), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (IV), $R^3$ is arylalkyl, heteroarylalkyl, arylcycloalkyl, heteroarylcycloalkyl, arylalkenyl, arylalkynyl, aryl or heteroaryl.

In another embodiment, in Formula (IV), $R^3$ is heteroaryl or aryl.

In another embodiment, in Formula (IV), $R^3$ is

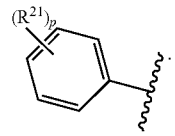

In another embodiment, in Formula (IV), $R^3$ is

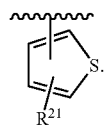

In another embodiment, in Formula (IV), $R^3$ is

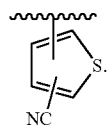

In another embodiment, in Formula (IV), $R^3$ is

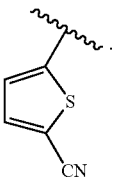

In another embodiment, in Formula (IV), $R^4$ is H.
In another embodiment, in Formula (IV), $R^4$ is alkyl.
In another embodiment, in Formula (IV), $R^4$ is halo.
In another embodiment, in Formula (IV), p is 0 (and $R^{14}$ is not present).
In another embodiment, in Formula (IV), p is 1.
In another embodiment, in Formula (IV), p is 2.
In another embodiment, in Formula (IV), p is 3.
In another embodiment, in Formula (IV), p is 4.
In another embodiment, in Formula (IV), p is 5.
In another embodiment, in Formula (IV), p is 2-5 and at least two groups $R^{14}$ are bound to the same ring atom.

In another embodiment, in Formula (IV), at least one group $R^{14}$ is H.

In another embodiment, in Formula (IV), at least one group $R^{14}$ is alkyl.

In another embodiment, in Formula (IV), at least one group $R^{14}$ is arylalkyl.

In another embodiment, in Formula (IV), at least one group $R^{14}$ is heteroarylalkyl.

In another embodiment, in Formula (IV), at least one group $R^{14}$ is cycloalkylalkyl.

In another embodiment, in Formula (IV), at least one group $R^{14}$ is heterocycloalkylalkyl.

In another embodiment, in Formula (IV), at least one group $R^{14}$ is arylcycloalkylalkyl.

In another embodiment, in Formula (IV), at least one group $R^{14}$ is heteroarylcycloalkylalkyl.

In another embodiment, in Formula (IV), at least one group $R^{14}$ is arylheterocycloalkylalkyl.

In another embodiment, in Formula (IV), at least one group $R^{14}$ is heteroarylheterocycloalkylalkyl.

In another embodiment, in Formula (IV), at least one group $R^{14}$ is cycloalkyl.

In another embodiment, in Formula (IV), at least one group $R^{14}$ is arylcycloalkyl.

In another embodiment, in Formula (IV), at least one group $R^{14}$ is heteroarylcycloalkyl.

In another embodiment, in Formula (IV), at least one group $R^{14}$ is heterocycloalkyl.

In another embodiment, in Formula (IV), at least one group $R^{14}$ is arylheterocycloalkyl.

In another embodiment, in Formula (IV), at least one group $R^{14}$ is heteroarylheterocycloalkyl.

In another embodiment, in Formula (IV), at least one group $R^{14}$ is alkenyl.

In another embodiment, in Formula (IV), at least one group $R^{14}$ is arylalkenyl.

In another embodiment, in Formula (IV), at least one group $R^{14}$ is cycloalkenyl.

In another embodiment, in Formula (IV), at least one group $R^{14}$ is arylcycloalkenyl.

In another embodiment, in Formula (IV), at least one group $R^{14}$ is heteroarylcycloalkenyl.

In another embodiment, in Formula (IV), at least one group $R^{14}$ is heterocycloalkenyl.

In another embodiment, in Formula (IV), at least one group $R^{14}$ is arylheterocycloalkenyl.

In another embodiment, in Formula (IV), at least one group $R^{14}$ is heteroarylheterocycloalkenyl.

In another embodiment, in Formula (IV), at least one group $R^{14}$ is alkynyl.

In another embodiment, in Formula (IV), at least one group $R^{14}$ is arylalkynyl.

In another embodiment, in Formula (IV), at least one group $R^{14}$ is aryl.

In another embodiment, in Formula (IV), at least one group $R^{14}$ is cycloalkylaryl.

In another embodiment, in Formula (IV), at least one group $R^{14}$ is heterocycloalkylaryl.

In another embodiment, in Formula (IV), at least one group $R^{14}$ is cycloalkenylaryl.

In another embodiment, in Formula (IV), at least one group $R^{14}$ is heterocycloalkenylaryl.

In another embodiment, in Formula (IV), at least one group $R^{14}$ is heteroaryl.

In another embodiment, in Formula (IV), at least one group $R^{14}$ is cycloalkylheteroaryl.

In another embodiment, in Formula (IV), at least one group $R^{14}$ is heterocycloalkylheteroaryl.

In another embodiment, in Formula (IV), at least one group $R^{14}$ is cycloalkenylheteroaryl.

In another embodiment, in Formula (IV), at least one group $R^{14}$ is heterocycloalkenylheteroaryl.

In another embodiment, in Formula (IV), at least one group $R^{14}$ is halo.

In another embodiment, in Formula (IV), at least one group $R^{14}$ is —$CH_2$—O—$Si(R^9)(R^{10})(R^{19})$.

In another embodiment, in Formula (IV), at least one group $R^{14}$ is —$N(R^{15})C(O)N(R^{16})(R^{17})$.

In another embodiment, in Formula (IV), at least one group $R^{14}$ is —CN.

In another embodiment, in Formula (IV), at least one group $R^{14}$ is —$OR^{15}$.

In another embodiment, in Formula (IV), at least one group $R^{14}$ is —$C(O)R^{15}$.

In another embodiment, in Formula (IV), at least one group $R^{14}$ is —$C(O)OR^{15}$.

In another embodiment, in Formula (IV), at least one group $R^{14}$ is —$C(O)N(R^{15})(R^{16})$.

In another embodiment, in Formula (IV), at least one group $R^{14}$ is —$SR^{15}$.

In another embodiment, in Formula (IV), at least one group $R^{14}$ is —$S(O)N(R^{15})(R^{16})$.

In another embodiment, in Formula (IV), at least one group $R^{14}$ is —$S(O)_2N(R^{15})(R^{16})$.

In another embodiment, in Formula (IV), at least one group $R^{14}$ is —$C(=NOR^{15})R^{16}$.

In another embodiment, in Formula (IV), at least one group $R^{14}$ is —$P(O)(OR^{15})(OR^{16})$.

In another embodiment, in Formula (IV), at least one group $R^{14}$ is —$N(R^{15})(R^{16})$.

In another embodiment, in Formula (IV), at least one group $R^{14}$ is —$N(R^{15})C(O)R^{16}$.

In another embodiment, in Formula (IV), at least one group $R^{14}$ is —$N(R^{15})S(O)R^{16}$.

In another embodiment, in Formula (IV), at least one group $R^{14}$ is —$N(R^{15})S(O)_2R^{16}$.

In another embodiment, in Formula (IV), at least one group $R^{14}$ is —$N(R^{15})S(O)_2N(R^{16})(R^{17})$.

In another embodiment, in Formula (IV), at least one group $R^{14}$ is —$N(R^{15})S(O)N(R^{16})(R^{17})$.

In another embodiment, in Formula (IV), at least one group $R^{14}$ is —$N(R^{15})C(O)N(R^{16})(R^{17})$.

In another embodiment, in Formula (IV), at least one group $R^{14}$ is —$N(R^{15})C(O)OR^{16}$.

In another embodiment, in Formula (IV), is a compound of the Formula (IV.a):

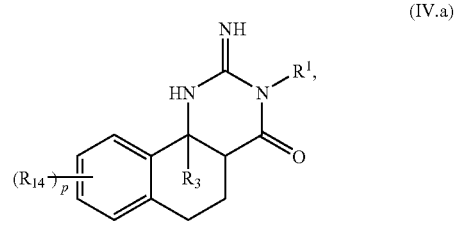

(IV.a)

wherein $R^1$, $R^3$, $R^{14}$, and p are selected independently and as defined in Formula (IV).

In another embodiment, the present invention provides a compound, or a stereoisomer, tautomer, or pharmaceutically acceptable salt or solvate thereof, having the general structure shown in Formula (V):

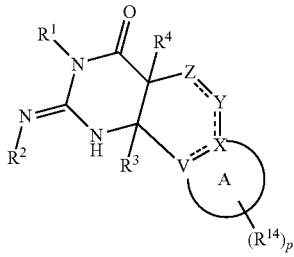

(V)

wherein $R^1$, $R^2$, $R^3$, $R^4$, Z, Y, X, V, ring A, p, and each $R^{14}$ is selected independently of each other and wherein:

ring A together with V and X forms a mono or multicyclic 4 to 12 membered cycloalkylene or cycloalkenylene ring, and $R^1$, $R^2$, $R^3$, $R^4$, Z, X, Y, V, $R^{14}$, and p are as defined in Formula I.

In another embodiment, in Formula (V), V is a carbon atom and V, X, and ring A, and —$(R^{14})_p$ form

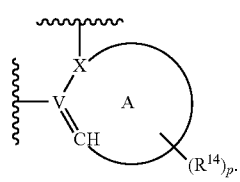

In another embodiment, in Formula (V), V is a carbon atom and V, X, and ring A, and —$(R^{14})_p$ form

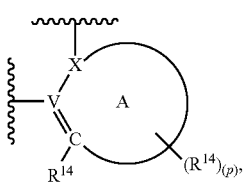

and p=0-4.

In another embodiment, in Formula (V), —V═X— is

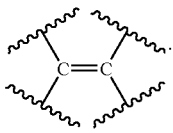

In another embodiment, in Formula (V), $R^1$ is alkyl.
In another embodiment, in Formula (V), $R^1$ is methyl.
In another embodiment, in Formula (V), $R^2$ is H.
In another embodiment, in Formula (V), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (V), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (V), $R^3$ is arylalkyl, heteroarylalkyl, arylcycloalkyl, heteroarylcycloalkyl, arylalkenyl, arylalkynyl, aryl or heteroaryl.

In another embodiment, in Formula (V), $R^3$ is heteroaryl or aryl.

In another embodiment, in Formula (V), $R^3$ is

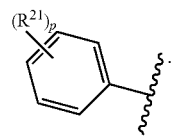

In another embodiment, in Formula (V), $R^3$ is

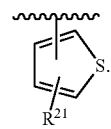

In another embodiment, in Formula (V), $R^3$ is

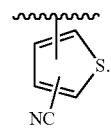

In another embodiment, in Formula (V), $R^3$ is

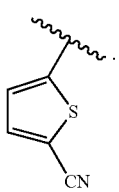

In another embodiment, in Formula (V), $R^4$ is H.
In another embodiment, in Formula (V), $R^4$ is alkyl.
In another embodiment, in Formula (V), $R^4$ is halo.
In another embodiment, in Formula (V), p is 0 (and $R^{14}$ is not present).
In another embodiment, in Formula (V), p is 1.
In another embodiment, in Formula (V), p is 2.
In another embodiment, in Formula (V), p is 3.
In another embodiment, in Formula (V), p is 4.
In another embodiment, in Formula (V), p is 5.

In another embodiment, in Formula (V), p is 2-5 and at least two groups $R^{14}$ are bound to the same ring atom.

In another embodiment, in Formula (V), at least one group $R^{14}$ is H.

In another embodiment, in Formula (V), at least one group $R^{14}$ is alkyl.

In another embodiment, in Formula (V), at least one group $R^{14}$ is arylalkyl.

In another embodiment, in Formula (V), at least one group $R^{14}$ is heteroarylalkyl.

In another embodiment, in Formula (V), at least one group $R^{14}$ is cycloalkylalkyl.

In another embodiment, in Formula (V), at least one group $R^{14}$ is heterocycloalkylalkyl.

In another embodiment, in Formula (V), at least one group $R^{14}$ is arylcycloalkylalkyl.

In another embodiment, in Formula (V), at least one group $R^{14}$ is heteroarylcycloalkylalkyl.

In another embodiment, in Formula (V), at least one group $R^{14}$ is arylheterocycloalkylalkyl.

In another embodiment, in Formula (V), at least one group $R^{14}$ is heteroarylheterocycloalkylalkyl.

In another embodiment, in Formula (V), at least one group $R^{14}$ is cycloalkyl.

In another embodiment, in Formula (V), at least one group $R^{14}$ is arylcycloalkyl.

In another embodiment, in Formula (V), at least one group $R^{14}$ is heteroarylcycloalkyl.

In another embodiment, in Formula (V), at least one group $R^{14}$ is heterocycloalkyl.

In another embodiment, in Formula (V), at least one group $R^{14}$ is arylheterocycloalkyl.

In another embodiment, in Formula (V), at least one group $R^{14}$ is heteroarylheterocycloalkyl.

In another embodiment, in Formula (V), at least one group $R^{14}$ is alkenyl.

In another embodiment, in Formula (V), at least one group $R^{14}$ is arylalkenyl.

In another embodiment, in Formula (V), at least one group $R^{14}$ is cycloalkenyl.

In another embodiment, in Formula (V), at least one group $R^{14}$ is arylcycloalkenyl.

In another embodiment, in Formula (V), at least one group $R^{14}$ is heteroarylcycloalkenyl.

In another embodiment, in Formula (V), at least one group $R^{14}$ is heterocycloalkenyl.

In another embodiment, in Formula (V), at least one group $R^{14}$ is arylheterocycloalkenyl.

In another embodiment, in Formula (V), at least one group $R^{14}$ is heteroarylheterocycloalkenyl.

In another embodiment, in Formula (V), at least one group $R^{14}$ is alkynyl.

In another embodiment, in Formula (V), at least one group $R^{14}$ is arylalkynyl.

In another embodiment, in Formula (V), at least one group $R^{14}$ is aryl.

In another embodiment, in Formula (V), at least one group $R^{14}$ is cycloalkylaryl.

In another embodiment, in Formula (V), at least one group $R^{14}$ is heterocycloalkylaryl.

In another embodiment, in Formula (V), at least one group $R^{14}$ is cycloalkenylaryl.

In another embodiment, in Formula (V), at least one group $R^{14}$ is heterocycloalkenylaryl.

In another embodiment, in Formula (V), at least one group $R^{14}$ is heteroaryl.

In another embodiment, in Formula (V), at least one group $R^{14}$ is cycloalkylheteroaryl.

In another embodiment, in Formula (V), at least one group $R^{14}$ is heterocycloalkylheteroaryl.

In another embodiment, in Formula (V), at least one group $R^{14}$ is cycloalkenylheteroaryl.

In another embodiment, in Formula (V), at least one group $R^{14}$ is heterocycloalkenylheteroaryl.

In another embodiment, in Formula (V), at least one group $R^{14}$ is halo.

In another embodiment, in Formula (V), at least one group $R^{14}$ is —$CH_2$—O—Si($R^9$)($R^{10}$)($R^{19}$).

In another embodiment, in Formula (V), at least one group $R^{14}$ is —N($R^{15}$)C(O)N($R^{16}$)($R^{17}$).

In another embodiment, in Formula (V), at least one group $R^{14}$ is —CN.

In another embodiment, in Formula (V), at least one group $R^{14}$ is —$OR^{15}$.

In another embodiment, in Formula (V), at least one group $R^{14}$ is —C(O)$R^{15}$.

In another embodiment, in Formula (V), at least one group $R^{14}$ is —C(O)$OR^{15}$. In another embodiment, in Formula (V), at least one group $R^{14}$ is —C(O)N($R^{15}$)($R^{16}$).

In another embodiment, in Formula (V), at least one group $R^{14}$ is —$SR^{15}$.

In another embodiment, in Formula (V), at least one group $R^{14}$ is —S(O)N($R^{15}$)($R^{16}$).

In another embodiment, in Formula (V), at least one group $R^{14}$ is —$S(O)_2$N($R^{15}$)($R^{16}$).

In another embodiment, in Formula (V), at least one group $R^{14}$ is —C(=N$OR^{15}$)$R^{16}$.

In another embodiment, in Formula (V), at least one group $R^{14}$ is —P(O)($OR^{15}$)($OR^{16}$).

In another embodiment, in Formula (V), at least one group $R^{14}$ is —N($R^{15}$)($R^{16}$).

In another embodiment, in Formula (V), at least one group $R^{14}$ is —N($R^{15}$)C(O)$R^{16}$.

In another embodiment, in Formula (V), at least one group $R^{14}$ is —N($R^{15}$)S(O)$R^{16}$.

In another embodiment, in Formula (V), at least one group $R^{14}$ is —N($R^{15}$)$S(O)_2R^{16}$.

In another embodiment, in Formula (V), at least one group $R^{14}$ is —N($R^{15}$)$S(O)_2$N($R^{16}$)($R^{17}$).

In another embodiment, in Formula (V), at least one group $R^{14}$ is —N($R^{15}$)S(O)N($R^{16}$)($R^{17}$).

In another embodiment, in Formula (V), at least one group $R^{14}$ is —N($R^{15}$)C(O)N($R^{16}$)($R^{17}$).

In another embodiment, in Formula (V), at least one group $R^{14}$ is —N($R^{15}$)C(O)$OR^{16}$.

In another embodiment, the present invention provides a compound, or a stereoisomer, tautomer, or pharmaceutically acceptable salt or solvate thereof, having the general structure shown in Formula (VI):

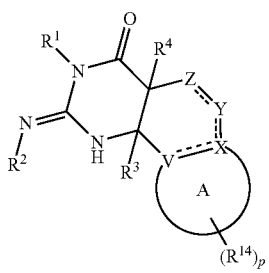

(VI)

wherein $R^1$, $R^2$, $R^3$, $R^4$, Z, Y, X, V, ring A, p, and each $R^{14}$ is selected independently of each other and wherein:

ring A forms a mono or multicyclic 4 to 12 membered heterocycloalkylene or heterocycloalkenylene ring, wherein the heteroatom or heteroatoms of said heterocycloalkeylene or heterocycloalkenylene are independently selected from the group consisting of —O—, —S—, —S(O)—, —S(O)$_2$—, and —N(R$^5$)—; and $R^1$, $R^2$, $R^3$, $R^4$, Z, X, Y, V, $R^{14}$, and p are as defined in Formula I.

In another embodiment, in Formula (VI), V is a carbon atom and V, X, and ring A, and —(R$^{14}$)$_p$ form

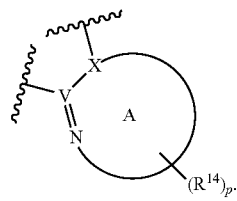

In another embodiment, in Formula (VI), V is a carbon atom and V, X, and ring A, and —(R$^{14}$)$_p$ form

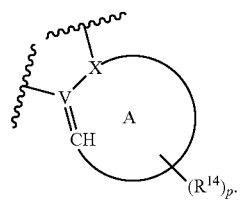

In another embodiment, in Formula (VI), V is a carbon atom and V, X, and ring A, and —(R$^{14}$)$_p$ form

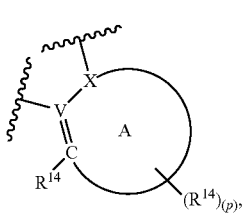

and p=0-4.

In another embodiment, in Formula (VI), —V=X— is

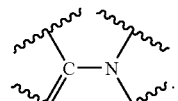

In another embodiment, in Formula (VI), —V=X— is

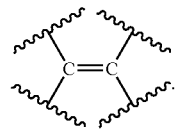

In another embodiment, in Formula (VI), $R^1$ is alkyl.

In another embodiment, in Formula (VI), $R^1$ is methyl.

In another embodiment, in Formula (VI), $R^2$ is H.

In another embodiment, in Formula (VI), $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (VI), $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

In another embodiment, in Formula (VI), $R^3$ is arylalkyl, heteroarylalkyl, arylcycloalkyl, heteroarylcycloalkyl, arylalkenyl, arylalkynyl, aryl or heteroaryl.

In another embodiment, in Formula (VI), $R^3$ is heteroaryl or aryl.

In another embodiment, in Formula (VI), $R^3$ is

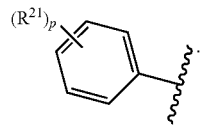

In another embodiment, in Formula (VI), $R^3$ is

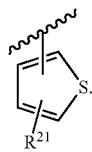

In another embodiment, in Formula (VI), $R^3$ is

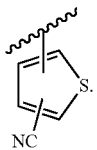

In another embodiment, in Formula (VI), $R^3$ is

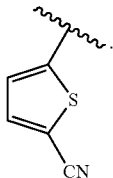

In another embodiment, in Formula (VI), $R^4$ is H.
In another embodiment, in Formula (VI), $R^4$ is alkyl.
In another embodiment, in Formula (VI), $R^4$ is halo.
In another embodiment, in Formula (VI), p is 0 (and $R^{14}$ is not present).
In another embodiment, in Formula (VI), p is 1.
In another embodiment, in Formula (VI), p is 2.
In another embodiment, in Formula (VI), p is 3.
In another embodiment, in Formula (VI), p is 4.
In another embodiment, in Formula (VI), p is 5.
In another embodiment, in Formula (VI), p is 2-5 and at least two groups $R^{14}$ are bound to the same ring atom.
In another embodiment, in Formula (VI), at least one group $R^{14}$ is H.
In another embodiment, in Formula (VI), at least one group $R^{14}$ is alkyl.
In another embodiment, in Formula (VI), at least one group $R^{14}$ is arylalkyl.
In another embodiment, in Formula (VI), at least one group $R^{14}$ is heteroarylalkyl.
In another embodiment, in Formula (VI), at least one group $R^{14}$ is cycloalkylalkyl.
In another embodiment, in Formula (VI), at least one group $R^{14}$ is heterocycloalkylalkyl.
In another embodiment, in Formula (VI), at least one group $R^{14}$ is arylcycloalkylalkyl.
In another embodiment, in Formula (VI), at least one group $R^{14}$ is heteroarylcycloalkylalkyl.
In another embodiment, in Formula (VI), at least one group $R^{14}$ arylheterocycloalkylalkyl.
In another embodiment, in Formula (VI), at least one group $R^{14}$ is heteroarylheterocycloalkylalkyl.
In another embodiment, in Formula (VI), at least one group $R^{14}$ is cycloalkyl.
In another embodiment, in Formula (VI), at least one group $R^{14}$ is arylcycloalkyl.
In another embodiment, in Formula (VI), at least one group $R^{14}$ is heteroarylcycloalkyl.
In another embodiment, in Formula (VI), at least one group $R^{14}$ is heterocycloalkyl.
In another embodiment, in Formula (VI), at least one group $R^{14}$ is arylheterocycloalkyl.
In another embodiment, in Formula (VI), at least one group $R^{14}$ is heteroarylheterocycloalkyl.
In another embodiment, in Formula (VI), at least one group $R^{14}$ is alkenyl.
In another embodiment, in Formula (VI), at least one group $R^{14}$ is arylalkenyl.
In another embodiment, in Formula (VI), at least one group $R^{14}$ is cycloalkenyl.
In another embodiment, in Formula (VI), at least one group $R^{14}$ is arylcycloalkenyl.
In another embodiment, in Formula (VI), at least one group $R^{14}$ is heteroarylcycloalkenyl.
In another embodiment, in Formula (VI), at least one group $R^{14}$ is heterocycloalkenyl.
In another embodiment, in Formula (VI), at least one group $R^{14}$ is arylheterocycloalkenyl.
In another embodiment, in Formula (VI), at least one group $R^{14}$ is heteroarylheterocycloalkenyl.
In another embodiment, in Formula (VI), at least one group $R^{14}$ is alkynyl.
In another embodiment, in Formula (VI), at least one group $R^{14}$ is arylalkynyl.
In another embodiment, in Formula (VI), at least one group $R^{14}$ is aryl.
In another embodiment, in Formula (VI), at least one group $R^{14}$ is cycloalkylaryl.
In another embodiment, in Formula (VI), at least one group $R^{14}$ is heterocycloalkylaryl.
In another embodiment, in Formula (VI), at least one group $R^{14}$ is cycloalkenylaryl.
In another embodiment, in Formula (VI), at least one group $R^{14}$ is heterocycloalkenylaryl.
In another embodiment, in Formula (VI), at least one group $R^{14}$ is heteroaryl.
In another embodiment, in Formula (VI), at least one group $R^{14}$ is cycloalkylheteroaryl.
In another embodiment, in Formula (VI), at least one group $R^{14}$ is heterocycloalkylheteroaryl.
In another embodiment, in Formula (VI), at least one group $R^{14}$ is cycloalkenylheteroaryl.
In another embodiment, in Formula (VI), at least one group $R^{14}$ is heterocycloalkenylheteroaryl.
In another embodiment, in Formula (VI), at least one group $R^{14}$ is halo.
In another embodiment, in Formula (VI), at least one group $R^{14}$ is $—CH_2—O—Si(R^9)(R^{10})(R^{19})$.
In another embodiment, in Formula (VI), at least one group $R^{14}$ is $—N(R^{15})C(O)N(R^{16})(R^{17})$.
In another embodiment, in Formula (VI), at least one group $R^{14}$ is $—CN$.
In another embodiment, in Formula (VI), at least one group $R^{14}$ is $—OR^{15}$.
In another embodiment, in Formula (VI), at least one group $R^{14}$ is $—C(O)R^{15}$.
In another embodiment, in Formula (VI), at least one group $R^{14}$ is $—C(O)OR^{15}$.
In another embodiment, in Formula (VI), at least one group $R^{14}$ is $—C(O)N(R^{15})(R^{16})$.
In another embodiment, in Formula (VI), at least one group $R^{14}$ is $—SR^{15}$.

In another embodiment, in Formula (VI), at least one group $R^{14}$ is —S(O)N($R^{15}$)($R^{16}$).

In another embodiment, in Formula (VI), at least one group $R^{14}$ is —S(O)$_2$N($R^{15}$)($R^{16}$).

In another embodiment, in Formula (VI), at least one group $R^{14}$ is —C(=NOR$^{15}$)$R^{16}$.

In another embodiment, in Formula (VI), at least one group $R^{14}$ is —P(O)(OR$^{15}$)(OR$^{16}$).

In another embodiment, in Formula (VI), at least one group $R^{14}$ is —N($R^{15}$)($R^{16}$).

In another embodiment, in Formula (VI), at least one group $R^{14}$ is —N($R^{15}$)C(O)$R^{16}$.

In another embodiment, in Formula (VI), at least one group $R^{14}$ is —N($R^{15}$)S(O)$R^{16}$.

In another embodiment, in Formula (VI), at least one group $R^{14}$ is —N($R^{15}$)S(O)$_2$$R^{16}$.

In another embodiment, in Formula (VI), at least one group $R^{14}$ is —N($R^{15}$)S(O)$_2$N($R^{16}$)($R^{17}$).

In another embodiment, in Formula (VI), at least one group $R^{14}$ is —N($R^{15}$)S(O)N($R^{16}$)($R^{17}$).

In another embodiment, in Formula (VI), at least one group $R^{14}$ is —N($R^{15}$)C(O)N($R^{16}$)($R^{17}$).

In another embodiment, in Formula (VI), at least one group $R^{14}$ is —N($R^{15}$)C(O)OR$^{16}$.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

A group described as "1 to n groups" (e.g., "$R^{23}$ is 1 to 5 groups") means that such group (e.g., such $R^{23}$ group) is present from 1 to 5 times on the moiety to which it is described as attached. When two or more such groups are present each such group is understood to be selected independently of the other(s).

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" means an aromatic monocyclic or multicyclic ring system comprising about 6 to about 14 carbon atoms, preferably about 6 to about 10 carbon atoms. The aryl group can be optionally substituted with one or more substituents (e.g., $R^{18}$, $R^{21}$, $R^{22}$, etc.) which may be the same or different, and are as defined herein or two substituents on adjacent carbons can be linked together to form

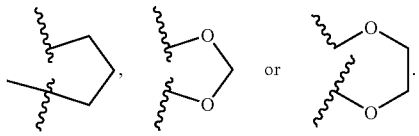

Non-limiting examples of suitable aryl groups include phenyl and naphthyl. Furthermore, this term encompasses multicyclic aryl rings wherein at least one of the multicyclic aryl rings can be unsaturated or partially saturated as in the following non-limiting examples:

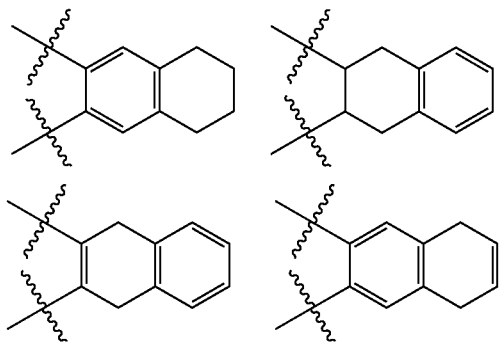

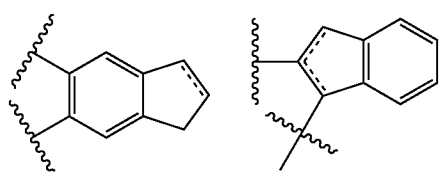 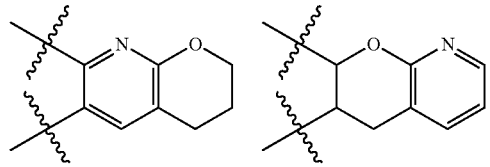

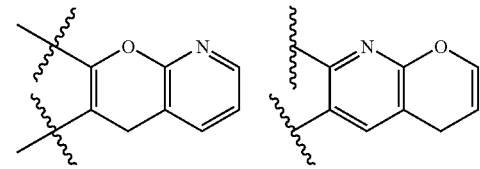

"Heteroaryl" means an aromatic monocyclic or multicyclic ring system comprising about 5 to about 14 ring atoms, preferably about 5 to about 10 ring atoms, in which one to four of the ring atoms is an element other than carbon, for example nitrogen, oxygen or sulfur, alone or in combination. Preferred heteroaryls contain about 5 to about 6 ring atoms. The "heteroaryl" can be optionally substituted by one or more $R^{21}$ substituents which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. Furthermore, this term encompasses multicyclic heteroaryl rings wherein at least one of the multicyclic heteroaryl rings can be unsaturated or partially saturated as in the following non-limiting examples:

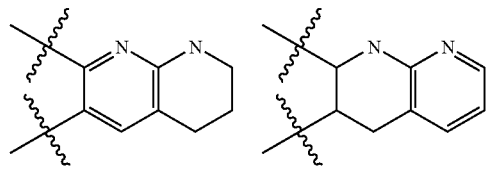

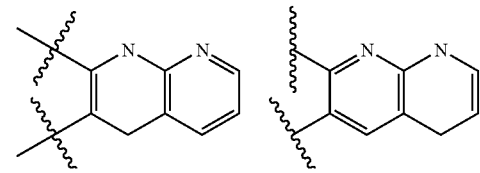

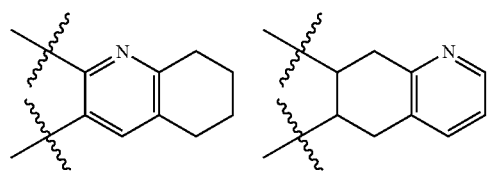

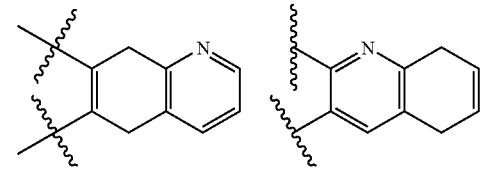

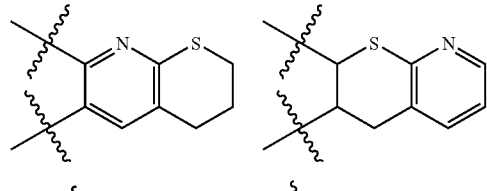

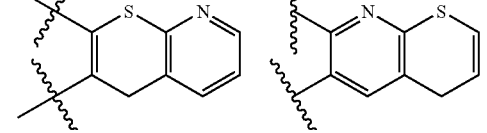

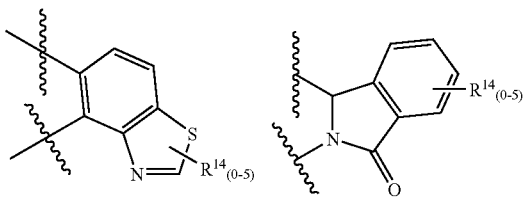

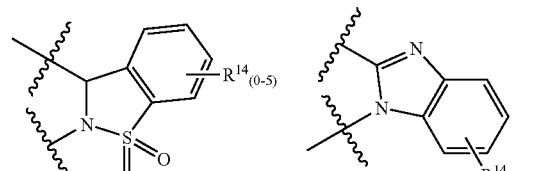

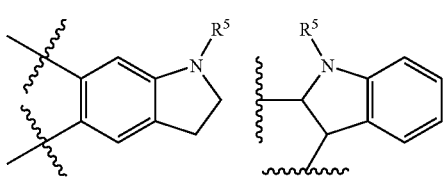

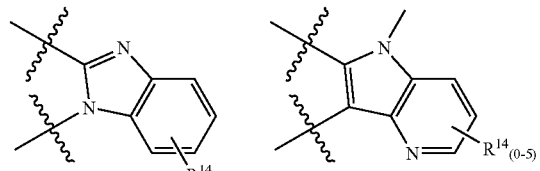

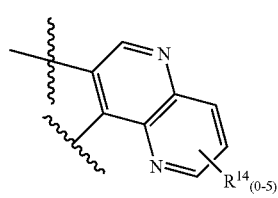

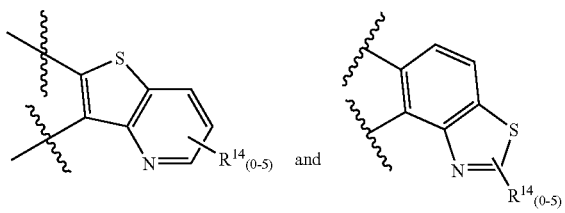 and

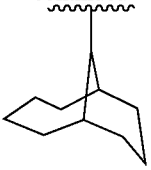

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 15 carbon atoms, preferably about 5 to about 10 carbon atoms. Preferred cycloalkyl rings contain about 5 to about 7 ring atoms. The cycloalkyl can be optionally substituted with one or more $R^{21}$ substituents which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. Further non-limiting examples of cycloalkyl include the following

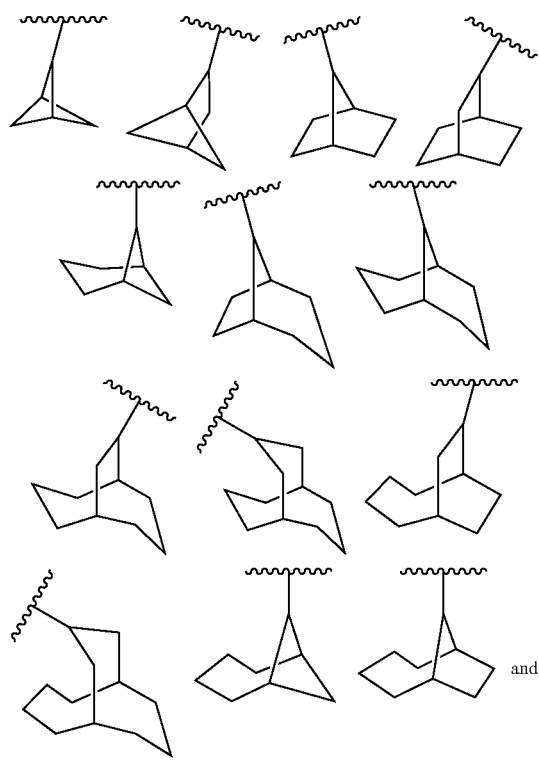

and

"Cycloalkylether" means a non-aromatic ring of 3 to 15 atoms comprising an oxygen atom and 2 to 14 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 15 carbon atoms, preferably about 5 to about 10 carbon atoms which contains at least one carbon-carbon double bond. The cycloalkenyl ring can be optionally substituted with one or more $R^{21}$ substituents which may be the same or different, and are as defined above. Preferred cycloalkenyl rings contain about 5 to about 7 ring atoms. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

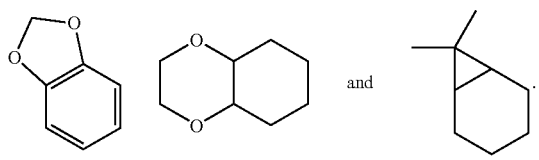

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which 1-3, preferably 1 or 2 of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more ring system substituents, e.g., $R^{21}$ substituents, which may be the same or different, as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. "Heterocyclyl" also includes rings wherein ═O replaces two available hydrogens on the same carbon atom (i.e., heterocyclyl includes rings having a carbonyl group in the ring). Example of such moiety is pyrrolidone

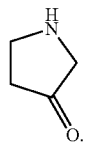

Other non-limiting examples include:

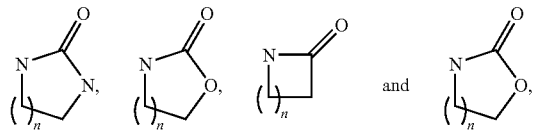

wherein n and q are each independently 0, 1, 2, 3, 4, 5, etc.

"Heterocyclylalkyl" (or "heterocycloalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" (or "heterocycloalkenyl") means a non-aromatic monocyclic or multicyclic ring system comprising about 3 to about 10 ring atoms, preferably about to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like. "Heterocyclenyl" also includes rings wherein ═O replaces two available hydrogens on the same carbon atom (i.e., heterocyclyl includes rings having a carbonyl group in the ring). Examples of such moiety include pyrrolidinone:

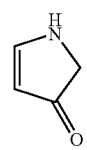

and the like.

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

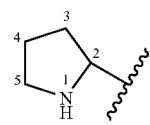

there is no —OH attached directly to carbons marked 2 and 5.

It should also be noted that tautomeric forms such as, for example, the moieties:

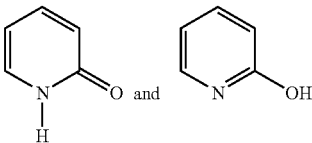

are considered equivalent in certain embodiments of this invention.

"Halo" or "halogen" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

"Heteroaralkyl" (or "heteroarylalkyl") means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Arylalkyl" or "aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Arylcycloalkyl" means a group derived from a fused aryl and cycloalkyl as defined herein. Preferred arylcycloalkyls are those wherein aryl is phenyl and cycloalkyl consists of about 5 to about 6 ring atoms. The arylcycloalkyl can be optionally substituted by 1-5 $R^{21}$ substituents. Non-limiting examples of suitable arylcycloalkyls include indanyl and 1,2,3,4-tetrahydronaphthyl and the like. The bond to the parent moiety is through a non-aromatic carbon atom.

"Arylheterocycloalkyl" means a group derived from a fused aryl and heterocycloalkyl as defined herein. Preferred arylcycloalkyls are those wherein aryl is phenyl and heterocycloalkyl consists of about 5 to about 6 ring atoms. The arylheterocycloalkyl can be optionally substituted by 1-5 $R^{21}$ substituents. Non-limiting examples of suitable arylheterocycloalkyls include

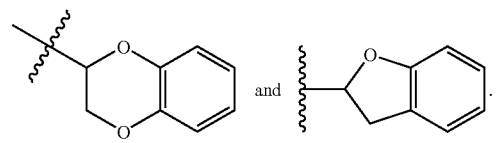

The bond to the parent moiety is through a non-aromatic carbon atom.

Similarly, "heteroarylalkyl" "cycloalkylalkyl" and "heterocycloalkylalkyl" mean a heteroaryl-, cycloalkyl- or heterocycloalkyl-alkyl-group in which the heteroaryl, cycloalkyl, heterocycloalkyl and alkyl are as previously described. It is also understood that the terms "arylcycloalkylalkyl", "heteroarylcycloalkylalkyl", "arylheterocycloalkylalkyl", "heteroarylheterocycloalkylalkyl", "heteroarylcycloalkyl", "heteroarylheterocycloalkyl", "arylcycloalkenyl", "heteroarylcycloalkenyl", "heterocycloalkenyl", "arylheterocycloalkenyl", "heteroarylheterocycloalkenyl", "cycloalkylaryl", "heterocycloalkylaryl", "heterocycloalkenylaryl", "cycloalkylheteroaryl", "heterocycloalkylheteroaryl", "cycloalkenylaryl" "cycloalkenylheteroaryl", "heterocycloalkenylaryl" and "heterocycloalkenylheteroaryl"

similarly represented by the combination of the groups aryl-, cycloalkyl-, alkyl-, heteroaryl-, heterocycloalkyl-, cycloalkenyl- and heterocycloalkenyl- as previously described. Preferred groups contain a lower alkyl group. The bond to the parent moiety is through the alkyl.

"Alkoxyalkyl" means a group derived from an alkoxy and alkyl as defined herein. The bond to the parent moiety is through the alkyl.

"Arylalkenyl" means a group derived from aryl and alkenyl as defined herein. Preferred arylalkenyls are those wherein aryl is phenyl and the alkenyl consists of about 3 to about 6 atoms. The arylalkenyl can be optionally substituted by one or more $R^{27}$ substituents. The bond to the parent moiety is through a non-aromatic carbon atom.

"Arylalkynyl" means a group derived from aryl and alkynyl as defined herein. Preferred arylalkynyls are those wherein aryl is phenyl and the alkynyl consists of about 3 to about 6 atoms. The arylalkynyl can be optionally substituted by one or more $R^{27}$ substituents. The bond to the parent moiety is through a non-aromatic carbon atom.

The suffix "ene" on alkyl, aryl, heterocycloalkyl, etc. indicates a divalent moiety, e.g., —CH$_2$CH$_2$— is ethylene, and

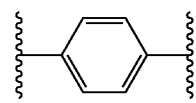

is para-phenylene.

It is understood that multicyclic divalent groups, for example, arylheterocycloalkylene, can be attached to other groups via bonds that are formed on either ring of said group. For example,

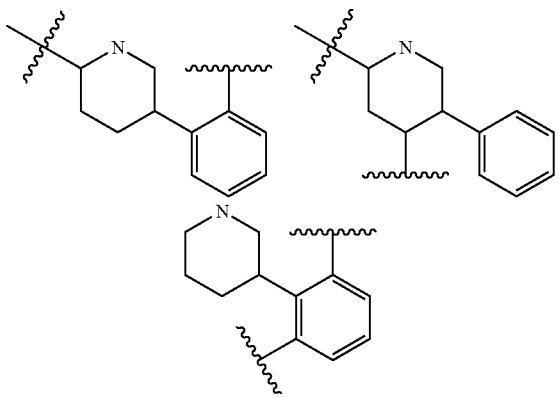

The term "optionally substituted" means optional substitution with the specified groups, radicals or moieties, in available position or positions.

Substitution on a cycloalkylalkyl, heterocycloalkylalkyl, arylalkyl, or heteroarylalkyl moiety includes substitution on the ring portion and/or on the alkyl portion of the group.

When a variable appears more than once in a group, e.g., $R^9$ in —N=C(R$^9$)$_2$, or a variable appears more than once in the structure of formula I, e.g., $R^{15}$ may appear in both $R^1$ and $R^3$, the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," one to three compounds of formula I can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line ~~~ as a bond generally indicates a mixture of, or either of, the possible isomers, e.g., containing (R)- and (S)-stereochemistry. For example,

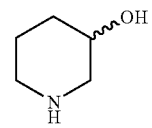

means containing both

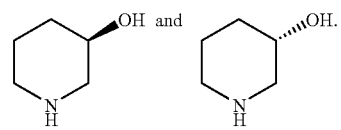

Lines drawn into the ring systems, such as, for example:

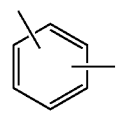

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

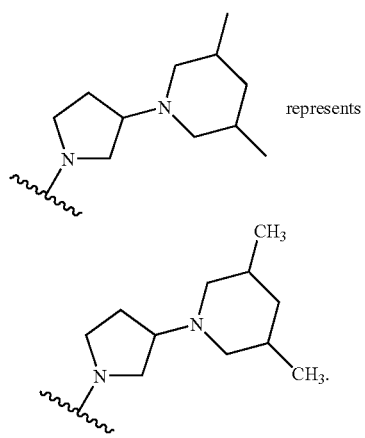

represents

It should also be noted that any heteroatom with unsatisfied valences in the text, schemes, examples, structural formulae, and any Tables herein is assumed to have the hydrogen atom or atoms to satisfy the valences.

It is understood that there are no cumulative double bonds between V, X, Y, Z and the ring atoms of ring A adjacent to V and X, that is, each atom of V, X, Y, Z and the ring atoms of ring A adjacent to V and X do not form more than one double bond. Non-limiting examples of cumulative double bonds include "C=C=C", "N=C=C", "N=C=N", etc.

Those skilled in the art will recognize that certain compounds of formula I are tautomeric, and all such tautomeric forms are contemplated herein as part of the present invention. For example, a compound wherein $R^1$ is H, said compound can be represented by any of the following structures:

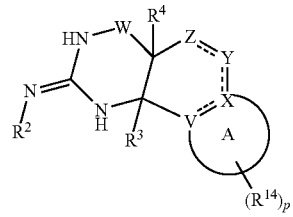

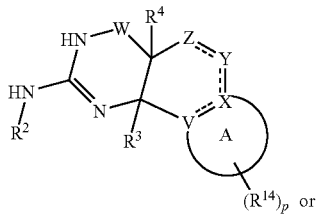

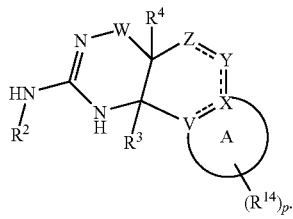

It is understood that what is meant by when two groups, (for example, $R^6$ and $R^{6a}$ or two $R^{14}$) form a carbonyl with the carbon to which they attached are the

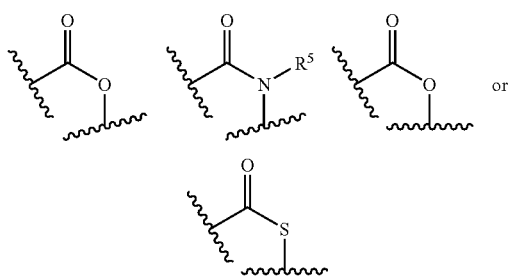

following groups:

When, $R^{14}$, for example is, —N($R^{15}$)S(O)$_2$N($R^{16}$)($R^{17}$), $R^{16}$ and $R^{17}$ may be combined to form a ring, which is, for example

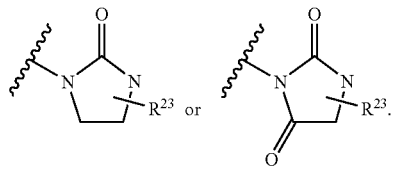

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$)

alkyl and $Y^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —C(Y$^4$)Y$^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting aspartyl protease and/or inhibiting BACE-1 and thus producing the desired therapeutic effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, bisulfates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) or (II) may be atropisomers (e.g., substituted biaryls) and are considered as part of this invention. Enantiomers can also be separated by use of chiral HPLC column.

Polymorphic forms of the compounds of formula I, and of the salts, solvates and prodrugs of the compounds of formula I are intended to be included in the present invention.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) or (II) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of formula (I) or (II) can generally be prepared by following procedures analogous to those disclosed in the Schemes and/or in the Examples hereinbelow, by substituting an appropriate isotopically labelled reagent for a non-isotopically labelled reagent.

It should be noted that throughout the specification and Claims appended hereto any formula, compound, moiety or chemical illustration with unsatisfied valences is assumed to have the hydrogen atom to satisfy the valences unless the context indicates a bond.

Compounds of formula I can be made using procedures known in the art. The following reaction schemes show typical procedures, but those skilled in the art will recognize that other procedures can also be suitable.

In the Schemes and in the Example below, the following abbreviations are used:
room temperature: r.t.
high pressure liquid chromatography: HPLC
reverse-phase HPLC: RP-HPLC
liquid chromatography mass spectrometry: LCMS
mass spectrometry: MS
polytetrafluoroethylene: PTFE
hour: h
minute: min
retention time: tR
ethyl: Et
methyl: Me
benzyl: Bn
lithium diisopropylamide: LDA
1-(3-dimethylaminopropyl)-3-ethyl carbodiimide hydrochloride: EDCI DIEA means N,N-diisopropylethylamine
ethyl acetate: EtOAc
N,N-dimethylformamide: DMF
methanol: MeOH
Ethanol: EtOH
acetonitrile: $CH_3CN$
acetic acid: AcOH
magnesium sulfate: $MgSO_4$
copper iodide: CuI
diisopropylamine: $iPr_2NH$
Dichlorobis(triphenylphosphine)palladium: $PdCl_2(PPh_3)_2$
ammonium hydroxide: $NH_4OH$
trifluoroacetic acid: TFA
benzyloxycarbonyl: Cbz
tert-butoxycarbonyl: Boc
DCM: Dichloromethane
TMSCHN$_2$: Trimethylsilyldiazomethane Teoc-OSu: O-Trimethylsilylethoxycarbonyl N-hydroxylsuccinate
TBAF: Tetrabutylammonium Flouride
THF: Tetrahydrofurane
MCPBA: meta-Chloroperbenzoic acid
TsOH: Toluenesulfonic acid.
PhIO: iodosobenzene
$Pb(OAc)_4$: Lead tetra-acetate If one were to follow the procedures in the examples below, then one would obtain the products indicated therein.

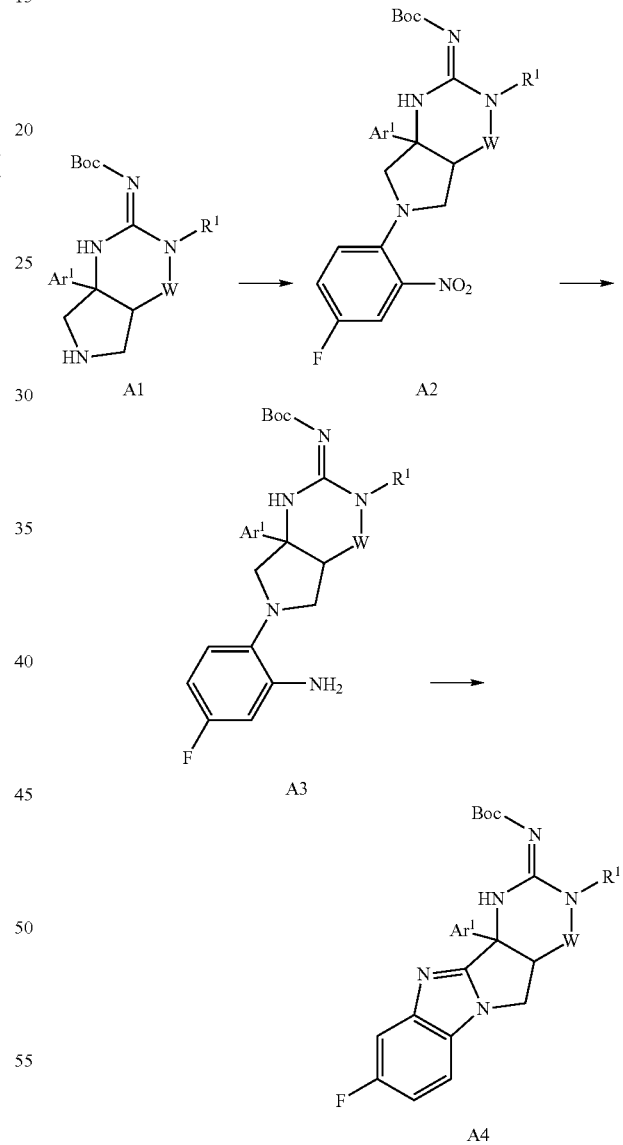

Method A

Method A, Step 1:

A literature procedure is adapted (J. S. Yadav, B. V. S. Reddy, A. K. Basak and A. Venkat Narsaiah Tetrahedron Lett.; 44 (10), 2217-2220).

To a solution of A1 (R1=Me, Ar1=5-Cyanothienyl and W=—(CO)—, 1 mmol) in 2 mL of 1-butyl-3-methylimidazolium hexafluorophosphate ([bmim]PF$_6$) is added 2,5-di- Fluoronitrobenzene and the solution is stirred overnight before the reaction mixture is washed with diethyl ether (3×10 mL). The ether layers are combined and concentrated to give a product mixture which is purified via a gel column and eluted with a mixture of ethyl acetate:hexane to give A2 (R1=Me, Ar1=5-Cyanothienyl and W=—(CO)—).

Method A, Step 2:

A literature procedure is adapted (Toshiki Murata et. al; Bioorganic & Med. Chem. Lett; 13 (5), 913-918).

A mixture of A2 (R1=Me, Ar1=5-Cyanothienyl and W=—(CO)—; 1 mmol), 100 mg of fine powdered Fe, $NH_4Cl$ in Ethanol/water is refluxed until the starting material disappears. The final mixture is filtered, and solution concentrated and residue chromatographed to give product A3 (R1=Me, Ar1=5-Cyanothienyl and W=—(CO)—).

Method A, Step 3:

A literature procedure is adapted (Islam, I. and Skibo, E. J. Org. Chem. 1990, 55, 3195-3205).

A mixture of 3 mmol of A3 (R1=Me, Ar1=5-Cyanothienyl and W=—(CO)—) in 6 mL of 96% formic acid and 3 ml of 30% hydrogen peroxide is stirred at 70 C for 30 min. The reaction mixture is concentrated and the residue purified via a C-18 RP-HPLC to give product A4 ((R1=Me, Ar1=5-Cyanothienyl and W=—(CO)—).

Alternatively, A3 can be converted to A4 using a published procedure (Mohrle, H. and Gerloff, J. Archiv Der Pharmazie, 311, 1978(5), 381-393).

is consumed. The residue is chromatographed via a silica gel column to give B2 (R14=H, R3=Ph).

Method B, Step 2:

A literature procedure is adapted (K. C. Nicolaou, Scott A. Snyder, Deborah A. Longbottom, Annie Z. Nalbandian, Xianhai Huang Chemistry—A European Journal 2004, (22), 10, 5581-5606).

B2 (R14=H, R3=Ph) (0.5 mmol, 1 eq) and B8(2.5 eq) in THF (5 mL) is refluxed for 2 h before it is poured into sat. NH4Cl and extracted with DCM. The organic solution is dried and concentrated and the residue chromatographed to give B3 (R14=H, R3=Ph).

Method B, Step 3:

A literature procedure is adapted (Avenoza, Alberto; Busto, Jesus H.; Corzana, Francisco; Jimenez-Oses, Gonzalo; Peregrina, Jesus M. *Chemical Communications* (2004), (8), 980-981)

To a DMF solution of B3 (R14=H, R3=Ph; 1 mmol) is added NaCN (10 eq) and the solution is stirred overnight before it is partitioned between DCM and water. The organic layer is dried and concentrated and the residue chromatographed to give B4 (R14=H, R3=Ph).

Method B, Step 4:

A mixture of B4 (R14=H, R3=Ph) in conc. HBr is refluxed and after the reaction is done, the solution is concentrated and residue chromatographed using a C18 RP system to give the b-aminoacid. To a methanolic solution of the aminoacid is

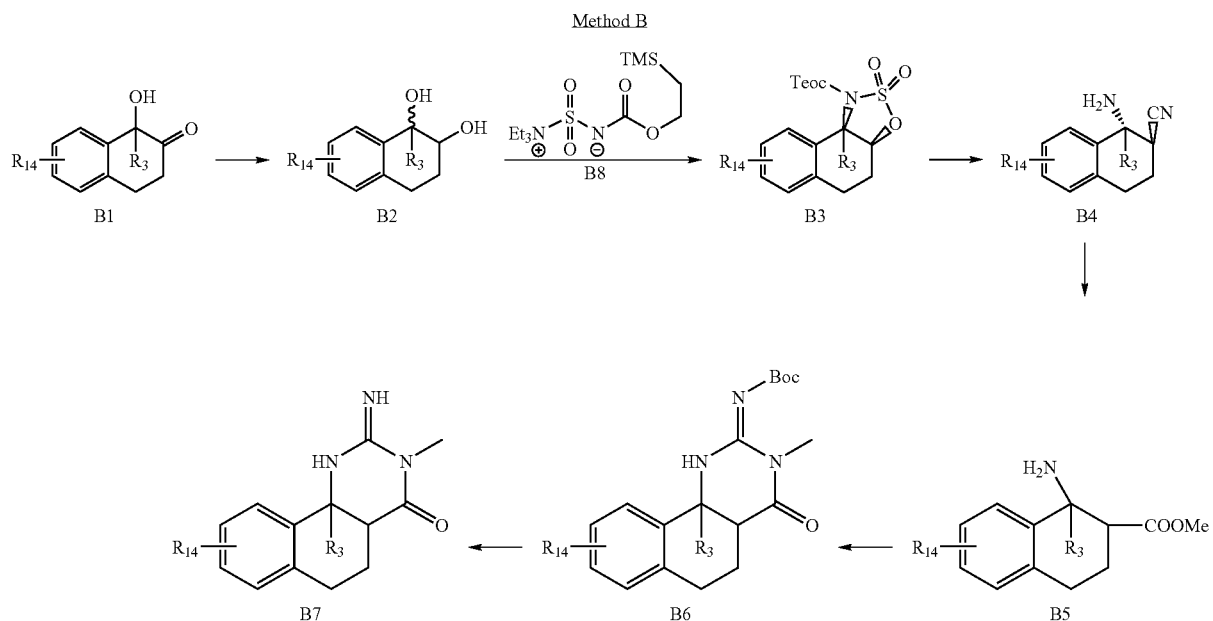

Method B, Step 1:

B1 (R14=H, R3=Ph) is a known compound in the literature: (Enders, Dieter; Niemeier, Oliver Synlett (2004), (12), 2111-2114).

To a Methanolic solution of B1 (R14=H, R3=Ph) is added NaBH4 (0.5 eq) and the solution is concentrated after the SM added TMSCHN2 untill the starting material disappears before the solvent is removed and residue chromatographed to give compound B5 (R14=H, R3=Ph).

Method B, Step 5:

To a DMF solution of B5 is added DIEA (1 eq), N-Methyl-N'-Boc-thiourea (1.2 eq) followed by EDCI (1.2 eq) and the solution is stirred at rt overnight before the reaction partitioned between DCM/water. The organic layer is dried and concentrated and residue chromatographed to give B6 (R14=H, R3=Ph).

Method B Step 6:

Compound B6 (R14=H, R³=Ph) is treated with 50% TFA in DCM at rt. After removal of volatiles, the residue is chromatographed to give B7(R14=H, R3=Ph).

R¹=Methyl and W is —C(O)—) in 80% yield. ¹H NMR (CDCl₃) δ10.34 (br, 1H), 7.07-6.93 (m, 3H), 6.33 (br, 1H), 3.87-3.79 (m, 2H), 3.62-3.59 (m, 1H), 3.33 (s, 3H), 1.51 (s, 9H).

Method C, Step 4:

A literature procedure will be followed for next three transformation *Tetrahedron*, 2006, 62, 8748-8754:

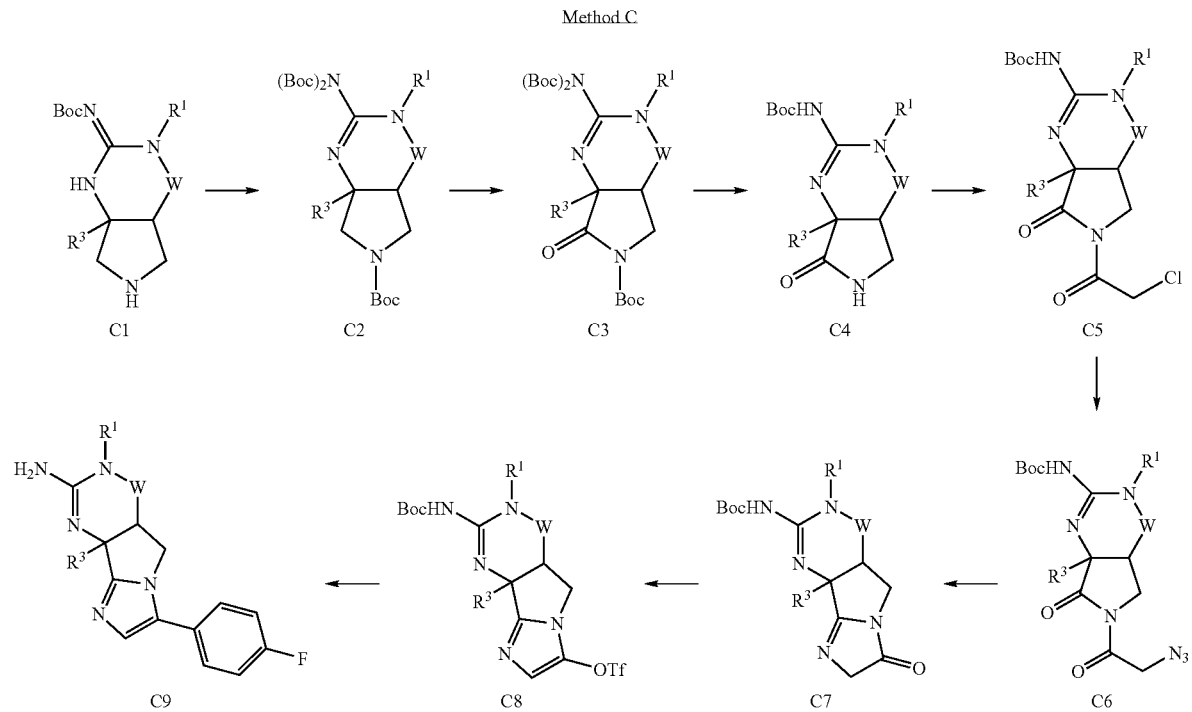

Method C

Method C, Step 1:

To a solution of C1 (R³=2,5-difluorophenyl, R¹=Methyl and W is —C(O)—; 1 g, 2.6 mmol) in 8 mL CH₂Cl₂ containing (Boc)₂O (2.2 equiv. 6.5 mmol, 1.44 gm) and DMAP (0.2 equiv., 0.52 mmol, 63 mg) was added Et₃N (2.5 equiv. 6.5 mmol, 1 mL) at rt. The resulting solution was stirred for 2 hr or until the reaction completed. The reaction mixture was chromatographed to yield C2 (R³=2,5-difluorophenyl, R¹=Methyl and W is —C(O)—) in quantitative yield.

Method C, Step 2:

To a solution of C2 (R³=2,5-difluorophenyl, R¹=Methyl and W is —C(O)—; 2.6 mmol) in a mixture of CCl₄, MeCN and H₂O (2/2/3 v/v/v) were added 1.2 gm of NaIO₄ and 172 mg of RuO₂. The resulting reaction mixture was stirred for 12 hr at rt. with addition of additional oxidant until the reaction was completed. After filtration, the organic reaction mixture was concentrated and residue purified to obtain 3 (R³=2,5-difluorophenyl, R¹=Methyl and W is —C(O)—) in 50% yield. ¹H NMR (CDCl₃) δ 7.32 (m, 1H), 7.02 (m, 2H), 4.22 (dd, 1H, J=10 Hz, J=9 Hz), 3.74 (t, J=Hz. 1H), 3.66 (t, J=9 Hz, 1H), 3.16 (s, 3H), 1.51-1.49 (m, 18H).

Method C, Step 3:

To a solution of C3 (R³=2,5-difluorophenyl, R¹=Methyl and W is —C(O)—) in 1.5 mL MeCN was added 20 mg of Mg(ClO₄)₂ and stirred for 2 hr. The reaction mixture was diluted with water and extracted with ethyl acetate. The organic phase was concentrated and residue purified with ethyl in hexanes to yield C4 (R³=2,5-difluorophenyl, To a solution of C4 (R³=2,5-difluorophenyl, R¹=Methyl and W is —C(O)—; 1 mmol) in 3 mL THF will be added n-BuLi (2.2 equiv.) at –78° C. over the period of 3 minutes. The resulting mixture will be stirred for 10 minutes at –78° C. before chloroacetyl chloride is added. The resulting mixture will be stirred at –78° C. for 1 hr before it is mixed with water and extracted with ethyl acetate. The crude product C5 (R³=2, 5-difluorophenyl, R¹=Methyl and W is —C(O)—) will be used for next step without purification.

Method C, Step 5:

To the vigorously stirred solution of C5 (R³=2,5-difluorophenyl, R¹=Methyl and W is —C(O)—)(1 mmol) in 5 mL DMSO will be added 4 equiv. of NaN₃ and resulting solution will be stirred at room temperature until the reaction is complete before it is diluted with water and extracted with ethyl acetate. After removal of solvent, the organic residue will be purified to give C6 (R³=2,5-difluorophenyl, R¹=Methyl and W is —C(O)—).

Method C, Step 6:

To a solution of C6 (R³=2,5-difluorophenyl, R¹=Methyl and W is —C(O)—; 1 mmol) in 5 mL benzene will be added triphenylphosphine (1 mmol). The reaction mixture will be stirred at room temperature until the reaction is complete to give C7 (R³=2,5-difluorophenyl, R¹=Methyl and W is —C(O)—) after purification.

Method C, Step 7:

A literature procedure will be adapted: *Organic Letters* 2006, 8, 781-784.

To a solution of KHMDS in 5 mL THF (2.2 mmol) will be added a solution of C7 ($R^3$=2,5-difluorophenyl, $R^1$=Methyl and W is —C(O)—, 1 mmol) in 2 mL THF at −78° C. The resulting mixture will be stirred at −78° C. for 2 hr before a solution of PhNTf$_2$ (1.4 mmol) in 3 mL THF is added. The reaction mixture will be slowly warmed to room temperature and stirred for 16 hr before the reaction mixture is worked up to give compound C8 ($R^3$=2,5-difluorophenyl, $R^1$=Methyl and W is —C(O)—) after purification.

Method C, Step 8:

A literature procedure will be adapted for next transformation *Synthesis*, 2006, (2), 299-304.

To a solution of C8 ($R^3$=2,5-difluorophenyl, $R^1$=Methyl and W is —C(O)—; 1 mmol) in 10 mL toluene will be added Pd(PPh$_3$)$_4$ (5 mol %) and the resulting solution will be stirred at room temperature for 30 minutes before a solution of $R^{14}$—B(OH)$_2$ ($R^{14}$=p-fluorophenyl) (1 mmol) in a mixture of EtOH-Sat. NaHCO$_3$ (3:2, 10 mL) will be added. The resulting solution will be heated until the reaction is complete. The resulting reaction mixture would be worked up and residue purified to obtain the coupling product. Treatment of this purified product with 30% TFA in DCM will give C9 ($R^3$=2, 5-difluorophenyl, $R^1$=Methyl, $R^{14}$=p-F-phenyl and W is —C(O)—) after purification.

Human Cathepsin D FRET Assay

The substrate used below has been described (Y. Yasuda et al., J. Biochem., 125, 1137 (1999)). Substrate and enzyme are commercially available.

The assay can be run in a 30 μl final volume using a 384 well Nunc black plate. 8 concentrations of compound can be pre-incubated with enzyme for 30 mins at 37° C. followed by addition of substrate with continued incubation at 37° C. for 45 mins. The rate of increase in fluorescence is linear for over 1 h and is measured at the end of the incubation period using a Molecular Devices FLEX station plate reader. Kis are interpolated from the IC$_{50}$s using a Km value of 4 μM and the substrate concentration of 2.5 μM.

Reagents
Na-Acetate pH 5
1% Brij-35 from 10% stock (Calbiochem)
DMSO
Purified (>95%) human liver Cathepsin D (Athens Research & Technology Cat#16-12-030104)
Peptide substrate(Km=4 uM) Mca-Gly-Lys-Pro-Ile-Leu-Phe-Phe-Arg-Leu-Lys(Dnp)-D-Arg-NH$_2$ Bachem Cat #M-2455
Pepstatin is used as a control inhibitor (Ki~0.5 nM) and is available from Sigma.
Nunc 384 well black plates
Final Assay Buffer Conditions
100 mM Na Acetate pH 5.0
0.02% Brij-35
1% DMSO Compound can be diluted to 3× final concentration in assay buffer containing 3% DMSO. 10 μl of compound will be added to 10 μl of 2.25 nM enzyme (3×) diluted in assay buffer without DMSO, mixed briefly, spun, and can be incubated at 37° C. for 30 mins. 3× substrate (7.5 μM) is prepared in 1× assay buffer without DMSO. 10 μl of substrate will be added to each well mixed and spun briefly to initiate the reaction. Assay plates can be incubated at 37 C for 45 mins and read on 384 compatible fluorescence plate reader using a 328 nm Ex and 393 nm Em.

BACE-1 Cloning, Protein Expression and Purification

A predicted soluble form of human BACE1 (sBACE1, corresponding to amino acids 1-454) can be generated from the full length BACE1 cDNA (full length human BACE1 cDNA in pcDNA4/mycHisA construct; University of Toronto) by PCR using the advantage-GC cDNA PCR kit (Clontech, Palo Alto, Calif.). A HindIII/PmeI fragment from pcDNA4-sBACE1 myc/His can be blunt ended using Klenow and subcloned into the Stu I site of pFASTBACI(A) (Invitrogen). A sBACE1mycHis recombinant bacmid can be generated by transposition in DH10Bac cells (GIBCO/BRL). Subsequently, the sBACE1mycHis bacmid construct can be transfected into sf9 cells using CellFectin (Invitrogen, San Diego, Calif.) in order to generate recombinant baculovirus. Sf9 cells are grown in SF 900-II medium (Invitrogen) supplemented with 3% heat inactivated FBS and 0.5× penicillin/streptomycin solution (Invitrogen). Five milliliters of high titer plaque purified sBACEmyc/His virus is used to infect 1 L of logarithmically growing sf9 cells for 72 hours. Intact cells are pelleted by centrifugation at 3000×g for 15 minutes. The supernatant, containing secreted sBACE1, is collected and diluted 50% v/v with 100 mM HEPES, pH 8.0. The diluted medium is loaded onto a Q-sepharose column. The Q-sepharose column is washed with Buffer A (20 mM HEPES, pH 8.0, 50 mM NaCl).

Proteins, can be eluted from the Q-sepharose column with Buffer B (20 mM HEPES, pH 8.0, 500 mM NaCl). The protein peaks from the Q-sepharose column are pooled and loaded onto a Ni-NTA agarose column. The Ni-NTA column can be then washed with Buffer C (20 mM HEPES, pH 8.0, 500 mM NaCl). Bound proteins are then eluted with Buffer D (Buffer C+250 mM imidazole). Peak protein fractions as determined by the Bradford Assay (Biorad, CA) are concentrated using a Centricon 30 concentrator (Millipore). sBACE1 purity is estimated to be ~90% as assessed by SDS-PAGE and Commassie Blue staining. N-terminal sequencing indicates that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin; CIS-Bio International, France), 5 μM unlabeled APPsw peptide (KTEEISEVNLDAEFRHDK; American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol are preincubated for 30 min at 30° C. Reactions are initiated by addition of substrate in a 5 μl aliquot resulting in a total volume of 25 μl. After 3 hr at 30° C. reactions are terminated by addition of an equal volume of 2× stop buffer containing 50 mM Tris-HCl pH 8.0, 0.5 M KF, 0.001% Brij-35, 20 μg/ml SA-XL665 (cross-linked allophycocyanin protein coupled to streptavidin; CIS-Bio International, France) (0.5 μg/well). Plates are shaken briefly and spun at 1200×g for 10 seconds to pellet all liquid to the bottom of the plate before the incubation. HTRF measurements are made on a Packard Discovery® HTRF plate reader using 337 nm laser light to excite the sample followed by a 50 μs delay and simultaneous measurements of both 620 nm and 665 nm emissions for 400 μs.

IC$_{50}$ determinations for inhibitors, (I), are determined by measuring the percent change of the relative fluorescence at 665 nm divided by the relative fluorescence at 620 nm, (665/

620 ratio), in the presence of varying concentrations of I and a fixed concentration of enzyme and substrate. Nonlinear regression analysis of this data can be performed using GraphPad Prism 3.0 software selecting four parameter logistic equation, that allows for a variable slope. Y=Bottom+(Top-Bottom)/(1+10^((Log EC50−X)*Hill Slope)); X is the logarithm of concentration of I, Y is the percent change in ratio and Y starts at bottom and goes to top with a sigmoid shape.

Using the above assay, the $K_i$ values of some of the compounds were determined. The $K_i$ values ranged from 0.1 to 100,000 nM.

Human Mature Renin Enzyme Assay

Human Renin can be cloned from a human kidney cDNA library and C-terminally epitope-tagged with the V5-6His sequence into pcDNA3.1. pCNDA3.1-Renin-V5-6His is stably expressed in HEK293 cells and purified to >80% using standard Ni-Affinity chromatography. The prodomain of the recombinant human renin-V5-6His can be removed by limited proteolysis using immobilized TPCK-trypsin to give mature-human renin. Renin enzymatic activity can be monitored using a commercially available fluorescence resonance energy transfer (FRET) peptide substrate, RS-1 (Molecular Probes, Eugene, Oreg.) in 50 mM Tris-HCl pH 8.0, 100 mM NaCl, 0.1% Brij-35 and 5% DMSO buffer for 40 mins at 30° Celsius in the presence or absence of different concentrations of test compounds. Mature human Renin is present at approximately 200 nM. Inhibitory activity is defined as the percent decrease in renin induced fluorescence at the end of the 40 min incubation compared to vehicle controls and samples lacking enzyme.

In the aspect of the invention relating to a combination of at least one compound of formula I with at least one cholinesterase inhibitor, acetyl- and/or butyrylcholinesterase inhibitors can be used. Examples of cholinesterase inhibitors are tacrine, donepezil, rivastigmine, galantamine, pyridostigmine and neostigmine, with tacrine, donepezil, rivastigmine and galantamine being preferred. Preferably, these combinations are directed to the treatment of Alzheimer's Disease.

In other aspects of the invention relating to a combination of at least one compound of formula I and at least one other agent, for example a beta secretase inhibitor; a gamma secretase inhibitor; an HMG-CoA reductase inhibitor such as atorvastatin, lovastatin, simvastatin, pravastatin, fluvastatin and rosuvastatin; non-steroidal anti-inflammatory agents such as, but not necessarily limited to ibuprofen, relafen or naproxen; N-methyl-D-aspartate receptor antagonists such as memantine; anti-amyloid antibodies including humanized monoclonal antibodies; vitamin E; nicotinic acetylcholine receptor agonists; CB1 receptor inverse agonists or CB1 receptor antagonists; antibiotics such as doxycycline; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity. Preferably, these combinations are directed to the treatment of Alzheimer's Disease.

In the aspect of the invention relating to a combination of a compound of formula I with a muscarinic agonist or antagonist, $m_1$ agonists or $m_2$ antagonists can be used. Examples of $m_1$ agonists are known in the art and include but are not limited to Oxotremorine, Cevimeline, and others. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Other example of pharmaceutical agents include beta secretase inhibitors; HMG-CoA reductase inhibitors, such as atorvastatin, lovastatin, simvistatin, pravastatin, fluvastatin and rosuvastatin; non-steroidal anti-inflammatory agents, such as ibuprofen, N-methyl-D-aspartate receptor antagonists, such as memantine, anti-amyloid antibodies including humanized monoclonal antibodies; vitamin E; nicotinic acetylcholine receptor agonists; CB1 receptor inverse agonists or CB1 receptor antagonists; antibiotics, e.g., docycycline; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity, and cholesterol absorption inhibitors; e.g., bile sequestants or azetidinones, such as ezetimibe (ZETIA).

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

When a compound of formula I is used in combination with a cholinesterase inhibitor to treat cognitive disorders, these two active components may be co-administered simultaneously or sequentially, or a single pharmaceutical composition comprising a compound of formula I and a cholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the cholinesterase inhibitor can be determined from published material, and may range from 0.001 to 100 mg/kg body weight.

When separate pharmaceutical compositions of a compound of formula I and a cholinesterase inhibitor are to be administered, they can be provided in a kit comprising in a single package, one container comprising a compound of formula I in a pharmaceutically acceptable carrier, and a separate container comprising a cholinesterase inhibitor in a pharmaceutically acceptable carrier, with the compound of formula I and the cholinesterase inhibitor being present in amounts such that the combination is therapeutically effective. A kit is advantageous for administering a combination when, for example, the components must be administered at different time intervals or when they are in different dosage forms.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A compound having the structural Formula (I):

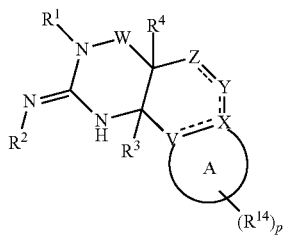

Formula (I)

or a stereoisomer, tautomer, or pharmaceutically acceptable salt thereof, wherein $R^1$, $R^2$, $R^3$, $R^4$, W, Z, Y, X, V, A, p, and each $R^{14}$ is selected independently of each other and wherein:

p is an integer from 0 to 5;

the dashed line (-----) in Formula (I) represent single or double bonds;

ring A together with V and X forms a mono or multicyclic 4 to 12 membered cycloalkylene, cycloalkenylene, heterocycloalkylene or heterocycloalkenylene wherein the heteroatom or heteroatoms of said heterocycloalkylene or heterocycloalkenylene are independently selected from the group consisting of —O—, —S—, —S(O)—, —S(O)$_2$— and —N($R^5$)—;

or ring A together with V and X forms a mono or multicyclic 4 to 12 membered arylene or heteroarylene;

W is —S(O)—, —S(O)$_2$—, —C(O)— or —O—;

X is —N— or —C($R^{30}$)—, with the proviso that when X is —N—, Y cannot be —S—;

Y is —N($R^5$)—, —O—, —S—, —C($R^6$)($R^{6a}$)—, —C(O)—, —S(O)— or —S(O)$_2$—;

Z is a bond, —N($R^5$)—, —O—, —S—, —C($R^6$)($R^{6a}$)—, —C(O)—, —S(O)— or —S(O)$_2$— with the proviso that when Z is —O—, —S—, —S(O)— or —S(O)$_2$—, Y cannot be —O—, —S—, —S(O)— or —S(O)$_2$—;

or Z and Y taken together is —C=C—, —N=C— or —C=N—;

or X and Y taken together is —C=C—, —N=C— or —C=N—;

V is —C($R^{31}$)—;

or V and X taken together forms —C=C—;

with the proviso that there are no cumulative double bonds between V, X, Y, Z and the ring atoms of ring A adjacent to V and X;

each of $R^1$, $R^2$ and $R^5$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —CN, —C(=NR$^{11}$)R$^8$, —C(O)R$^8$, —C(O)OR$^9$, —S(O)R$^{10}$, —S(O)$_2$R$^{10}$, —C(O)N(R$^{11}$)(R$^{12}$), —S(O)N(R$^{11}$)(R$^{12}$), —S(O)$_2$N(R$^{11}$)(R$^{12}$), —NO$_2$, —N=C(R$^8$)$_2$ and —N(R$^{11}$)(R$^{12}$), provided that $R^1$ and $R^5$ are not both selected from —NO$_2$, —N=C(R$^8$)$_2$ and —N(R$^{11}$)(R$^{12}$);

each of $R^3$, $R^4$, $R^6$, and $R^{6a}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —SH, —CN, —OR$^9$, —C(O)R$^8$, —C(O)OR$^9$, —C(O)N(R$^{11}$)(R$^{12}$), —SR$^{19}$, —S(O)N(R$^{11}$)(R$^{12}$), —S(O)$_2$N(R$^{11}$)(R$^{12}$), —N(R$^{11}$)(R$^{12}$), —N(R$^{11}$)C(O)R$^8$, —N(R$^{11}$)S(O)R$^{10}$, —N(R$^{11}$)S(O)$_2$R$^{10}$, —N(R$^{11}$)C(O)N(R$^{12}$)(R$^{13}$), —N(R$^{11}$)C(O)OR$^9$ and —C(=NOH)R$^8$;

or a $R^6$ and a $R^{6a}$ group together with the carbon to which they are attached form a carbonyl;

each $R^8$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —OR$^{15}$, —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$) and —N(R$^{15}$)C(O)OR$^{16}$;

each $R^{14}$ is independently selected from the group consisting of a bond, H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —N(R$^{15}$)C(O)N(R$^{16}$)(R$^{17}$), —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), and —N(R$^{15}$)C(O)OR$^{16}$;

or two $R^{14}$ groups together with the carbon to which they are attached form a carbonyl;

each $R^9$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, and heterocycloalkenylheteroaryl;

each $R^{10}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl and —N($R^{15}$)($R^{16}$);

each of $R^{11}$, $R^{12}$ and $R^{13}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —C(O)$R^8$, —C(O)O$R^9$, —S(O)$R^{10}$, —S(O)$_2R^{10}$, —C(O)N($R^{15}$)($R^{16}$), —S(O)N($R^{15}$)($R^{16}$), —S(O)$_2$N($R^{15}$)($R^{16}$) and —CN;)

each of $R^{15}$, $R^{16}$ and $R^{17}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, aryl heterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, $R^{18}$-alkyl, $R^{18}$-arylalkyl, $R^{18}$-heteroarylalkyl, $R^{18}$-cycloalkylalkyl, $R^{18}$-heterocycloalkylalkyl, $R^{18}$-arylcycloalkylalkyl, $R^{18}$-heteroarylcycloalkylalkyl, $R^{18}$-arylheterocycloalkylalkyl, $R^{18}$-heteroarylheterocycloalkylalkyl, $R^{18}$-cycloalkyl, $R^{18}$-arylcycloalkyl, $R^{18}$-heteroarylcycloalkyl, $R^{18}$-heterocycloalkyl, $R^{18}$-arylheterocycloalkyl, $R^{18}$-heteroarylheterocycloalkyl, $R^{18}$-alkenyl, $R^{18}$-arylalkenyl, $R^{18}$-cycloalkenyl, $R^{18}$-arylcycloalkenyl, $R^{18}$-heteroarylcycloalkenyl, $R^{18}$-heterocycloalkenyl, $R^{18}$-arylheterocycloalkenyl, $R^{18}$-heteroarylheterocycloalkenyl, $R^{18}$-alkynyl, $R^{18}$-arylalkynyl, $R^{18}$-aryl, $R^{18}$-cycloalkylaryl, $R^{18}$-heterocycloalkylaryl, $R^{18}$-cycloalkenylaryl, $R^{18}$-heterocycloalkenylaryl, $R^{18}$-heteroaryl, $R^{18}$-cycloalkylheteroaryl, $R^{18}$-heterocycloalkylheteroaryl, $R^{18}$-cycloalkenylheteroaryl, and $R^{18}$-heterocycloalkenylheteroaryl;

each $R^{18}$ is independently 1-5 substituents independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, aryl heterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —NO$_2$, halo, HO-alkoxyalkyl, —CF$_3$, —CN, alkyl-CN, —C(O)$R^{19}$, —C(O)OH, —C(O)O$R^{19}$, —C(O)NH$R^{20}$, —C(O)NH$_2$, —C(O)NH$_2$—C(O)N(alkyl)$_2$, —C(O)N(alkyl)(aryl), —C(O)N(alkyl)(heteroaryl), —S$R^{19}$, —S(O)$_2R^{20}$, —S(O)NH$_2$, —S(O)NH(alkyl), —S(O)N(alkyl)(alkyl), —S(O)NH(aryl), —S(O)$_2$NH$_2$, —S(O)$_2$NH$R^{19}$, —S(O)$_2$NH(heterocycloalkyl), —S(O)$_2$N(alkyl)$_2$, —S(O)$_2$N(alkyl)(aryl), —OCF$_3$, —OH, —O$R^{20}$, —O-heterocycloalkyl, —O-cycloalkylalkyl, —O-heterocycloalkylalkyl, —NH$_2$, —NH$R^{20}$, —N(alkyl)$_2$, —N(arylalkyl)$_2$, —N(arylalkyl)-(heteroarylalkyl), —NHC(O)$R^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or two $R^{18}$ moieties on adjacent carbons can be linked together to form

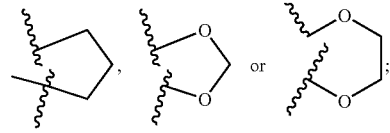

each $R^{19}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl;

each $R^{20}$ is independently selected from the group consisting of halo substituted aryl, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl, and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, in $R^1$, $R^2$, $R^3$, $R^4$, $R^5$, $R^6$, $R^{6a}$, $R^8$, $R^9$, $R^{10}$, $R^{11}$, $R^{12}$, $R^{13}$ and $R^{14}$;

is independently unsubstituted or substituted by 1 to 5 $R^{21}$ groups, wherein each $R^{21}$ group is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CN, —$OR^{15}$, —$C(O)R^{15}$, —$C(O)OR^{15}$, —$C(O)N(R^{15})(R^{16})$, —$SR^{15}$, —$S(O)N(R^{15})(R^{16})$, —$CH(R^{15})(R^{16})$, —$S(O)_2N(R^{15})(R^{16})$, —$C(=NR^{15})R^{16}$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$CH_2$—$N(R^{15})C(O)N(R^{16})(R^{17})$, —$CH_2$—$R^{15}$; —$CH_2N(R^{15})(R^{16})$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$S(O)R^{15}$, —$N_3$, —$NO_2$ and —$S(O)_2R^{15}$;

and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl groups in $R^{21}$ is independently unsubstituted or substituted by 1 to 5 $R^{22}$ groups, wherein each $R^{22}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —$CF_3$, —CN, —$OR^{15}$, —$C(O)R^{15}$, —$C(O)OR^{15}$, -alkyl-$C(O)$ $OR^{15}$, —$C(O)N(R^{15})(R^{16})$, —$SR^{15}$, —$S(O)N(R^{15})(R^{16})$, —$S(O)_2N(R^{15})(R^{16})$, —$C(=NR^{15})R^{16}$, —$C(=NOR^{15})R^{16}$, —$P(O)(OR^{15})(OR^{16})$, —$N(R^{15})(R^{16})$, -alkyl-$N(R^{15})(R^{16})$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})(R^{17})$, —$N(R^{15})C(O)$ $N(R^{16})(R^{17})$, —$CH_2$—$N(R^{15})C(O)N(R^{16})(R^{17})$, —$N(R^{15})C(O)OR^{16}$, —$CH_2$—$N(R^{15})C(O)OR^{16}$, —$N_3$, —$NO_2$, —$S(O)R^{15}$ and —$S(O)_2R^{15}$;

or two $R^{21}$ or two $R^{22}$ moieties on adjacent carbons can be linked together to form

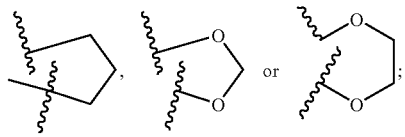

and when $R^{21}$ or $R^{22}$ are each independently selected from the group consisting of —$C(=NOR^{15})R^{16}$, —$N(R^{15})C(O)R^{16}$, —$CH_2$—$N(R^{15})C(O)R^{16}$, —$N(R^{15})S(O)R^{16}$, —$N(R^{15})S(O)_2R^{16}$, —$CH_2$—$N(R^{15})S(O)_2R^{16}$, —$N(R^{15})S(O)_2N(R^{16})(R^{17})$, —$N(R^{15})S(O)N(R^{16})$ $(R^{17})$, —$N(R^{15})C(O)N(R^{16})(R^{17})$, —$CH_2$—$N(R^{15})C(O)N(R^{16})(R^{17})$, —$N(R^{15})C(O)OR^{16}$ and —$CH_2$—$N(R^{15})C(O)OR^{16}$, $R^{15}$ and $R^{16}$ together can be a $C_2$ to $C_4$ chain wherein, optionally, one, two or three ring carbons can be replaced by —$C(O)$— or —$N(H)$— and $R^{15}$ and $R^{16}$, together with the atoms to which they are attached, form a 5 to 7 membered ring, optionally substituted by from 1 to 5 groups $R^{23}$;

each $R^{23}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenyiheteroaryl, heterocycloalkenylheteroaryl, halo, —CN, —OR$^{24}$, —C(O)R$^{24}$, —C(O)OR$^{24}$, —C(O)N(R$^{24}$)(R$^{25}$)—SR$^{24}$, —S(O)N(R$^{24}$)(R$^{25}$), —S(O)$_2$N(R$^{24}$)(R$^{25}$), —C(=NOR$^{24}$)R$^{25}$, —(O)(OR$^{24}$)(OR$^{25}$), —N(R$^{24}$)(R$^{25}$), -alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$; and wherein each of the alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenyiheteroaryl and heterocycloalkenylheteroaryl groups in R$^{23}$ are independently unsubstituted or substituted by 1 to 5 R$^{27}$ groups, wherein each group R$^{27}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CF$_3$, —CN, —OR$^{24}$, —C(O)R$^{24}$, —C(O)OR$^{24}$, alkyl-C(O)OR$^{24}$, —C(O)N(R$^{24}$)(R$^{25}$), —SR$^{24}$, —S(O)N(R$^{24}$)(R$^{25}$), —S(O)$_2$N(R$^{24}$)(R$^{25}$), —C(=NOR$^{24}$)R$^{25}$, —P(O)(OR$^{24}$)(OR$^{25}$), —N(R$^{24}$)(R$^{25}$)-alkyl-N(R$^{24}$)(R$^{25}$), —N(R$^{24}$)C(O)R$^{25}$, —CH$_2$—N(R$^{24}$)C(O)R$^{25}$, —N(R$^{24}$)S(O)R$^{25}$, —N(R$^{24}$)S(O)$_2$R$^{25}$, —CH$_2$—N(R$^{24}$)S(O)$_2$R$^{25}$, —N(R$^{24}$)S(O)$_2$N(R$^{25}$)(R$^{26}$), —N(R$^{24}$)S(O)N(R$^{25}$)(R$^{26}$), —N(R$^{24}$)C(O)N(R$^{25}$)(R$^{26}$), —CH$_2$—N(R$^{24}$)C(O)N(R$^{25}$)(R$^{26}$), —N(R$^{24}$)C(O)OR$^{25}$, —CH$_2$—N(R$^{24}$)C(O)OR$^{25}$, —S(O)R$^{24}$ and —S(O)$_2$R$^{24}$;

each of R$^{24}$, R$^{25}$ and R$^{26}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroaryl heterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, R$^{27}$-alkyl, R$^{27}$-arylalkyl, R$^{27}$-heteroarylalkyl, R$^{27}$-cycloalkylalkyl, R$^{27}$-heterocycloalkylalkyl, R$^{27}$-arylcycloalkylalkyl, R$^{27}$-heteroarylcycloalkylalkyl, R$^{27}$-arylheterocycloalkylalkyl, R$^{27}$-heteroarylheterocycloalkylalkyl, R$^{27}$-cycloalkyl, R$^{27}$-arylcycloalkyl, R$^{27}$-heteroarylcycloalkyl, R$^{27}$-heterocycloalkyl, R$^{27}$-arylheterocycloalkyl, R$^{27}$-heteroarylheterocycloalkyl, R$^{27}$-alkenyl, R$^{27}$-arylalkenyl, R$^{27}$-cycloalkenyl, R$^{27}$-arylcycloalkenyl, R$^{27}$-heteroarylcycloalkenyl, R$^{27}$-heterocycloalkenyl, R$^{27}$-arylheterocycloalkenyl, R$^{27}$-heteroarylheterocycloalkenyl, R$^{27}$-alkynyl, R$^{27}$-arylalkynyl, R$^{27}$-aryl, R$^{27}$-cycloalkylaryl, R$^{27}$-heterocycloalkylaryl, R$^{27}$-cycloalkenylaryl, R$^{27}$-heterocycloalkenylaryl, R$^{27}$-heteroaryl, R$^{27}$-cycloalkylheteroaryl, R$^{27}$-heterocycloalkylheteroaryl, R$^{27}$-cycloalkenylheteroaryl and R$^{27}$-heterocycloalkenylheteroaryl;

R$^{27}$ is 1-5 substituents, each independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroaryl heterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, —NO$_2$, halo, —CF$_3$, —CN, alkyl-CN, —C(O)R$^{28}$, —C(O)OH, —C(O)OR$^{28}$, —C(O)NHR$^{29}$, —C(O)N(alkyl)$_2$, —C(O)N(alkyl)(aryl), —C(O)N(alkyl)(heteroaryl), —SR$^{28}$, —S(O)$_2$R$^{29}$, —S(O)NH$_2$, —S(O)NH(alkyl), —S(O)N(alkyl)(alkyl), —S(O)NH(aryl), —S(O)$_2$NH$_2$, —S(O)$_2$NHR$^{28}$, —S(O)$_2$NH(aryl), —S(O)$_2$NH(heterocycloalkyl), —S(O)$_2$N(alkyl)$_2$, —S(O)$_2$N(alkyl)(aryl), —OH, —OR$^{29}$, —O-heterocycloalkyl, —O-cycloalkylalkyl, —O-heterocycloalkylalkyl, —NH$_2$, —NHR$^{29}$, —N(alkyl)$_2$, —N(arylalkyl)$_2$, —N(arylalkyl)(heteroarylalkyl), —NHC(O)R$^{29}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2$R$^{29}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

each R$^{28}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl;

each R$^{29}$ is independently selected from the group consisting of alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloakenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl and heterocycloalkenylheteroaryl each $R^{30}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, aryl heterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —N(R$^{15}$)C(O)N(R$^{16}$)(R$^{17}$), —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), and —N(R$^{15}$)C(O)OR$^{16}$;

or two $R^{30}$ groups together with the carbon to which they are attached form a carbonyl; and each $R^{31}$ is independently selected from the group consisting of H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, cycloalkenylaryl, heterocycloalkenylaryl, heteroaryl, cycloalkylheteroaryl, heterocycloalkylheteroaryl, cycloalkenylheteroaryl, heterocycloalkenylheteroaryl, halo, —CH$_2$—O—Si(R$^9$)(R$^{10}$)(R$^{19}$), —N(R$^{15}$)C(O)N(R$^{16}$)(R$^{17}$), —CN, —OR$^{15}$, —C(O)R$^{15}$, —C(O)OR$^{15}$, —C(O)N(R$^{15}$)(R$^{16}$), —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), —N(R$^{15}$)C(O)R$^{16}$, —N(R$^{15}$)S(O)R$^{16}$, —N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), and —N(R$^{15}$)C(O)OR$^{16}$;

or $R^{31}$ forms a double bond with an adjacent ring atom or ring heteroatom of ring A (other than X);

or two $R^{31}$ groups together with the carbon to which they are attached form a carbonyl.

2. A compound of claim 1 wherein $R^1$ is alkyl.

3. A compound of claim 2 wherein $R^1$ is methyl.

4. A compound of claim 1 wherein $R^2$ is H.

5. A compound of claim 1 wherein $R^3$ is H, alkyl, arylalkyl, heteroarylalkyl, cycloalkylalkyl, heterocycloalkylalkyl, arylcycloalkylalkyl, heteroarylcycloalkylalkyl, arylheterocycloalkylalkyl, heteroarylheterocycloalkylalkyl, cycloalkyl, arylcycloalkyl, heteroarylcycloalkyl, heterocycloalkyl, arylheterocycloalkyl, heteroarylheterocycloalkyl, alkenyl, arylalkenyl, cycloalkenyl, arylcycloalkenyl, heteroarylcycloalkenyl, heterocycloalkenyl, arylheterocycloalkenyl, heteroarylheterocycloalkenyl, alkynyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

6. A compound of claim 1 wherein $R^3$ is arylalkyl, heteroarylalkyl, arylcycloalkylalkyl, heteroarylcycloalkylalkyl, arylheterocycloalkylalkyl, heteroarylheterocycloalkylalkyl, arylcycloalkyl, heteroarylcycloalkyl, arylheterocycloalkyl, heteroarylheterocycloalkyl, arylalkenyl, arylcycloalkenyl, heteroarylcycloalkenyl, arylheterocycloalkenyl, heteroarylheterocycloalkenyl, arylalkynyl, aryl, cycloalkylaryl, heterocycloalkylaryl, heterocycloalkenylaryl, heteroaryl, cycloalkylheteroaryl, heterocycloalkylheteroaryl, cycloalkenylaryl or heterocycloalkenylaryl.

7. A compound of claim 1 wherein $R^3$ is arylalkyl, heteroarylalkyl, arylcycloalkyl, heteroarylcycloalkyl, arylalkenyl, arylalkynyl, aryl or heteroaryl.

8. A compound of claim 1 wherein $R^3$ is heteroaryl or aryl.

9. A compound of claim 1 wherein $R^3$ is

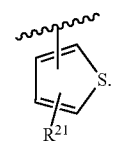

10. A compound of claim 1 wherein $R^{21}$ is —CN.

11. A compound of claim 1 wherein $R^3$ is

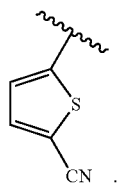

12. A compound of claim 1 wherein W is —C(O)—.

13. A compound of claim 1 wherein $R^4$ is H, alkyl or halo.

14. A compound of claim 1 wherein Z is a bond.

15. A compound of claim 1 wherein A together with V and X forms a heteroarylene or arylene.

16. A compound of claim 1 wherein ring A together with V and X forms the following:

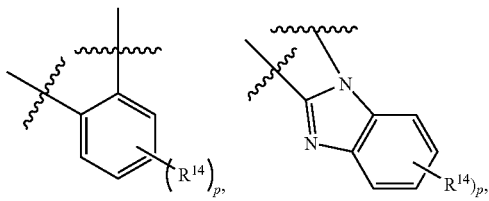

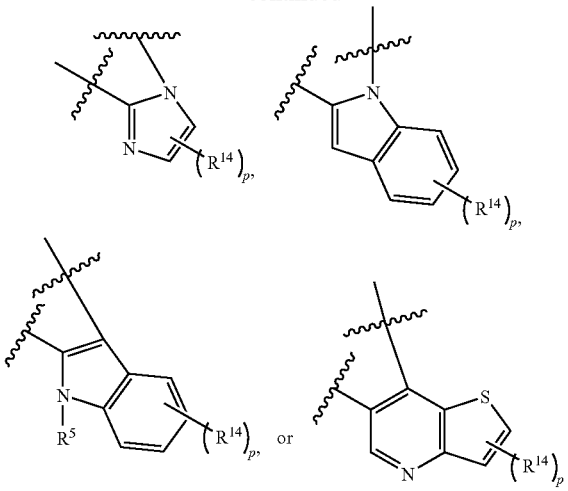

17. A compound of claim 16 wherein $R^{14}$ is alkyl or halo.
18. A compound of claim 1 wherein $R^{14}$ is methyl.
19. A compound of claim 1 wherein $R^{14}$ is F.
20. A compound of claim 1 wherein X is —N— or —C($R^{30}$)—.
21. A compound of claim 1 wherein Y is —C($R^6$)($R^{6a}$)—.
22. A compound of claim 21 wherein $R^6$ is H and $R^{6a}$ is H.
23. A compound of claim 1 wherein Z is a bond and Y is —C($R^6$)($R^{6a}$)—.
24. A compound of claim 1 wherein
Z is a bond;
ring A together with V and X form the following:

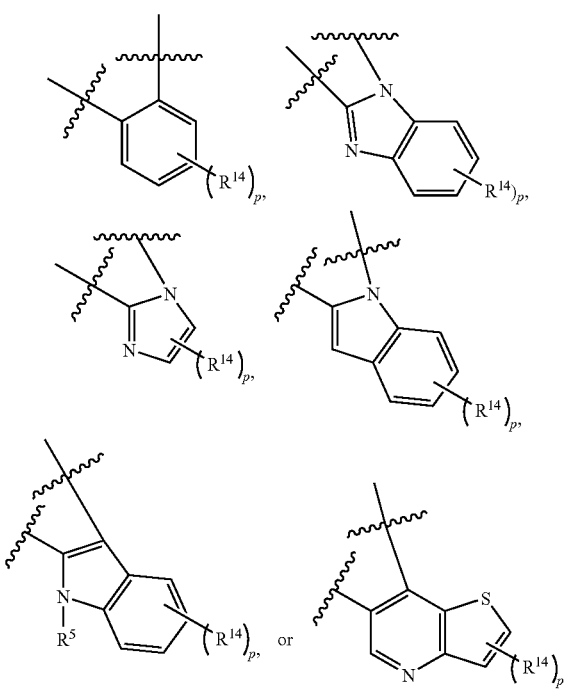

and Y is —C($R^6$)($R^{6a}$)—.

25. A compound of claim 24 wherein Y is —CH$_2$—.
26. A compound of claim 1 wherein V-X is

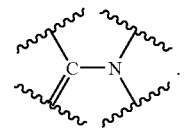

27. A compound of claim 1 wherein V=X is

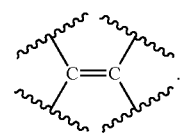

28. A compound of claim 1 wherein A together with V and X forms the following:

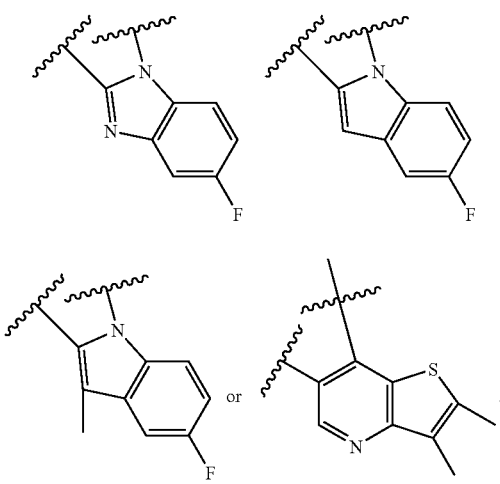

29. A compound of claim 1, wherein each of $R^{15}$, $R^{16}$ and $R^{17}$ is independently selected from the group consisting of

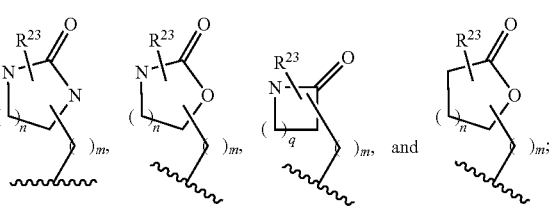

wherein each $R^{23}$ independently numbers 0 to 5 substituents, each m is, independently, 0 to 6, each n is, independently, 0 to 5, and each q is independently 1 to 5.

30. A compound selected from the group consisting of:

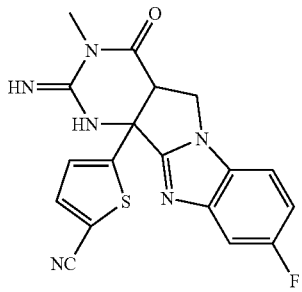

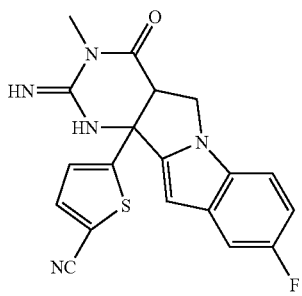

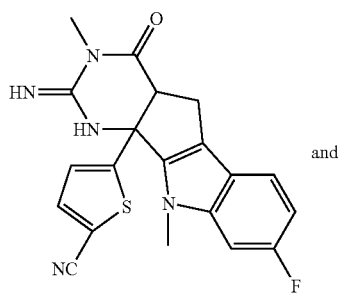 and

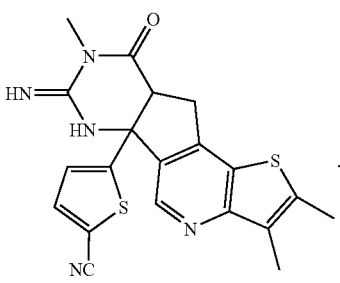

31. A compound of claim 1, having the general structure shown in Formula (III.c.2):

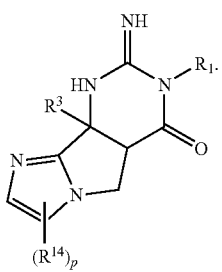

(II.c.2)

32. A compound of claim 1, having the general structure shown in Formula (III.c.2A):

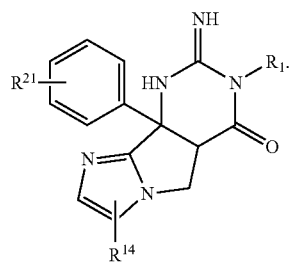

(III.c.2A)

33. A compound of claim 1, having the general structure shown in Formula (III.c.2B):

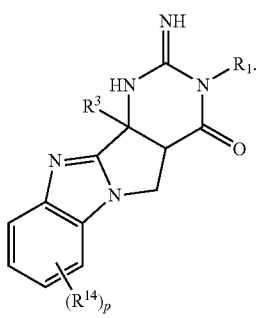

(III.c.2B)

34. A compound of claim 1, having the general structure shown in Formula (III.c.2B1):

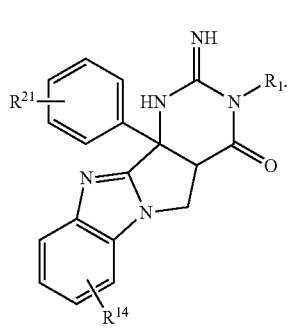

(III.c.2B1)

35. A compound of claim 1, having the general structure shown in Formula (IV.a):

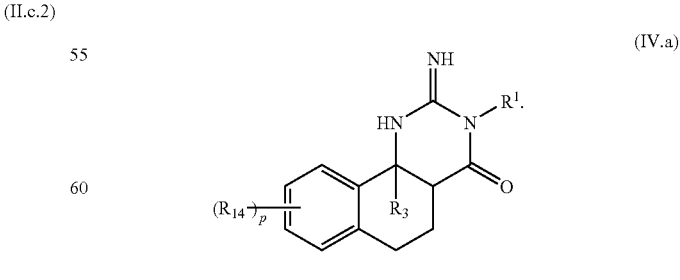

(IV.a)

36. A pharmaceutical composition comprising an effective amount of a compound of claim 1 and a pharmaceutically effective carrier.

37. A pharmaceutical composition comprising an effective amount of a compound of claim 31 and a pharmaceutically effective carrier.

38. A method of inhibiting an aspartyl protease comprising contacting a population of cells expressing an aspartyl protease with an effective amount of a compound of claim 1.

39. A method of inhibiting an aspartyl protease comprising contacting a population of cells expressing an aspartyl protease with an effective amount of a compound of claim 31.

40. A pharmaceutical composition comprising an effective amount of a compound of claim 1, and an effective amount of a cholinesterase inhibitor or a muscarinic $m_1$ agonist or $m_2$ antagonist in a pharmaceutically effective carrier.

41. A pharmaceutical composition comprising an effective amount of a compound of claim 31 and an effective amount of a cholinesterase inhibitor or a muscarinic $m_1$ agonist or $m_2$ antagonist in a pharmaceutically effective carrier.

42. A pharmaceutical composition comprising an effective amount of a compound of claim 1, and an effective amount of a gamma secretase inhibitor; an HMG-CoA reductase inhibitor or a non-steroidal anti-inflammatory agent.

43. A pharmaceutical composition comprising an effective amount of a compound of claim 31 and an effective amount of a gamma secretase inhibitor; an HMG-CoA reductase inhibitor or a non-steroidal anti-inflammatory agent.

44. A compound of claim 1 having a structure selected from the group consisting of:

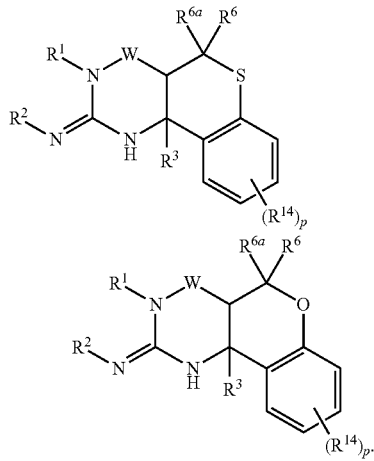

45. A compound of claim 1 having a structure selected from the group consisting of:

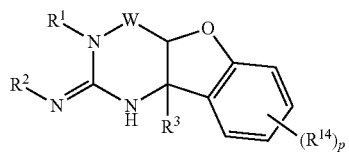

46. A compound of claim 1 having a structure selected from the group consisting of:

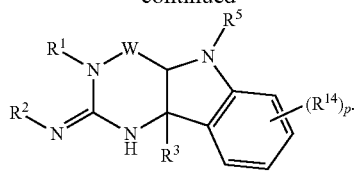

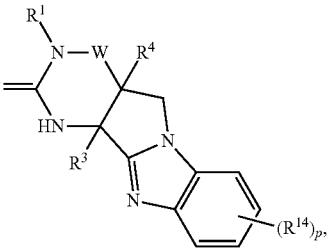

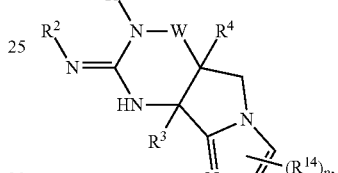

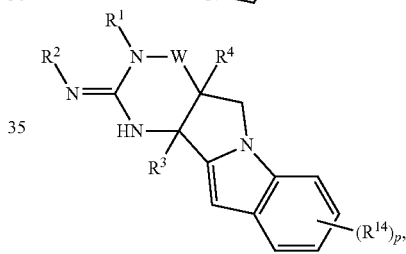

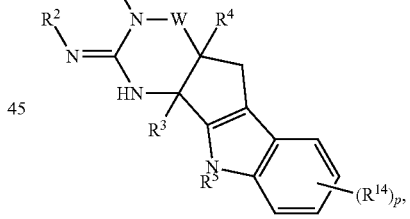

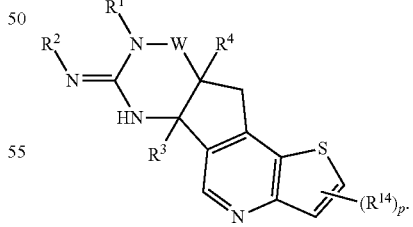

* * * * *